United States Patent
Fetzer et al.

(10) Patent No.: US 9,315,781 B2
(45) Date of Patent: *Apr. 19, 2016

(54) INFECTIOUS CDNA CLONE OF EUROPEAN PRRS VIRUS AND USES THEREOF

(75) Inventors: Christiane Fetzer, Tuebingen (DE); Andreas Gallei, Hannover (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/235,596

(22) PCT Filed: Jul. 30, 2012

(86) PCT No.: PCT/EP2012/064888
§ 371 (c)(1),
(2), (4) Date: Mar. 20, 2014

(87) PCT Pub. No.: WO2013/017568
PCT Pub. Date: Feb. 7, 2013

(65) Prior Publication Data
US 2014/0314808 A1    Oct. 23, 2014

(30) Foreign Application Priority Data

Jul. 29, 2011 (EP) .................................. 11176019
Jul. 29, 2011 (EP) .................................. 11176023

(51) Int. Cl.
*C12N 7/00* (2006.01)
*A61K 39/12* (2006.01)
*C07K 14/005* (2006.01)
*A61K 39/00* (2006.01)

(52) U.S. Cl.
CPC . *C12N 7/00* (2013.01); *A61K 39/12* (2013.01); *C07K 14/005* (2013.01); *A61K 2039/5254* (2013.01); *A61K 2039/552* (2013.01); *C12N 2770/10021* (2013.01); *C12N 2770/10022* (2013.01); *C12N 2770/10034* (2013.01); *C12N 2770/10062* (2013.01)

(58) Field of Classification Search
None
See application file for complete search history.

(56) References Cited

U.S. PATENT DOCUMENTS

| | | | |
|---|---|---|---|
| 3,080,291 A | 3/1963 | Sinha et al. |
| 3,137,631 A | 6/1964 | Soloway |
| 3,959,457 A | 5/1976 | Speaker et al. |
| 4,015,100 A | 3/1977 | Gnanamuthu et al. |
| 4,122,167 A | 10/1978 | Buynak et al. |
| 4,205,060 A | 5/1980 | Monsimer et al. |
| 4,224,412 A | 9/1980 | Dorofeev et al. |
| 4,452,747 A | 6/1984 | Gersonde et al. |
| 4,468,346 A | 8/1984 | Paul et al. |
| 4,554,159 A | 11/1985 | Roizman et al. |
| 4,606,940 A | 8/1986 | Frank et al. |
| 4,636,485 A | 1/1987 | van der Smissen |
| 4,744,933 A | 5/1988 | Rha et al. |
| 4,753,884 A | 6/1988 | Kit et al. |
| 4,810,493 A | 3/1989 | Patrick et al. |
| 4,921,706 A | 5/1990 | Roberts et al. |
| 4,927,637 A | 5/1990 | Morano et al. |
| 4,944,948 A | 7/1990 | Uster et al. |
| 5,008,050 A | 4/1991 | Cullis et al. |
| 5,009,956 A | 4/1991 | Baumann |
| 5,132,117 A | 7/1992 | Speaker et al. |
| 5,206,163 A | 4/1993 | Renard et al. |
| 5,213,759 A | 5/1993 | Castberg et al. |
| 5,419,907 A | 5/1995 | Paul et al. |
| 5,476,778 A | 12/1995 | Chladek et al. |
| 5,510,258 A | 4/1996 | Sanderson et al. |
| 5,587,164 A | 12/1996 | Sanderson et al. |
| 5,597,721 A | 1/1997 | Brun et al. |
| 5,620,691 A | 4/1997 | Wensvoort et al. |
| 5,674,500 A | 10/1997 | Peeters et al. |
| 5,677,429 A | 10/1997 | Benfield |
| 5,683,865 A | 11/1997 | Collins et al. |
| 5,690,940 A | 11/1997 | Joo |
| 5,695,766 A | 12/1997 | Paul et al. |
| 5,698,203 A | 12/1997 | Visser et al. |
| 5,789,388 A | 8/1998 | Visser et al. |
| 5,840,563 A | 11/1998 | Chladek et al. |
| 5,846,805 A | 12/1998 | Collins et al. |
| 5,858,729 A | 1/1999 | Van Woensel et al. |
| 5,866,401 A | 2/1999 | Hesse |
| 5,888,513 A | 3/1999 | Plana Duran et al. |
| 5,910,310 A | 6/1999 | Heinen et al. |
| 5,925,359 A | 7/1999 | Van Woensel et al. |

(Continued)

FOREIGN PATENT DOCUMENTS

| | | |
|---|---|---|
| CA | 2103460 A1 | 12/1992 |
| DE | 145705 A1 | 1/1981 |

(Continued)

OTHER PUBLICATIONS

Sequence alignment of instant SEQ ID No. 1 with 13558669 SEQ ID No. 31 Jul. 26, 2012.*
Sequence alignment of SEQ ID No. 1 with SEQ ID No. 13 of 13558669 Jul. 26, 2012.*
"Dutch Team Isolates Mystery Pig Disease Agent", Animal Pharm, vol. 230, Abstract No. 00278268, Jun. 21, 1991, p. 21.
"For purification of viral RNA from Plasma, Serum, Cell-free body fluids, Cell-Culture supernatants". QIAamp® Viral RNA Mini Kit Handbook, QIAGEN, Jan. 1999, Cat #52906, pp. 1-35.
"Frontiers closing to mystery disease pigs". Animal Pharm., No. 228, May 24, 1991, p. 2.

(Continued)

*Primary Examiner* — Shanon A Foley
(74) *Attorney, Agent, or Firm* — Michael P. Morris; Joyce L. Morrison

(57) ABSTRACT

The present invention belongs to the field of animal health and relates to a nucleic acid sequence which comprises the genome of an infectious genotype I (EU) PRRS virus clone useful for studying Porcine Reproductive and Respiratory Syndrome (PRRS), a viral disease affecting swine, and in the development of vaccines, therapeutics and diagnostics for the prophylaxis, treatment and diagnosis of PRRS.

5 Claims, 10 Drawing Sheets

(56) References Cited

U.S. PATENT DOCUMENTS

Figure 2:
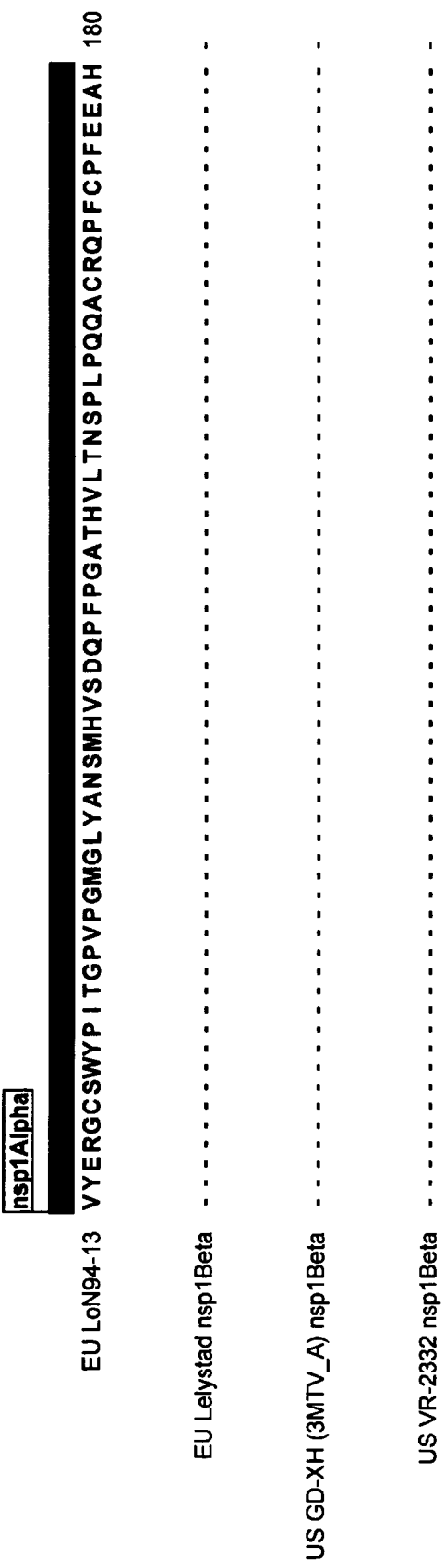
Figure 2:
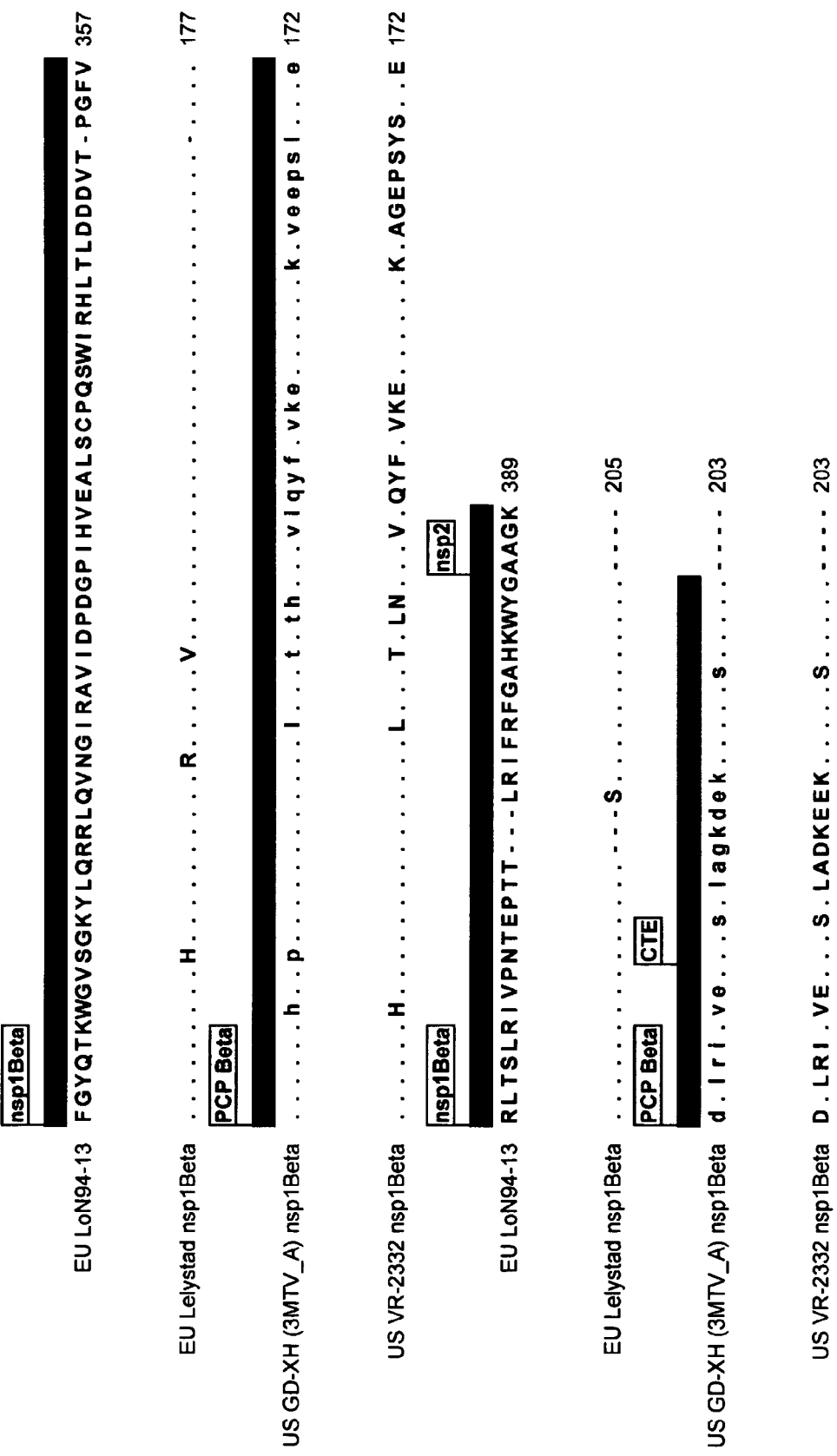

| | | |
|---|---|---|
| 5,968,525 A | 10/1999 | Fitzgerald et al. |
| 5,976,537 A | 11/1999 | Mengeling et al. |
| 5,989,563 A | 11/1999 | Chladek et al. |
| 5,998,601 A | 12/1999 | Murtaugh et al. |
| 6,001,370 A | 12/1999 | Burch et al. |
| 6,015,663 A | 1/2000 | Wesley et al. |
| 6,042,830 A | 3/2000 | Chladek et al. |
| 6,080,570 A | 6/2000 | Chladek et al. |
| 6,110,467 A | 8/2000 | Paul et al. |
| 6,110,468 A | 8/2000 | Collins et al. |
| 6,197,310 B1 | 3/2001 | Wensvoort et al. |
| 6,241,990 B1 | 6/2001 | Collins et al. |
| 6,251,397 B1 | 6/2001 | Paul et al. |
| 6,251,404 B1 | 6/2001 | Paul et al. |
| 6,268,199 B1 | 7/2001 | Meulenberg et al. |
| 6,380,376 B1 | 4/2002 | Paul et al. |
| 6,391,314 B1 | 5/2002 | Allan et al. |
| 6,455,245 B1 | 9/2002 | Wensvoort et al. |
| 6,495,138 B1 | 12/2002 | van Nieuwstadt et al. |
| 6,498,008 B2 | 12/2002 | Collins et al. |
| 6,500,662 B1 | 12/2002 | Calvert et al. |
| 6,592,873 B1 | 7/2003 | Paul et al. |
| 6,641,819 B2 | 11/2003 | Mengeling et al. |
| 6,660,513 B2 | 12/2003 | Mengeling et al. |
| 6,773,908 B1 | 8/2004 | Paul et al. |
| 6,806,086 B2 | 10/2004 | Wensvoort et al. |
| 6,841,364 B2 | 1/2005 | Yuan et al. |
| 6,855,315 B2 | 2/2005 | Collins et al. |
| 6,982,160 B2 | 1/2006 | Collins et al. |
| 7,018,638 B2 | 3/2006 | Chu et al. |
| 7,081,342 B2 | 7/2006 | Mengeling et al. |
| 7,109,025 B1 | 9/2006 | Eloit et al. |
| 7,122,347 B2 | 10/2006 | Verheije et al. |
| 7,132,106 B2 | 11/2006 | Calvert et al. |
| 7,169,394 B2 | 1/2007 | Chu et al. |
| 7,211,379 B2 | 5/2007 | Ellis et al. |
| 7,232,680 B2 | 6/2007 | Calvert et al. |
| 7,264,804 B2 | 9/2007 | Collins et al. |
| 7,273,617 B2 | 9/2007 | Yuan et al. |
| 7,312,030 B2 | 12/2007 | van Rijn et al. |
| 7,335,361 B2 | 2/2008 | Liao et al. |
| 7,335,473 B2 | 2/2008 | Wensvoort et al. |
| 7,368,117 B2 | 5/2008 | Fetzer et al. |
| 7,618,797 B2 | 11/2009 | Calvert et al. |
| 7,632,636 B2 | 12/2009 | Roof et al. |
| 7,691,389 B2 | 4/2010 | Calvert et al. |
| 7,722,878 B2 | 5/2010 | Vaughn et al. |
| 7,897,343 B2 | 3/2011 | Wensvoort et al. |
| 2002/0012670 A1 | 1/2002 | Elbers et al. |
| 2002/0098573 A1 | 7/2002 | Meulenberg et al. |
| 2002/0172690 A1 | 11/2002 | Calvert et al. |
| 2003/0049274 A1 | 3/2003 | Meulenberg et al. |
| 2003/0118608 A1 | 6/2003 | Wensvoort et al. |
| 2003/0157689 A1 | 8/2003 | Calvert et al. |
| 2003/0219732 A1 | 11/2003 | van Rijn et al. |
| 2004/0009190 A1 | 1/2004 | Elbers et al. |
| 2004/0132014 A1 | 7/2004 | Wensvoort et al. |
| 2004/0197872 A1 | 10/2004 | Meulenberg et al. |
| 2004/0213805 A1 | 10/2004 | Verheije |
| 2004/0224327 A1 | 11/2004 | Meulenberg et al. |
| 2004/0253270 A1 | 12/2004 | Meng et al. |
| 2006/0063151 A1 | 3/2006 | Roof et al. |
| 2006/0205033 A1 | 9/2006 | Meulenberg et al. |
| 2006/0240041 A1 | 10/2006 | Meulenberg et al. |
| 2006/0286123 A1 | 12/2006 | Fetzer et al. |
| 2007/0003570 A1 | 1/2007 | Murtaugh et al. |
| 2007/0042000 A1 | 2/2007 | Mengeling et al. |
| 2009/0148474 A1 | 6/2009 | Roof et al. |
| 2010/0003278 A1 | 1/2010 | Roof et al. |
| 2010/0028860 A1 | 2/2010 | Roof et al. |
| 2010/0129398 A1 | 5/2010 | Klinge et al. |
| 2011/0104201 A1 | 5/2011 | Mengeling et al. |
| 2011/0117129 A1 | 5/2011 | Roof et al. |
| 2011/0195088 A1 | 8/2011 | Roof et al. |
| 2012/0189655 A1 | 7/2012 | Wu et al. |
| 2013/0028931 A1 | 1/2013 | Gallei |
| 2013/0183329 A1 | 7/2013 | Zhang et al. |
| 2014/0314808 A1* | 10/2014 | Fetzer et al. ............ 424/204.1 |

FOREIGN PATENT DOCUMENTS

| | | |
|---|---|---|
| EP | 208672 A1 | 1/1987 |
| EP | 0440219 A1 | 8/1991 |
| EP | 0529584 A2 | 3/1993 |
| EP | 587780 A1 | 3/1994 |
| EP | 0595436 A2 | 5/1994 |
| EP | 0610250 A1 | 8/1994 |
| EP | 676467 A2 | 10/1995 |
| EP | 732340 A2 | 9/1996 |
| EP | 0835929 A1 | 4/1998 |
| EP | 0835930 A1 | 4/1998 |
| EP | 0839912 A1 | 5/1998 |
| EP | 1018557 A2 | 7/2000 |
| FR | 2602791 A1 | 2/1988 |
| GB | 2282811 A | 4/1995 |
| GB | 2289279 A | 11/1995 |
| JP | 62/198626 A | 9/1987 |
| WO | 8803410 A1 | 5/1988 |
| WO | 8908701 A1 | 9/1989 |
| WO | 9221375 A1 | 12/1992 |
| WO | 9303760 A1 | 3/1993 |
| WO | 9306211 A1 | 4/1993 |
| WO | 9307898 A1 | 4/1993 |
| WO | 9314196 A1 | 7/1993 |
| WO | 9418311 A1 | 8/1994 |
| WO | 9528227 A1 | 10/1995 |
| WO | 9531550 A1 | 11/1995 |
| WO | 9604010 A1 | 2/1996 |
| WO | 9606619 A1 | 3/1996 |
| WO | 9636356 A1 | 11/1996 |
| WO | 9640932 A1 | 12/1996 |
| WO | 9700696 A1 | 1/1997 |
| WO | 9731651 A1 | 9/1997 |
| WO | 9731652 A1 | 9/1997 |
| WO | 9818933 A1 | 5/1998 |
| WO | 9835023 A1 | 8/1998 |
| WO | 9850426 A1 | 11/1998 |
| WO | 9855625 A1 | 12/1998 |
| WO | 9855626 A2 | 12/1998 |
| WO | 0053787 A1 | 9/2000 |
| WO | 0065032 A1 | 11/2000 |
| WO | 0159077 A1 | 8/2001 |
| WO | 0190363 A1 | 11/2001 |
| WO | 02060921 A2 | 8/2002 |
| WO | 02095040 A1 | 11/2002 |
| WO | 03062407 A1 | 7/2003 |
| WO | 2006002193 A2 | 1/2006 |
| WO | 2006034319 A2 | 3/2006 |
| WO | 2006074986 A2 | 7/2006 |
| WO | 2007002321 A2 | 1/2007 |
| WO | 2007064742 A2 | 6/2007 |
| WO | 2008109237 A2 | 9/2008 |
| WO | 2008121958 A1 | 10/2008 |
| WO | 2010025109 A1 | 3/2010 |
| WO | 2011128415 A1 | 10/2011 |

OTHER PUBLICATIONS

"Revision of the taxonomy of the Coronavirus, Torovirus, and Arterivirus genera". Archives of Virology, vol. 135, 1994, pp. 227-239.

Abstracts of Papers Presented at the 71st Annual Meeting of the Conference of Research Workers in Animal Disease, Nos. 1-6, Nov. 5-6, 1990, 2 pages.

Aksenova et al., "Cultivation of the rabies virus in the continuous kidney cell line 4647 from the green marmoset". Vopr. Virusol., vol. 30, No. 2, 1985, pp. 180-182. (See AXENOVA for English Abstract).

Albina et al., "Immune responses in pigs infected with porcine reproductive and respiratory syndrome virus (PRRSV)". Veterinary Immunology and Immunopathology, vol. 61, 1998, pp. 49-66.

(56) References Cited

OTHER PUBLICATIONS

Allan et al., "Experimental infection of colostrum deprived piglets with porcine circovirus 2 (PCV2) and procine reproductive and respiratory syndrome virus (PRRSV) potentiates PCV2 replication". 2000, Archives of Virology, vol. 145, pp. 2421-2429.

Allende et al., "Mutations in the genome of porcine reproductive and respiratory syndrome virus responsible for the attenuated phenotype". Archives of Virology, vol. 145, No. 6, Jun. 2000, pp. 1149-1161.

Allende et al., "North American and European porcine reproductive and respiratory syndrome viruses differ in non-structural protein coding regions". Journal of General Virology, vol. 80, 1999, pp. 307-315.

Allende et al., "Porcine Reproductive and Respiratory Syndrome Virus: Description of Persistence in Individual Pigs upon Experimental Infection†". Journal of Virology, vol. 74, No. 22, Nov. 2000, pp. 10834-10837.

Altschul et al., "Basic Local Alignment Search Tool". Journal of Molecular Biology, vol. 215, 1990, pp. 403-410.

Andreyev et al., "Genetic variation and phylogenetic relationships of 22 porcine reproductive and respiratory syndrome virus (PRRSV) field strains based on sequence analysis of open reading frame 5". Archives of Virology, vol. 142, 1997, pp. 993-1001.

Ansari et al., "Influence of N-Linked Glycosylation of Porcine Reproductive and Respiratory Syndrome Virus GP5 on Virus Infectivity, Antigenicity, and Ability to Induce Neutralizing Antibodies." Journal of Virology, vol. 80, No. 8, Apr. 2006, pp. 3994-4004.

Ashworth et al., "Antibody-dependent cell-mediated cytotoxicity (ADCC) in Aujeszky's disease". Archives of Virology, vol. 59, No. 4, 1979, pp. 307-318.

Axenova, T.A. "Propagation of Rabies Vaccine Virus in Continuous Green Monkey Kidney Cells 4647". Vopr. Virusol., vol. 30, No. 2, 1985, p. 182. (English Abstract of AKSENOVA Reference.).

Backstrom et al., "Respiratory Diseases of Swine". Veterinary Clinics of North America: Large Animal Practice, vol. 4, No. 2, Nov. 1982, pp. 259-276.

Barfoed et al., "DNA vaccination of pigs with open reading frame 1-7 of PRRS virus". Vaccine, vol. 22, 2004, pp. 3628-3641.

Baric et al., "Interactions between Coronavirus Nucleocapsid Protein and Viral RNAs: Implications for Viral Transcription". Journal of Virology, vol. 62, No. 11, Nov. 1988, pp. 4280-4287.

Baric et al., "Subgenomic Negative-Strand RNA Function during Mouse Hepatitis Virus Infection". Journal of Virology, vol. 74, No. 9, May 2000, pp. 4039-4046.

Bautista et al., "Comparison of Porcine Alveolar Macrophages and CL 2621 for the Detection of Porcine Reproductive and Respiratory Syndrome (PRRS) Virus and Anti-PRRS Antibody". Journal of Veterinary Diagnostic Investigation, vol. 5, No. 2, Apr. 1993, pp. 163-165.

Bautista et al., "Serologic Survey for Lelystad and VR-2332 Strains of Porcine Respiratory and Reproductive Syndrome (PRRS) Virus in US Swine Herds". Journal of Veterinary Diagnostic Investigation, vol. 5, No. 4, Oct. 1992, pp. 612-614.

Beale, AJ, "Vaccines and antiviral drugs". Principles of bacteriology, virology and immunity, vol. 3, Ch. 86, 1984, pp. 147-161.

Beare et al., "Further Studies in Man of Man of HSw1N1 Influenza Viruses". Journal of Medical Virology, vol. 5, 1980, pp. 33-38.

Beghi et al., "Guillain-Barré Syndrome: Clinicoepidemiologic Features and Effect of Influenza Vaccine". Archives of Neurology, vol. 42, No. 11, 1985, pp. 1053-1057.

Benfield et al., "Characterization of swine infertility and respiratory syndrome (SIRS) virus (isolate ATCC VR-2332)". Journal of Veterinary Diagnostic Investigation, vol. 4, 1992, pp. 127-133.

Benfield et al., "Etiologic Agent of Swine Infertility and Respiratory Syndrome in the United States". 72st Annual Meeting of the Conference of Research Workers in Animal Disease, Chicago, IL, Nov. 11-12, 1991, p. 48, Abstract No. 268.

Benfield et al., "Properties of SIRS Virus Isolate ATCC VR-2332 in the United States and Preliminary Characterization of a Monoclonal Antibody to this Virus". American Association of Swine Practitioners Newsletter, vol. 4, No. 4, Jul./Aug. 1992, pp. 19-21.

Berendt et al., "Evaluation of Commercially Prepared Vaccines for Experimentally Induced Type/A/New Jersey/8/76 Influenza Virus Infections in Mice and Squirrel Monkeys". The Journal of Infectious Diseases, vol. 136, Dec. 1977, pp. S712-S718.

Berendt et al., "Reaction of Squirrel Monkeys to Intratracheal Inoculation with Influenza/A/New Jersey/76 (Swine) Virus". Infection and Immunity, vol. 16, No. 2, May 1977, pp. 476-479.

Beura et al., "Porcine Reproductive and Respiratory Syndrome Virus Nonstructural Protein 1β Modulates Host Innate Immune Response by Antagonizing IRF3 Activation". Journal of Virology, Volo. 84, No. 3, Feb. 2010, pp. 1574-1584.

Bilodeau et al., "'Porcine Reproductive and Respiratory Syndrome' in Quebec". The Veterinary Record, Aug. 3, 1991, p. 102.

Blackburn et al., "Use of human influenza vaccine to protect against blue-eared pig disease". Veterinary Record, vol. 129, No. 1, Jul. 1991, p. 19.

Bohl et al., "Isolation and Serotyping of Porcine Rotaviruses and Antigenic Comparison with Other Rotaviruses". Journal of Clinical Microbiology, vol. 19, No. 2, Feb. 1984, pp. 105-111.

Bouillant et al., "Viral Susceptibility of a Cell Line Derived from the Pig Oviduct". Canadian Journal of Comparative Medicine, vol. 39, 1975, pp. 450-456.

Boursnell et al., "Sequence of the membrane protein gene from avian coronavirus IBV". Virus Research, vol. 1, 1984, pp. 303-313.

Boursnell et all., "Completion of the Sequence of the Genome of the Coronavirus Avian Infectious Bronchitis Virus". Journal of General Virology, vol. 68, 1987, pp. 57-77.

Bowie et al., "Deciphering the Message of Protein Sequences: Tolerance to Amino Acid Substitutions". Science, vol. 247, 1990, pp. 1306-1310.

Boyer et al., "Infectious Transcripts and cDNA Clones of RNA Viruses". Virology, vol. 198, No. 2, Feb. 1994, pp. 415-426.

Bramel-Verheije et al., "Expression of a Foreign Epitope by Porcine Reproductive and Respiratory Syndrome Virus". Virology, vol. 278, 2000, pp. 380-389.

Bredenbeek et al., "The primary structure and expression of the second open reading frame of the polymerase gene of the coronavirus MHV-A59; a highly conserved polymerase is expressed by an efficient ribosomal frameshifting mechanism". Nucleic Acids Research, vol. 18, No. 7, 1990, pp. 1825-1832.

Brenner et al., "A Negative Staining Method for High Resolution Electron Microscopy of Viruses". Biochimica Et Biophysica Acta, vol. 34, 1959, pp. 103-110.

Brinton-Darnell et al., "Structure and chemical-physical characteristics of lactate dehydrogenase-elevating virus and its RNA". Journal of Virology, vol. 16, No. 2, Aug. 1975, pp. 420-433.

Brinton-Darnell, M. "Lactate Dehydrogenase-Elevating, Equine Arteritis and Lelystad Viruses". Encyclopedia of Virology, vol. 2, 1999, pp. 763-771.

Bruner, D.W., "Table XXXII. Characteristics of Viral Respiratory Infections in Swine" Hagan's Infectious Diseases of Domestic Animals: With Special Reference to Etiology, Diagnosis, and Biologic Therapy, Sixth Edition, Comstock Publishing Associations, a division of Cornell University Press, Ithaca and London, 1973, 5 pages.

Brüggemann et al., "Immunoglobulin V region variants in hybridoma cells. I. Isolation of a variant with altered idiotypic and antigen binding specificity". The EMBO Journal, vol. 1, No. 5, 1982, pp. 629-634.

Buck, K. W., "Comparison of the Replication of Positive-Stranded RNA Viruses of Plants and Animals". Advances in Virus Research, vol. 47, 1996, pp. 159-251.

Buddaert et al., "In Vivo and In Vitro Interferon (IFN) Studies with the Porcine Reproductive and Respiratory Syndrome Virus (PRRSV)". Coronaviruses and Arteriviruses: Advances in Experimental Medicine and Biology, vol. 440, Plenum Press, New York, 1998, pp. 461-467.

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue". The Journal of Cell Biology, vol. 111, 1990, pp. 2129-2138.

(56) References Cited

OTHER PUBLICATIONS

Burroughs, et al., "Relationship of San Miguel Sea Lion Virus to Other Members of the Calicivirus Group". Intervirology, vol. 10, 1978, pp. 51-59.
Cabasso et al., "Propagation of Infectious Canine Hepatitis Virus in Tissue Culture". Proceedings of the Society for Experimental Biology and Medicine, vol. 85, 1954, pp. 239-245.
Caeiro et al., "In vitro DNA replication by cytoplasmic extracts from cells infected with African swine fever virus". Virology, vol. 179, No. 1, Nov. 1990, pp. 87-94.
Callebaut et al., "Antigenic Differentiation between Transmissible Gastroenteritis Virus of Swine and a Related Porcine Respiratory Coronavirus". Journal of General Virology, vol. 69, 1988, pp. 1725-1730.
Cano et al., "Impact of a modified-live porcine reproductive and respiratory syndrome virus vaccine intervention on a population of pigs infected with a heterologous isolate". Vaccine, vol. 25, 2007, pp. 4382-4391.
Carrascosa et al., "Relationship of San Miguel Sea Lion Virus to Other Members of the Calicivirus Group". Journal of Virological Methods, vol. 3, No. 6, Jan. 1982, pp. 303-310.
Carvajal et al., "Evaluation of a Blocking ELISA Using Monoclonal Antibodies for the Detection of Porcine Epidemic Diarrhea Virus and Its Antibodies". Journal of Veterinary Diagnostic Investigation, vol. 7, No. 1, Jan. 1995, pp. 60-64.
Cavanagh, D., "Nidovirales: a new order comprising Coronaviridae and Arteriviridae". Archives of Virology, vol. 142, No. 3, 1997, pp. 629-633.
Chang et al., "A cis-Acting Function for the Coronavirus Leader in Defective Interfering RNA Replication". Journal of Virology, vol. 68, No. 12, Dec. 1994, pp. 8223-8231.
Chang et al., "Evolution of Porcine Reproductive and Respiratory Syndrome Virus during Sequential Passages in Pigs". Journal of Virology, vol. 76, No. 10, May 2002, pp. 4750-4763.
Chao et al., "Monoclonal Antibodies to Metacyclic Stage Antigens of Trypanosoma Cruzi" The American Journal of Tropical Medicine and Hygiene, vol. 34, No. 4, Jul. 1985, pp. 694-701.
Charley, B., "Interaction of influenza virus with swine alveolar macrophages: Influence of anti-virus antibodies and cytochalasin B". Annales de l'Instiut Pasteur. Virologie, vol. 134, No. 1, Jan. 1983, pp. 51-59.
Chasey et al., "Replication of Atypical Ovine Rotavirus in Small Intestine and Cell Culture". Journal of General Virology, vol. 67, No. 3, Mar. 1986, pp. 567-576.
Chen et al., "Identification of two auto-cleavage products of nonstructural protein 1 (nsp1) in porcine reproductive and respiratory syndrome virus infected cells: nsp1 function as interferon antagonist". Virology, vol. 398, 2010, pp. 87-97.
Chen et al., "Synthetic B- and T-cell epitope peptides of porcine reproductive and respiratory syndrome virus with Gp96 as adjuvant induced humoral and cell-mediated immunity". Vaccine, vol. 31, 2013,

(56) References Cited

OTHER PUBLICATIONS

Dea et al., "Antigenic Variability among North American and European Strains of Porcine Reproductive and Respiratory Syndrome Virus as Defined by Monoclonal Antibodies to the Matrix Protein". Journal of Clinical Microbiology, vol. 34, No. 5, Jun. 1996, pp. 1488-1493.
Dea et al., "Antigenic variant of swine influenza virus causing proliferative and necrotizing pneumonia in pigs". Journal of Veterinary Diagnostic Investigation, vol. 4, No, 4, 1992, pp. 380-392.
Dea et al., "Caracteristiques d'Isolats des virus influenza et de l'encephalomyocardite associes au Syndrome Reproducteur et Respiratoire Porcine (S.R.R.P.) au Quebec.sup.a," Le Medecin Veterinaire Du Quebec, vol. 21, No. 4, Nov. 1991, pp. 170-175.
Dea et al., "Current knowledge on the structural proteins of porcine reproductive and respiratory syndrome (PRRS) virus: comparison of the North American and European isolate". Archives of Virology, vol. 145, No. 4, Apr. 2000, pp. 659-688.
Dea et al., "Isolation of encephalomyocarditis virus among stillborn and post-weaning pigs in Quebec". Archives of Virology, vol. 117, Nos. 1-2, 1991, pp. 121-128.
Dea et al., "Swine reproductive and respiratory syndrome in Quebec: Isolation of an enveloped virus serologically-related to Lelystad virus". Canadian Veterinary Journal, vol. 33, No. 12, Dec. 1992, pp. 801-808.
Dea et al., "Virus Isolations from Farms in Quebec Experiencing Severe Outbreaks of Respiratory and Reproductive Problems". Proceedings of the Mystery Swine Disease Committee Meeting, Denver, CO, Oct. 6, 1990, pp. 67-72.
Del Val et al., "Glycosylated components of African swine fever virus particles". Virology, vol. 152, No. 1, Jul. 1986, pp. 39-49.
Den Boon et al., "Equine Arteritis Virus Is Not a Togavirus but Belongs to the Coronaviruslike Superfamily". Journal of Virology, vol. 65, No. 6, 1991, pp. 2910-2920.
Den Boon et al., "Processing and Evolution of the N-Terminal Region of the Arterivirus Replicase ORF1a Protein: Identification of Two Papainlike Cysteine Proteases". Journal of Virology, vol. 69, No. 7, Jul. 1995, pp. 4500-4505.
Guan et al., "Requirement of a 5?-Proximal Linear Sequence on Minus Strands for Plus-Strand Synthesis of a Satellite RNA Associated with Turnip Crinkle Virus". Virology, vol. 268, No. 2, Mar. 2000, pp. 355-363.
Gubler et al., "A simple and very efficient method for generating cDNA libraries". Gene, vol. 25, 1983, pp. 263-269.
Gustafson, D.P., "Pseudorabies". Diseases of Swine, Fifth Edition, Ch. 14, The Iowa State University Press, Ames, Iowa, 1981, pp. 209-223.
Halbur et al., "Comparative pathogenicity of nine US porcine reproductive and respiratory syndrome virus (PRRSV) isolates in a five-week-old cesarean-derived, colostrum-deprived pig model". Journal of Veterinary Diagnostic Investigation, vol. 8, 1996, pp. 11-20.
Halbur et al., "Effects of different US isolates of porcine reproductive and respiratory syndrome virus (PRRSV) on blood and bone marrow parameters of experimentally infected pigs". Veterinary Record, vol. 151, 2002, pp. 344-348.
Halbur et al., "Variable Pathogenicity of Nine Porcine Reproductive and Respiratory Syndrome Virus (PRRSV) Isolates". Conference of Research Workers in Animal Diseases, Abstracts of Papers, Chicago, Illinois, paper #222, Nov. 1993.
Halbur et al., "Viral Pneumonia in Neonatal and Nursery pigs. Experimental Work with SIRS Agent and Evidence of Another New Viral Agent". Agri-Practice, vol. 12, No. 1, Jan.-Feb. 1991, pp. 23-34.
Haller et al., "The Interferon Response Circuit in Antiviral Host Defense". Verh. K. Acad. Geneeskd. Belg., vol. 71, 2009, pp. 73-86.
Hao et al., "Polymorphic genetic characterization of the ORF7 gene of porcine reproductive and respiratory syndrome virus (PRRSV) in China". Virology Journal, vol. 8, No. 73, 2011, pp. 1-9.
Harlow & Lane, Editors, "Antibodies, A Laboratory Manual". Cold Spring Harbor: Cold Spring Harbor Laboratory, New York, 1988, pp. 423, 464-468.
Haynes et al., "Temporal and Morphologic Characterization of the Distribution of Porcine Reproductive and Respiratory Syndrome Virus (PRRSV) by In Situ Hybridization in Pigs Infected with Isolates of PRRSV that Differ in Virulence". Veterinary Pathology, vol. 34, 1997, pp. 39-43.
Heath, et al., "The Behaviour of Some Influenza Viruses in Tissue Cultures of Kidney Cells of Various Species". Archiv. f. Virusforschung Bd. VIII, HS, 1958, pp. 577-591.
Hedger et al., "Swine Vesicular Disease Virus". Virus Infections of Porcines, Elsevier Science Publishers, B.V., 1989, pp. 241-250.
Hennen, J., "Statistical methods for longitudinal research on bipolar disorders". Bipolar Disorders, vol. 5, 2003, pp. 156-168.
Hill, Howard, "Overview and History of Mystery Swine". Proceedings of the Mystery Swine Disease Committee Meeting, Denver, CO, Oct. 6, 1990, pp. 29-40.
Hirsch et al., "Ultrastructure of Human Leukocytes After Simultaneous Fixation with Glutaraldehyde and Osmium Tetroxide and "Postfixation" in Uranyl Acetate". The Journal of Cell Biology, vol. 38, 1968, pp. 615-627.
Hofmann et al., "Propagation of the virus of porcine epidemic diarrhea in cell culture". Journal of Clinical Microbiology, vol. 26, No. 11, Nov. 1988, pp. 2235-2239.
Hofmann et al., "Quantitation, biological and physicochemical properties of cell culture-adapted porcine epidemic diarrhea coronavirus (PEDV)". Veterinary Microbiology, vol. 20, No. 2, Jun. 1989, pp. 131-142.
Honda et al., "A Serological Comparison of 4 Japanese Isolates of Porcine Enteroviruses with the International Reference Strains". The Japanese Journal of Veterinary Science, vol. 52, No. 1, 1990, pp. 49-54.
Horowitz et al., "Anti-schistosome monoclonal antibodies of different isotypes—correlation with cytotoxicity". The EMBO Journal, vol. 2, No. 2, 1983, pp. 193-198.
Horsfall et al., "General Principles of Animal Virus Multiplication". Viral and Rickettsial Infections of Man, Fourth Edition, J.B. Lippincott Company, Philadelphia, 1965, pp. 239-241.
Horzinek et al., "Studies on the Substructure of Togaviruses: II. Analysis of Equine Arteritis Rubella, Bovine Viral Diarrhea, and Hog Cholera Viruses". Archiv Fir die gesamte Virusforschung, vol. 33, 1971, pp. 306-318.
Hoshino et al., "Isolation and characterization of an equine rotavirus". Journal of Clinical Microbiology, vol. 18, No. 3, Sep. 1983, pp. 585-591.
Hoshino et al., "Serotypic Similarity and Diversity of Rotaviruses of Mammalian and Avian Origin as Studied by Plaque-Reduction Neutralization". The Journal of Infectious Diseases, vol. 149, No. 5, May 1984, pp. 694-702.
Hsue et al., "Characterization of an Essential RNA Secondary Structure in the 3' Untranslated Region of the Murine Coronavirus Genome". Journal of Virology, vol. 74, No. 15, Aug. 2000, pp. 6911-6921.
Huang et al., "Polypyrimidine Tract-Binding Protein Binds to the Complementary Strand of the Mouse Hepatitis Virus 39 Untranslated Region, Thereby Altering RNA Conformation". Journal of Virology, vol. 73, No. 11, Nov. 1999, pp. 9110-9116.
Hurrelbrink et al., "Attenuation of Murray Valley Encephalitis Virus by Site-Directed Mutagenesis of the Hinge and Putative Receptor-Binding Regions of the Envelope Protein". Journal of Virology, vol. 75, No. 16, Aug. 2001, pp. 7692-7702.
Hwang et al., "A 68-Nucleotide Sequence within the 39 Noncoding Region of Simian Hemorrhagic Fever Virus Negative-Strand RNA Binds to Four MA104 Cell Proteins". Journal of Virology, vol. 72, No. 5, May 1998, pp. 4341-4351.
Hyllseth, B., "Structural Proteins of Equine Arteritis Virus". Archiv Für die gesamte Virusforschung, vol. 30, 1973, pp. 177-188.
Iltis et al., "Persistent Varicella-Zoster virus infection in a human rhabdomyosarcoma cell line and recovery of a plaque variant". Infection and Immunity, vol. 37, No. 1, Jul. 1982, pp. 350-358.
Imagawa et al., "Isolation of Foal Rotavirus in MA-104 Cells". Bulleting of Equine Research Institute, vol. 18, 1981, pp. 119-128.
International Search Report and Written Opinion for PCT/EP2012/064888 mailed Oct. 30, 2012.

(56) References Cited

OTHER PUBLICATIONS

Izeta et al., "Replication and Packaging of Transmissible Gastroenteritis Coronavirus-Derived Synthetic Minigenomes". Journal of Virology, vol. 73, No. 2, Feb. 1999, pp. 1535-1545.
Jackwood et al., "Replication of Infectious Bursal Disease Virus in Continuous Cell Lines". Avian Diseases, vol. 31, No. 2, Apr.-Jun. 1987, pp. 370-375.
Johnson et al., "Feline panleucopaenia virus. IV. Methods for obtaining reproducible in vitro results". Research in Veterinary Science, vol. 8, No. 2, Apr. 1967, pp. 256-264.
Johnson et al., "Pathogenic and humoral immune responses to porcine reproductive and respiratory syndrome virus (PRRSV) are related to viral load in acute infection". Veterinary Immunology and Immunopathology, vol. 102, No. 3, PRRS Immunology and Immunopathology Special Issue, Dec. 2004, pp. 233-247.
Johnston et al., "Genetic to genomic vaccination". Vaccine, vol. 15, No. 8, 1997, pp. 808-809.
Joo et al., "Encephalomyocarditis Virus as a Potential Cause for Mystery Swine Disease", Livestock Conservation Institute, Proceedings of the Mystery Swine Disease Committee Meeting, Denver, CO, Oct. 6, 1990, pp. 62-66.
Jun et al., "Comparison of Dynamics in Viremia Levels in Chickens Inoculated with Marek's Disease Virus Strains of Different Pathotypes". Virologica Sinica, vol. 16, No. 1, Mar. 2001, pp. 59-63.
Jusa et al., "Effect of heparin on infection of cells by porcine reproductive and respiratory syndrome virus". American Journal of Veterinary Research, vol. 58, No. 5, May 1997, pp. 488-491.
Just et al., "A/New Jersey/76 influenza vaccine trial in seronegative schoolchildren: Comparison of a subunit vaccine with a whole-virus vaccine". Medical Microbiology and Immunology, vol. 164, No. 4, 1978, pp. 277-284.
Kang et al., "Primary Isolation and Identification of Avian Rotaviruses from Turkeys Exhibiting Signs of Clinical Enteritis in a Continuous MA-104 Cell Line". Avian Diseases, vol. 30, 1986, pp. 494-499.
Kapur et al., "Genetic variation in porcine reproductive and respiratory syndrome virus isolates in the midwestern United States". Journal of General Virology, vol. 77, 1996, pp. 1271-1276.
Kasza et al., "Establishment, viral susceptibility and biological characteristics of a swine kidney cell line SK-6". Research in Veterinary Science, vol. 13, No. 1, Jan. 1972, pp. 46-51.
Kasza et al., "Isolation and Characterization of a Rotavirus from Pits". Veterinary Record, vol. 87, 1970, pp. 681-686.
Katz et al., "Antigenic differences between European and American isolates of porcine reproductive and respiratory syndrome virus (PRRSV) are encoded by the carboxyterminal portion of viral open reading frame 3". Veterinary Microbiology, vol. 44, No. 1, Apr. 1995, pp. 65-76.
Keffaber, K., "Reproductive Failure of Unknown Etiology"., AASP Newsletter, vol. 1, No. 2, Sep.-Oct. 1989, pp. 1, 4-5, 8-10.
Keffaber, K.K., "Swine Reproductive Failure of Unknown Etiology". The George A. Young Swine Conference & Annual Nebraska SPF Swine Conference, Aug. 13-14, 1990, pp. 55-67.
Key et al., "Genetic variation and phylogenetic analyses of the ORF5 gene of acute porcine reproductive and respiratory syndrome virus isolates". Veterinary Microbiology, vol. 83, 2001, pp. 249-263.
Kim et al., "Analysis of cis-Acting Sequences Essential for Coronavirus Defective Interfering RNA Replication". Virology, vol. 197, No. 1, Nov. 1993, pp. 53-63.
Kim et al., "Different Biological Characteristics of Wild-Type Porcine Reproductive and Respiratory Syndrome Viruses and Vaccine Viruses and Identification of the Corresponding Genetic Determinants". Journal of Clinical Microbiology, vol. 46, No. 5, May 2008, pp. 1758-1768.
Kim et al., "Enhanced replication of porcine reproductive and respiratory syndrome (PRRS) virus in a homogeneous subpopulation of MA-104 cell line". Archives of Virology, vol. 133, 1993, pp. 477-483.
Kim et al., "Modulation of type I interferon induction by porcine reproductive and respiratory syndrome virus and degradation of CREB-binding protein by non-structural protein 1 in MARC-145 and HeLa cells". Virology, vol. 402, 2010, pp. 315-326.
Kimman et al., "Challenges for porcine reproductive and respiratory syndrome virus (PRRSV) vaccinology". Vaccine, vol. 27, No. 28, Jun. 2009, pp. 3704-3718.
Klein et al., "Deletion of the IgH enhancer does not reduce immunoglobulin heavy chain production of a hybridoma IgD class switch variant". The EMBO Journal, vol. 3, No. 11, Nov. 1984, pp. 2473-2476.
Klinge et al, "Age-dependent resistance to Porcine reproductive and respiratory syndrome virus replication in swine". Virology Journal, vol. 6, No. 177, Oct. 2009.
Klinge et al., "PRRSV replication and subsequent immune responses in swine of various ages". Abstract of Poster No. 56, International Porcine Reproductive and Respiratory Syndrome (PRRS) Symposium, PRRS and PRRSV-Related Diseases: Prevention and Control Strategies, Chicago, IL, Nov. 30-Dec. 1, 2007.
Klovins et al., "A Long-range Pseudoknot in Qb RNA is Essential for Replication". Journal of Molecular Biology, vol. 294, 1999, pp. 875-884.
Klump et al., "Complete Nucleotide Sequence of Infectious Coxsackievirus B3 cDNA: Two Initial 5' Uridine Residues Are Regained during Plus-Strand RNA Synthesis". Journal of Virology, vol. 64, No. 4, Apr. 1990, pp. 1573-1583.
Klupp et al., "Sequence and expression of the glycoprotein gH gene of pseudorabies virus". Virology, vol. 182, No. 2, Jun. 1991, pp. 732-741.
Knowles et al., "Classification of porcine enteroviruses by antigenic analysis and cytopathic effects in tissue culture: Description of 3 new serotypes". Archives of Virology, vol. 62, No. 3, 1979, pp. 201-208.
Kolodziej et al., "Epitope tagging and protein surveillance". Methods in Enzymology, vol. 194, 1991, pp. 508-519.
Kouvelos et al., "Comparison of Bovine, Simian and Human Rotavirus Structural Glycoproteins". Journal of General Virology, vol. 65, Jul. 1984, pp. 1211-1214.
Kreutz, L.C., "Cellular membrane factors are the major determinants of porcine reproductive and respiratory syndrome virus tropism". Virus Research, vol. 53, 1998, pp. 121-128.
Kroese et al., "The nsp1a and nsp1b papain-like autoproteinases are essential for porcine reproductive and respiratory syndrome virus RNA synthesis". Journal of General Virology, vol. 89, 2008, pp. 494-499.
Kundin, W.D., "Hong Kong A-2 Influenza Virus Infection among Swine during a Human Epidemic in Taiwan". Nature, vol. 228, Nov. 1970, p. 857.
Kuo et al., "A Nested Set of Eight RNAs is Formed in Macrophages Infected with Lactate Dehydrogenase-Elevating Virus", Journal of Virology, vol. 65, No. 9, Sep. 1991, pp. 5118-5123.
Kusanagi et al., "Isolation and Serial Propagation of Porcine Epidemic Diarrhea Virus in Cell Cultures and Partial Characterization of the Isolate". Journal of Veterinary Medical Science, vol. 54, No. 2, 1992, pp. 313-318.
Kutsuzawa et al., "Isolation of Human Rotavirus Subgroups 1 and 2 in Cell Culture". Journal of Clinical Microbiology, vol. 16, No. 4, Oct. 1982, pp. 727-730.
Kwang et al., "Cloning, expression, and sequence analysis of the ORF4 gene of the porcine reproductive and respiratory syndrome virus MN-1b". Journal of Veterinary Diagnostic Investigation, vol. 6, No. 3, Jul. 1994, pp. 293-296.
Labarque et al., "Effect of cellular changes and onset of humoral immunity on the replication of porcine reproductive and respiratory syndrome virus in the lungs of pigs". Journal of General Virology, vol. 81, 2000, pp. 1327-1334.
Labarque et al., "Respiratory tract protection upon challenge of pigs vaccinated with attenuated porcine reproductive and respiratory syndrome virus vaccines". Veterinary Microbiology, vol. 95, 2003, pp. 187-197.
Lai et al., "Coronavirus: how a large RNA viral genome is replicated and transcribed". Infectious Agents and Disease, vol. 3, Nos. 2-3, 1994, pp. 98-105.
Lai et al., "Coronavirus: organization, replication and expression of genome". Annual Review of Microbiology, vol. 33, 1990, pp. 303-333.

(56) References Cited

OTHER PUBLICATIONS

Lai et al., "Infectious RNA transcribed from stably cloned full-length cDNA of dengue type 4 virus". Proceedings of the National Academy of Sciences, vol. 88, Jun. 1991, pp. 5139-5143.

Lazar et al., "Transforming Growth Factor a: Mutation of Aspartic Acid 47 and Leucine 48 Results in Different Biological Activities". Molecular and Cellular Biology, vol. 8, No. 3, Marc. 1988, pp. 1247-1252.

Leitner et al., "DNA and RNA-based vaccines: principles, progress and prospects". Vaccine, vol. 18, 2000, pp. 765-777.

Levy et al., "Freeze-drying is an effective method for preserving infectious type C retroviruses". Journal of Virological Methods, vol. 5, Nos. 3-4, Nov. 1982, pp. 165-171.

Li et al., "The cysteine protease domain of porcine reproductive and respiratory syndrome virus non-structural protein 2 antagonizes interferon regulatory factor 3 activation". Journal of General Virology, vol. 91, 2010, pp. 2947-2958.

Liljestrom et al., "A New Generation of Animal Cell Expression Vectors Based on the Semliki Forest Virus Replicon". Nature Biotechnology, vol. 9, 1991, pp. 1356-1361.

Lin et al., "Deletion Mapping of a Mouse Hepatitis Virus Defective Interfering RNA Reveals the Requirement of an Internal and Discontiguous Sequence fro Replication". Journal of Virology, vol. 67, No. 10, Oct. 1993, pp. 6110-6118.

Lin et al., "Identification of the cis-Acting Signal for Minus-Strand RNA Synthesis of a Murine Coronavirus: Implications for the Role of Minus-Strand RNA in RNA Replication and Transcription". Journal of Virology, vol. 68, No. 12, Dec. 1994, pp. 8131-8140.

Lin et al., "The 3' Untranslated Region of Coronavirus RNA is Required for Subgenomic mRNA Transcription from a Defective Interfering RNA". Journal of Virology, vol. 70, No. 10, Oct. 1995, pp. 7236-7240.

Liu et al., "A Specific Host Cellular Protein Binding Element Near the 3? End of Mouse Hepatitis Virus Genomic RNA". Virology, vol. 232, No. 1, May 1997, pp. 74-85.

Lopez et al., "Role of neutralizing antibodies in PRRSV protective immunity". Veterinary Immunology and Immunopathology, vol. 102, 2004, pp. 155-163.

Loula, T., "Clinical Presentation of Mystery Pig Disease in the Breeding Herd and Suckling Piglets". Proceedings of the Mystery Swine Disease Committee Meeting, Denver, CO, Oct. 6, 1990, pp. 37-40.

Loula, T., "Mystery Pig Disease", Agri-Practice, vol. 12, No. 1, Jan.-Feb. 1991, pp. 29-34.

Luo et al., "Antiviral activity of type I and type III interferons against porcine reproductive and respiratory syndrome virus (PRRSV)". Antiviral Research, vol. 91, 2011, pp. 91-101.

Luytjes et al., "Replication of Synthetic Defective Interfering RNAs Derived from Coronavirus Mouse Hepatitis Virus-A59". Virology, vol. 216, No. 1, Feb. 1996, pp. 174-183.

Lv et al., "An infectious cDNA clone of a highly pathogenic porcine reproductive and respiratory syndrome virus variant associated with porcine high fever syndrome". Journal of General Virology, vol. 89, 2008, pp. 2075-2079.

Madec et al., "Consequences pathologiques d'un episode grippal severe (virus swine A/H1N1 dans les conditions naturelles chez la truie non immune en debut de gestation". Comparative Immunology, Microbiology and Infectious Diseases, vol. 12, Nos. 1-2, 1989, pp. 17-27.

Madin, S.H. "Vesicular Exanthema Virus". Virus Infections of Porcines, Elsevier Science Publishers B.V., 1989, pp. 267-271.

Makabe et al., "Hemagglutination with Ovine Rotavirus". Archives of Virology, vol. 90, 1986, pp. 153-158.

Makino et al., "Leader sequences of murine coronavirus mRNAs can be freely reassorted: Evidence for the role of free leader RNA in transcription". Proceedings of the National Academy of Sciences, vol. 83, Jun. 1986, pp. 4204-4208.

Makino et al., "Primary Structure and Translation of a Defective Interfering RNA of Murine Coronavirus". Virology, vol. 166, 1988, pp. 550-560.

Mardassi et al., "Identification of major differences in the nucleocapsid protein genes of a Québec strain and European strains of porcine reproductive and respiratory syndrome virus". vol. 75, No. 3, Mar. 1994, pp. 681-685.

Mardassi et al., "Molecular analysis of the ORFs 3 to 7 of porcine reproductive and respiratory syndrome virus, Québec reference strain". Archives of Virology, vol. 140, No. 8, 1995, pp. 1405-1418.

Mardassi et al., "Structural Gene Analysis of a Quebec Reference Strain of Porcine Reproductive and Respiratory Syndrome Virus (PRRSV)". Corona- and Related Viruses, Edited by P.J. Talbot and G.A. Levy, Plenum Press, New York, 1995, pp. 277-281.

Mason, P.W., "Maturation of Japanese encephalitis virus glycoproteins produced by infected mammalian and mosquito cells". Virology, vol. 169, No. 2, Apr. 1989, pp. 354-364.

Masters et al., "Functions of the coronavirus nucleocapsid protein". Coronaviruses and Their Diseases, Plenum Press, New York, 1990, pp. 235-238.

Skiadopoulos et al., "Identification of Mutations Contributing to the Temperature-Sensitive, Cold-Adapted, and Attenuation Phenotypes of the Live-Attenuated Cold-Passage 45 (cp45) Human Parainfluenza Virus 3 Candidate Vaccine". Journal of Virology, vol. 73, No. 2, Feb. 1999, pp. 1374-1381.

Smith et al., "Isolation of Swine Influenza Virus from Autopsy Lung Tissue of Man". New England Journal of Medicine, vol. 294, Mar. 1976, pp. 708-710.

Smith et al., "San Miguel Sea Lion Virus Isolation, Preliminary Characterization and Relationship to Vesicular Exanthema of Swine Virus". Nature, vol. 244, Jul. 1973, pp. 108-110.

Snijder et al., "A 3'-Coterminal Nested Set of Independently Transcribed mRNAs Is Generated during Berne Virus Replication". Journal of Virology, vol. 64, No. 1, Jan. 1990, pp. 331-338.

Snijder et al., "Identification of a Novel Structural Protein of Arteriviruses". Journal of Virology, vol. 73, No. 8, Aug. 1999, pp. 6335-6345.

Snijder et al., "Non-structural proteins 2 and 3 interact to modify host cell membranes during the formation of the arterivirus replication complex". Journal of General Virology, vol. 83, 2001, pp. 985-994.

Snijder et al., "Proteolytic Processing of the Replicase ORF1a Protein of Equine Arteritis Virus". Journal of Virology, vol. 68, No. 9, Sep. 1994, pp. 5755-5764.

Snijder et al., "The carboxyl-terminal part of the putative Berne virus polymerase is expressed by ribosomal frameshifting and contains sequence motifs which indicate that toro- and coronaviruses are evolutionarily related". Nucleic Acids Research, vol. 18, No. 15, Aug. 1990, pp. 4535-4542.

Snijder et al., "The molecular biology of arteriviruses". Journal of General Virology, vol. 79, 1998, pp. 961-979.

Snijder et al., "Toroviruses: replication, evolution and comparison with other members of the coronavirus-like superfamily". Journal of General Virology, vol. 74, 1993, pp. 2305-2316.

Song et al., "Nonstructural protein 1? subunit-based inhibition of NF-?B activation and suppression of interferon-? production by porcine reproductive and respiratory syndrome virus". Virology, vol. 407, 2010, pp. 268-280.

Spaan et al., "Coronaviruses: Structure and Genome Expression". Journal of General Virology, vol. 69, 1988, pp. 2939-2952.

Stephen et al., "Swine Influenza Virus Vaccine: Potentiation in Rhesus Monkeys in Antibody Responses by a Nuclease Resistant Derivative of Ply I-Poly C". U.S. Army Medical Research Institute of Infectious Diseases, Fort Detrick, Frederick, MD 21701, 1976, 10 pages.

Stephen et al., "Swine influenza virus vaccine: potentiation of antibody responses in rhesus monkeys". Science, vol. 197, No. 4310, 1977, pp. 1289-1290.

Stevenson et al., "Endemic Porcine Reproductive and Respiratory Syndrome Virus Infection of Nursery Pigs in Two Swine Herds without Current Reproductive Failure". Journal of Veterinary Diagnostic Investigation, vol. 5, 1993, pp. 432-434.

Stim, T.B., "Arbovirus Plaquing in Two Simian Kidney Cell Lines". Journal of General Virology, vol. 5, No. 3, Oct. 1969, pp. 329-338.

(56) References Cited

OTHER PUBLICATIONS

Suarez et al., "Direct detection of the porcine reproductive and respiratory syndrome (PRRS) virus by reverse polymerase chain reaction (RT-PCR)". Archives of Virology, vol. 135, No. 1-2, 1994, pp. 89-99.
Suarez et al., "Phylogenetic relationships of European strains of porcine reproductive and respiratory syndrome virus (PRRSV) inferred from DNA sequences of putative ORF-5 and ORF-7 genes". Virus Research, vol. 42, Nos. 1-2, Jun. 1996, pp. 159-165.
Sumiyoshi et al., "Infectious Japanese Encephalitis Virus RNA Can Be Synthesized from In Vitro-Ligated cDNA Templates". Journal of Virology, vol. 66, No. 9, Sep. 1992, pp. 5425-5431.
Sun et al., "Crystal Structure of Porcine Reproductive and Respiratory Syndrome Virus Leader Protease Nsp1αÑ". Journal of Virology, vol. 83, No. 21, Nov. 2009, pp. 10931-10940.
Tahara et al., "Coronavirus Translational Regulation: Leader Affects mRNA Efficiency". Virology, vol. 202, No. 1, Aug. 1994, pp. 621-630.
Tao et al., "Host Range Restriction of Parainfluenza Virus Growth Occurs at the Level of Virus Genome Replication". Virology, vol. 220, 1996, pp. 69-77.
Tauraso et al., "Simian Hemorrhagic Fever: III. Characterization of a Viral Agent". The American Journal of Tropical Medicine and Hygiene, vol. 17, No. 3, May 1968, pp. 422-431.
Terpstra et al., "Experimental reproduction of porcine epidemic abortion and respiratory syndrome (mystery swine disease) by infection with Lelystad virus: Koch's postulates fulfilled". The Veterinary Quarterly, vol. 13, No. 3, Jul. 1991, pp. 131-136.
Thacker, B., "Clinical Manifestations of PRRS Virus". 2003 PRRS Compendium: Second Edition, National Pork Board, Des Moines, IA, 2003, pp. 7-15.
Thanawongnuwech et al., "Effects of Low (Modified-live Virus Vaccine) and High (VR-2385)-Virulence Strains of Porcine Reproductive and Respiratory Syndrome Virus on Pulmonary Clearance of Copper Particles in Pigs". Veterinary Pathology, vol. 35, 1998, pp. 398-406.
Theil et al., "Isolation and Serial Propagation of Turkey Rotaviruses in a Fetal Rhesus Monkey Kidney (MA104) Cell Line". Avian Diseases, vol. 30, No. 1, 1985, pp. 93-104.
Theil et al., "Partial characterization of a bovine group A rotavirus with a short genome electropherotype". Journal of Clinical Microbiology, vol. 26, No. 6, Jun. 1988, p. 1094-1099.
Thomson et al., "Ontario. Proliferative and necrotizing pneumonia (PNP) of swine: the Ontario situation". Canadian Veterinary Journal, vol. 32, May 1991, p. 313.
Thouless et al., "Isolation of two lapine rotaviruses: Characterization of their subgroup, serotype and RNA electropherotypes". Archives of Virology, vol. 89, Nos. 1-4, 1986, pp. 161-170.
Tian et al., "Emergence of Fatal PRRSV Variants: Unparalleled Outbreaks of Atypical PRRS in China and Molecular Dissection of the Unique Hallmark". PLoS One, vol. 2, No. 6, e526, 2007, pp. 1-10.
Timony, P.J. "Equine Viral Arteritis", Manual of Standards for Diagnostic Tests and Vaccines, 1992, pp. 493-500.
Tobita et al., "Plaque Assay and Primary Isolation of influenza A Viruses in an Established Line of Canine Kidney Cells (MDCK) in the Presence of Trypsin". Medical Microbiology and Immunology, vol. 162, No. 1, Dec. 1975, pp. 9-14.
Todd et al., "Development of an adjuvant-active nonionic block copolymer for use in oil-free subunit vaccines formulations". Vaccine, vol. 15, No. 5, 1997, pp. 564-570.
Travassos et al., "Carajas and Maraba Viruses, Two New Vesiculoviruses Isolated from Phlebotomine Sand Flies in Brazil". American Journal of Tropical Medicine and Hygiene, vol. 33, No. 5, Sep. 1984, pp. 999-1006.
Tsunemitsu et al., "Isolation, characterization, and serial propagation of a bovine group C rotavirus in a monkey kidney cell line (MA104)". Journal of Clinical Microbiology, vol. 29, No. 11, Nov. 1991, pp. 2609-2613.
Ulmer et al., "Enhancement of DNA vaccine potency using conventional aluminum adjuvants". Vaccine, vol. 18, 2000, pp. 18-28.
UniProt: Accession No. C9E449. "SubName: Full=M protein; SubName: Full= Membrane protein". Nov. 3, 2009.
UniProt: Accession No. D0VEE4. "SubName: Full=Unglycosylated membrane protein". Dec. 15, 2009.
UniProt: Accession No. Q6TLB4. "SubName: Full= Membrane protein M". Jul. 5, 2004.
Urasawa et al., "Sequential Passages of Human Rotavirus in MA-104 Cells". Microbiology and Immunology, vol. 25, No. 10, 1981, pp. 1025-1035.
Van Alstine, W.G., "Mystery Swine Disease in the United States". The New Pig Disease: Porcine Respiration and Reproductive Syndrome. A Report on the Seminar/Workshop Held in Brussels by the European Commission (Directorate—General for Agriculture), Apr. 29-30, 1991, pp. 65-70.
Van Alstine, W.G., "Past Diagnostic Approaches and Findings and Potentially Useful Diagnostic Strategies". Proceedings Mystery Swine Disease Committee Meeting, Oct. 6, 1990, pp. 52-58.
Van Berlo et al., "Equine Arteritis Virus-Infected Cells Contain Six Polyadenylated Virus-Specific RNAs". Virology, vol. 118, 1982, pp. 345-352.
Van Der Linden et al., "Virological kinetics and immunological responses to a porcine reproductive and respiratory syndrome virus infection of pigs at different ages". Vaccine, vol. 21, 2003, pp. 1952-1957.
Van Der Meer et al., "ORF1a-Encoded Replicase Subunits Are Involved in the Membrane Association of the Arterivirus Replication Complex". Journal of Virology, vol. 72, No. 8, 1998, pp. 6689-6698.
Van Der Most et al., "A Domain at the 3' End of the Polymerase Gene is Essential for Encapsidation of Coronavirus Defective Interfering RNAs". Journal of Virology, vol. 65, No. 6, Jun. 1991, pp. 3219-3226.
Van Dinten et al., "An infectious arterivirus cDNA clone: Identification of a replicase point mutation that abolished discontinuous mRNA transcription". Proceedings of the National Academy of Sciences, vol. 94, Feb. 1997, pp. 997-996.
Van Dinten et al., "Processing of the Equine Arteritis Virus Replicase ORF1b Protein: Identification of Cleavage Products Containing the Putative Viral Polymerase and Helicase Domains". Journal of Virology, vol. 70, No. 10, Oct. 1996, pp. 6625-6633.
Van Dinten et al., "Proteolytic Processing of the Open Reading Frame 1b-Encoded Part of Arterivirus Replicase is Mediated by nsp4 Serine Protease and is Essential for Virus Replication". Journal of Virology, vol. 73, No. 3, Mar. 1999, pp. 2027-2037.
Masurel, N., "Swine Influenza Virus and the Recycling of Influenza—A Viruses in Man". The Lancet, Jul. 31, 1976, pp. 244-247.
Matanin et al., "Purification of the major envelop protein GP5 of porcine reproductive and respiratory syndrome virus (PRRSV) from native virions". Journal of Virological Methods, vol. 147, 2008, pp. 127-135.
McAuliffe et al., "Codon Substitution Mutations at Two Positions in the L Polymerase Protein of Human Parainfluenza Virus Type 1 Yield Viruses with a Spectrum of Attenuation in Vivo and Increased Phenotypic Stability In Vitro". Journal of Virology, vol. 78, No. 4, Feb. 2004, pp. 2029-2036.
McCullough et al., "9. Experimental Transmission of Mystery Swine Disease", The New Pig Disease Porcine Respiration and Reproductive Syndrome, A report on the seminar/workshop held in Brussels on Apr. 29-30, 1991, pp. 46-52.
McDaniel, H.A., "African Swine Fever". Diseases of Swine, 5th Edition, Chapter 18, The Iowa State University Press, Ames, Iowa, 1981, pp. 237-245.
McFerran, J.B., "Reovirus Infection". Diseases of Swine, Fifth Edition, Chapter 28, The Iowa State University Press, Ames, Iowa, 1981, pp. 330-334.
McIntosh, "Diagnostic Virology". Fields Virology, Ch. 17, Second Edition, vol. 1, 1990, pp. 411-437.
McKinney, W.P., "Fatal Swine Influenza Pneumonia During Late Pregnancy". Archives of Internal Medicine, vol. 150, No. 1, Jan. 1990, pp. 213-215.
McQueen et al., "Influenza in animals". Advances in Veterinary Science, vol. 12, 1968, pp. 285-336.
Meier et al., "Gradual development of the interferon-g response of swine to porcine reproductive and respiratory syndrome virus infection or vaccination". Virology, vol. 309, 2003, pp. 18-31.

(56) References Cited

OTHER PUBLICATIONS

Meikeljohn et al., "Respiratory Virus Vaccine Evaluation and Surveillance". Semi-Annual Contract Progress Report to the National Institute of Allergy and Infectious Diseases, Sep. 15, 1965 to Mar. 15, 1966, 21 pgs.
Melchers et al., "Cross-talk between orientation-dependent recognition determinants of a complex control RNA element, the enterovirus oriR". RNA, vol. 6, 2000, pp. 976-987.
Mendez et al., "Molecular Characterization of Transmissible Gastroenteritis Coronavirus Defective Interfering Genomes: Packaging and Heterogeneity". Virology, vol. 217, 1996, pp. 495-507.
Meng et al., "Characterization of a High-Virulence US Isolate of Porcine Reproductive and Respiratory Syndrome Virus in a Continuous Cell Line, ATCC CRL11171". Journal of Veterinary Diagnostic Investigation, vol. 8, No. 3, Jul. 1996, pp. 374-381.
Meng et al., "Molecular cloning and nucleotide sequencing of the 3'-terminal genomic RNA of the porcine reproductive and respiratory syndrome virus". Journal of General Virology, vol. 75, 1994, pp. 1795-1801.
Meng et al., "Phylogenetic analyses of the putative M (ORF 6) and N (ORF 7) genes of porcine reproductive and respiratory syndrome virus (PRRSV): implication for the existence of two genotypes of PRRSV in the U.S.A and Europe". Archives of Virology, vol. 140, No. 4, 1995, pp. 745-755.
Meng, X.J., "Heterogeneity of porcine reproductive and respiratory syndrome virus: implications for current vaccine efficacy and future vaccine development". Veterinary Microbiology, vol. 74, 2000, pp. 309-329.
Mengeling et al., "An update of research at the National Animal Disease Center on current field strains of Porcine Reproductive and Respiratory Syndrome (PRRS) virus". Allen D. Leman Swine Conference, 1997, pp. 138-145.
Mengeling et al., "Clinical consequences of exposing pregnant gilts to strains of porcine reproductive and respiratory syndrome (PRRS) virus isolated from field cases of "atypical" PRRS". American Journal of Veterinary Research, vol. 59, No. 12, Dec. 1998, pp. 1540-1544.
Mengeling et al., "Clinical Effects of porcine reproductive and respiratory syndrome virus on pigs during the early postnatal interval". American Journal of Veterinary Research, vol. 59, No. 1, Jan. 1998, pp. 52-55.
Mengeling et al., "Comparative safety and efficacy of attenuated single-strain and multi-strain vaccines for porcine reproductive and respiratory syndrome". Veterinary Microbiology, vol. 93, 2003, pp. 25-38.
Mengeling et al., "Comparison among strains of porcine reproductive and respiratory syndrome virus for their ability to cause reproductive failure". American Journal of Veterinary Research, vol. 57, No. 6, Jun. 1996, pp. 834-839.
Mengeling et al., "Mystery Pig Disease: Evidence and Considerations for its Etiology". Proceedings of the Mystery Swine Disease Committee Meeting, Oct. 6, 1990, Denver, Colorado, Livestock Conservation Institute, Madison, WI, USA, pp. 88-90.
Mengeling et al., "Strain specificity of the immune response of pigs following vaccination with various strains of porcine reproductive and respiratory syndrome virus". Veterinary Microbiology, vol. 93, 2003, pp. 13-24.
Meredith, MJ, "Porcine Reproductive and Respiratory Syndrome (PRRS)", Pig Disease Information Center, 1st North American Edition, University of Cambridge, Aug. 1994, pp. 1-57.
Mettenleiter et al., "Isolation of a viable herpesvirus (pseudorabies virus) mutant specifically lacking all four known nonessential glycoproteins". Virology, vol. 179, No. 1, Nov. 1990, pp. 498-503.
Meulenberg et al., "An infectious cDNA clone of Porcine Reproductive and Respiratory Syndrome Virus". Coronaviruses and Arteriviruses (Advances in Experimental Medicine and Biology, vol. 440), Ch. 24, 1998, pp. 199-206.
Meulenberg et al., "Characterization of Proteins Encoded by ORFs 2 to 7 of Lelystad Virus". Virology, vol. 206, No. 1, Jan. 1995, pp. 155-163.

Meulenberg et al., "Identification and Characterization of a Sixth Structural Protein of Lelystad Virus: The Glycoprotein GP2Encoded by ORF2 Is Incorporated in Virus Particles". Virology, vol. 225, No. 1, Nov. 1996, pp. 44-51.
Meulenberg et al., "Infectious Transcripts from Cloned Genome-Length cDNA of Porcine Reproductive and Respiratory Syndrome Virus". Journal of Virology, vol. 72, No. 1, Jan. 1998, pp. 380-387.
Meulenberg et al., "Lelystad Virus, the Causative Agent of Porcine Epidemic Abortion and Respiratory Syndrome (PEARS), is Related to LDV and EAV". Virology, vol. 192, 1993, pp. 62-72.
Meulenberg et al., "Localization and Fine Mapping of Antigenic Sites on the Nucleocapsid Protein N of Porcine Reproductive and Respiratory Syndrome Virus with Monoclonal Antibodies". Virology, vol. 252, 1998, pp. 106-114.
Meulenberg et al., "Molecular characterization of Lelystad virus". Veterinary Microbiology, vol. 55, 1997, pp. 197-202.
Meulenberg et al., "Nucleocapsid Protein N of Lelystad Virus: Expression by Recombinant Baculovirus, Immunological Properties, and Suitability for Detection of Serum Antibodies". Clinical and Diagnostic Laboratory Immunology, vol. 2, No. 6, Nov. 1995, pp. 652-656.
Meulenberg et al., "Posttranslational Processing and Identification of a Neutralization Domain of the GP4 Protein Encoded by ORF4 of Lelystad Virus". Journal of Virology, vol. 71, No. 8, Aug. 1997, pp. 6061-6067.
Meulenberg et al., "Subgenomic RNAs of Lelystad virus contain a conserved leader-body junction sequence". Journal of General Virology, vol. 74, 1993, pp. 1697-1701.
Miller et al., "Interferon type I response in porcine reproductive and respiratory syndrome virus-infected MARC-145 cells". Archives of Virology, vol. 149, 2004, pp. 2453-2463.
Molenkamp et al., "Isolation and Characterization of an Arterivirus Defective Interfering RNA Genome". Journal of Virology, vol. 74, No. 7, 2000, pp. 3156-3165.
Molenkamp et al., "The arterivirus replicase is the only viral protein required for genome replication and subgenomic mRNA transcription". Journal of General Virology, vol. 81, No. 10, 2000, pp. 2491-2496.
Montagnon, B.J., "Polio and rabies vaccines produced in continuous cell lines: a reality for Vero cell line". Dev Biol Stand., vol. 70, 1989, pp. 27-47.
Moore, C., "Porcine Proliferative and Necrotyzing Pneumonia Clinical Findings". Presented at American Association of Swine Practitioners, 22nd Annual Meeting, Mar. 3-5, 1991, pp. 443-453.
Moormann et al., "Hog cholera virus: identification and characterization of the viral RNA and the virus specific RNA synthesized in infected swine kidney cells". Virus Research, vol. 11, 1988, pp. 281-291.
Moormann et al., "Infectious RNA Transcribed from an Engineered Full-Length cDNA Template of the Genome of a Pestivirus". Journal of Virology, vol. 70, No. 2, Feb. 1996, pp. 763-770.
Moormann et al., "Molecular cloning and nucleotide sequence of hog cholera virus strain brescia and mapping of the genomic region encoding envelope protein E1". Virology, vol. 177, No. 1, Jul. 1990, pp. 184-198.
Morin et al., "Severe proliferative and necrotizing pneumonia in pigs: A newly recognized disease". Canadian Veterinary Journal, vol. 31, Dec. 1990, pp. 837-839.
Morozov et al., "Sequence analysis of open reading frames (ORFs) 2 to 4 of a U.S. isolate of porcine reproductive and respiratory syndrome virus". Archives of Virology, vol. 140, No. 7, 1995, pp. 1313-1319.
Morrison et al., "Brief Communications Serologic evidence incriminating a recently isolated virus (ATCC VR-2332) as the cause of swine infertility and respiratory syndrome (SIRS)". Journal of Veterinary Diagnostic Investigation, vol. 4, No. 2, Apr. 1992, pp. 186-188.
Morrison et al., "Sero-epidemiologic Investigation of Swine Infertility and Respiratory Syndrome (SIRS)". 72st Annual Meeting of the Conference of Research Workers in Animal Disease, Chicago, IL, Nov. 11-12, 1991, p. 55, Abstract No. 309.

(56) References Cited

OTHER PUBLICATIONS

Mountz et al., "The in vivo generation of murine IgD-secreting cells is accompanied by deletion of the Cμ gene and occasional deletion of the gene for the Cd1 domain". The Journal of Immunology, vol. 145, No. 5, Sep. 1990, pp. 1583-1591.
Mukamoto et al., "Immunogenicity in Aujeszky's disease virus structural glycoprotein gVI (gp50) in swine". Veterinary Microbiology, vol. 29, No. 2, Oct. 1991, pp. 109-121.
Yoon et al., "Isolation of a Cytopathic Virus from Weak Pigs on Farms with a History of Swine Infertility and Respiratory Syndrome". Journal of Veterinary Diagnostic Investigation, vol. 4, Apr. 1992, pp. 139-143.
Yu et al., "Specific Binding of Host Cellular Proteins to Multiple Sites within the 39 End of Mouse Hepatitis Virus Genomic RNA". Journal of Virology, vol. 69, No. 4, Apr. 1995, pp. 2016-2023.
Yuan et al., "Complete genome comparison of porcine reproductive and respiratory syndrome virus parental and attenuated strains". Virus Research, vol. 74, 2001, pp. 99-110.
Yuan et al., "Erratum to 'Complete genome comparison of porcine reproductive and respiratory syndrome virus parental and attenuated strains'[Virus Research 74 (2001) 99-110]". Virus Research, vol. 79, 2001, p. 187.
Yuan et al., "Molecular characterization of a highly pathogenic strain of PRRSV associated with porcine High Fever syndrome in China". 2007 International Porcine Reproductive and Respiratory Syndrome (PRRS) Symposium, Chicago, Illinois, Nov.-Dec. 2007, Poster 70.
Yuan et al., American Society for Virology, 16th Annual Meeting, Bozeman, Montana, Jul. 19-23, 1997, Abstract p. 29-5, p. 229.
Zeijst, et al., "The Genome of Equine Arteritis Virus". Virology, vol. 68, 1975, pp. 418-425.
Zhou et al., "Generation of cytotoxic and humoral immune responses by nonreplicative recombinant Semliki Forest virus". Proceedings of the National Academy of Sciences, vol. 92, Mar. 1995, pp. 3009-3013.
Zimmerman et al., "General overview of PRRSV: A perspective from the United States". Veterinary Microbiology, vol. 55, Nos. 1-4, Apr. 1997, pp. 187-196.
Fang et al., "A Full-Length cDNA Infectious Clone of North American Type 1 Porcine Reproductive and Respiratory Syndrome Virus: Expression of Green Fluorescent Protein in the Nsp2 Region". Journal of Virology, vol. 80, No. 23, Dec. 2006, pp. 11447-11455.
Huang et al., "Novel strategies and approaches to develop the next generation of vaccines against porcine reproductive and respiratory syndrome virus (PRRSV)". Virus Research, vol. 154, 2010, pp. 141-149.
Thanawongnuwech et al., "Taming PRRSV: Revisiting the control strategies and vaccine design". Virus Research, vol. 154, No. 1-2, 2010, pp. 133-140.
Nam et al. "Complete genomic characterization of a European type 1 porcine reproductive and respiratory syndrome virus isolate in Korea". Archives of Virology, vol. 154, No. 4, 2009, pp. 629-638.
Deng et al., "An improved procedure for utilizing terminal transferase to add homopolymers to the 3' termini of DNA". Nucleic Acids Research, vol. 9, No. 16, 1981, pp. 4173-4188.
Derbyshire, J.B. "Porcine Enterovirus Infections". Diseases of Swine, Fifth Edition, Chapter 20, 1981, pp. 265-270.
Devereux et al., "A Comprehensive Set of Sequence Analysis Programs for VAX". Nucleic Acids Research, vol. 12, No. 1, 1984, pp. 387-395.
Dianzani et al., "Is Human Immunodeficiency Virus RNA Load Composed of Neutralized Immune Complexes". The Journal of Infectious Diseases, vol. 185, 2002, pp. 1051-1054.
Dildrop et al., "Immunoglobulin V region variants in hybridoma cells. II. Recombination between V genes". The EMBO Journal, vol. 1, No. 5, 1982, pp. 635-640.
Dreher, T.W., "Functions of the 3'-Untranslated Regions of Positive Strand RNA Viral Genomes". Annual Review of Phytopathology, vol. 37, 1999, pp. 151-174.

Drew et al., "Production, characterization and reactivity of monoclonal antibodies to porcine reproductive and respiratory syndrome virus". Journal of General Virology, vol. 76, 1995, pp. 1361-1369.
Drew, T., "Porcine Reproductive and Respiratory Syndrome Virus: A Review". Apr. 1996, 3 pages.
Duan et al., "Identification of a putative Receptor for Porcine Reproductive and Respiratory Syndrome Virus on Porcine Alveolar Macrophages". Journal of Virology, vol. 72, No. 5, May 1998, pp. 4520-4523.
Duran et al. "Recombinant Baculovirus Vaccines Against Porcine Reproductive and Respiratory Syndrome (PRRS)". Abstracts PRRS, Aug. 9 to 10, 1995, Copenhagen, Denmark, 2 pages.
Dykhuizen et al., "Determining the Economic Impact of the 'New' Pig Disease", Porcine Reproductive and Respiratory Syndrome, A Report on the Seminar Held in Brussels on Nov. 4-5, 1991 and Organized by the European Commission, pp. 53-60.
Easterday, B.C., "Swine Influenza". Diseases of Swine, Sixth Edition, Iowa State University Press, 1986, pp. 244-315. (Part One of Two—pp. 244-285). This NPL is too large for EFS submission. Therefore filing in two parts.
Easterday, B.C., "Swine Influenza". Diseases of Swine, Sixth Edition, Iowa State University Press, 1986, pp. 244-315. (Part Two of Two—pp. 286-315). This NPL is too large for EFS submission. Therefore filing in two parts.
Easterday, et al., "Swine Influenza". In Diseases of Swine (8th Edition), BE Straw, S D'Allaire, WI. Mengeling, DJ Taylor, eds., Ames: Iowa State University Press, 1999, pp. 277-290.
Edwards et al., "Oligodeoxyribonucleotide ligation to single-stranded cDNAs: a new tool for cloning 5' ends of mRNAs and for constructing cDNA libraries by in vitro amplification". Nucleic Acids Research, vol. 19, No. 19, 1991, pp. 5227-5232.
Ehresmann et al., "RNA synthesized in calicivirus-infected cells is atypical of picornaviruses". Journal of Virology, vol. 22, No. 2, May 1977, pp. 572-576.
Ellis, R.W., "New Technologies for Making Vaccines". Vaccines, Chapter 29, Plotkin et al Eds., WB Saunders Company, Philadelphia, PA, 1988, pp. 568-575.
Enjuanes et al., "Isolation and Properties of the DNA of African Swine Fever (ASF) Virus". Journal of General Virology, vol. 32, No. 3, Sep. 1976, pp. 479-492.
*Enzo Biochem Inc.* v. *Gen-Probe Incorporated et al.,* No. 01-01230; Decided Jul. 15, 2002.
Estes et al., "Simian rotavirus SA11 replication in cell cultures". Journal of Virology, vol. 31, No. 3, Sep. 1979, pp. 810-815.
Fang et al., "Heterogeneity in nsp2 of European-like porcine reproductive and respiratory syndrome viruses isolated in the United States". Virus Research, vol. 100, 2004, pp. 229-235.
Fenner et al., "Immunization against Viral Diseases", Veterinary Virology, Ch. 14, 1992, pp. 265-271.
Fenner et al., "Viral Genetics and Evolution", Veterinary Virology, Ch. 5, 1992, pp. 89-95.
Ferrari et al., "Isolation of Cytopathic Strains of Rotavirus from Pigs". Microbiologica, vol. 9, No. 3, Jul. 1986, pp. 287-294.
Flint et al., "Virus Cultivation, Detection, and Genetics". Virology, Molecular Biology, Pathogenesis, and Control, Ch. 2, 2000, pp. 40-42.
Foss et al., "Adjuvant Danger Signals Increase the Immune Response to Porcine Reproductive and Respiratory Syndrome Virus". Viral Immunology, vol. 15, No. 4, 2002, pp. 557-566.
Frolov et al., "Alphavirus-based expression vectors: Strategies and applications". Proceedings of the National Academy of Sciences, vol. 93, Oct. 1996, pp. 11371-11377.
Fu et al., "Detection and survival of group A rotavirus in a piggery". Veterinary Record, vol. 125, 1989, pp. 576-578.
Fukuhara et al., "Evidence for endocytosis-independent infection by human rotavirus". Archives of Virology, vol. 97, Nos. 1-2, 1987, pp. 93-99.
Funkhouser et al., "Mutations in the 5'-noncoding, 2C and P3 Regions of the Genome Increase the Efficiency of Hepatitis A Virus Growth in MRC-5 Cells". Vaccines, vol. 94, Cold Springs Harbor Laboratory Press, 1994, pp. 345-349.

(56) References Cited

OTHER PUBLICATIONS

Gao et al., "Genomic characterization of two Chinese isolates of Porcine respiratory and reproductive syndrome virus". Archives of Virology, vol. 149, 2004, pp. 1341-1351.
Garwes, D.J., "Transmissible gastroenteritis". Veterinary Record, vol. 122, 1988, pp. 462-463.
Geisbert et al., "Use of Immunoelectron Microscopy to Show Ebola Virus During the 1989 United States Epizootic". Journal of Clinical Pathology, vol. 43, No. 10, Oct. 1990, pp. 813-816.
Girard et al., "Experimentally induced porcine proliferative and necrotising pneumonia with an influenza A virus". The Veterinary Record, vol. 130, Mar. 1992, pp. 206-207.
Godeny et al., "Map location of lactate dehydrogenase-elevating virus (LDV) capsid protein (Vpl) gene", Virology, vol. 177, No. 2, Aug. 1990, pp. 768-771.
Godeny et al., "The 3' Terminus of Lactate Dehydrogenase-Elevating Virus Genome RNA Does Not Contain Togavirus or Flavivirus Conserved Sequences", Virology, vol. 72, 1989, pp. 647-650.
Goldfield et al., "Influenza in New Jersey in 1976: Isolations of Influenza A/New Jersey/76 Virus at Fort Dix". The Journal of Infectious Diseases, vol. 136, Supp. 3, 1977, pp. S347-S355.
Goldstein, et al., "Evaluation of Three Cell Culture Systems as Substrates for Influenza Virus Assay". Applied Microbiology, vol. 19, No. 4, Apr. 1970, pp. 580-582.
Gong et al., "Characterization of RNA synthesis during a one-step growth curve and of the replication mechanism of bovine viral diarrhoea virus". Journal of General Virology, vol. 77, 1996, pp. 2729-2736.
Gorcyca et al., RespPRRS: A new tool for the prevention and control of PRRS in pigs. Proceedings of the American Association of Swine Practitioners, Omaha, Nebraska, Mar. 1995, pp. 1-22.
Gourreau et al., "Diffusion du virus de la grippe du porc (H1N1=Hsw1N1) en France". Annales de l'Institut Pasteur/Virologie, vol. 132, No. 2, Apr.-Jun. 1981, pp. 287-294.
Goyal, S., "Porcine Reproductive and Respiratory Syndrome", Journal of Veterinary Diagnostic Investigation, vol. 5, No. 4, 1993, pp. 656-664.
Gravell et al., "Differences among isolates of simian hemorrhagic fever (SHF) virus". Proceedings of the Society for Experimental Biology and Medicine, vol. 181, No. 1, 1986, pp. 112-119.
Graves, J.H., "Swine Vesicular Disease". Diseases of Swine, Fifth Edition, Chapter 23, The Iowa State University Press, Ames, Iowa, 1958, pp. 288-293.
Grebennikova et al., "Genomic characterization of virulent, attenuated, and revertant passages of a North American porcine reproductive and respiratory syndrome virus strain". Virology, vol. 321, 2004, pp. 383-390.
Greiner et al., "Quantitative Effect of Porcine Reproductive Respiratory Syndrome Virus on Pig Growth and Immune Response".,1999, Swine Research Report, Paper 5, 1998, 4 pages.
Greiner et al., "Quantitative relationship of systemic virus concentration on growth and immune response in pigs". Journal of Animal Science, vol. 78, 2000, pp. 2690-2695.
Grizzard et al., "Experimental production of respiratory tract disease in cebus monkeys after intratracheal or intranasal infection with influenza A/Victoria/3/75 or influenza A/New Jersey/76 virus". Infection and Immunity, vol. 21, No. 1, Jul. 1978, pp. 201-205.
Grouse, L.D., "Swine Flue Sequelae"., Journal of the American Medical Association, vol. 243, No. 24, 1980, p. 2489.
Grunert et al., "Sensitivity of Influenza A/New Jersey/8/76 (HswINI) Virus to Amantadine-HCl". Journal of Infectious Diseases, vol. 136, No. 2, 1977, pp. 297-300.
Peng et al., "Analysis of Second-Site Revertants of a Murine Coronavirus Nucleocapsid Protein Deletion Mutant and Construction of Nucleocapsid Protein Mutants by Targeted RNA Recombination". Journal of Virology, vol. 69, No. 6, Jun. 1995, pp. 3449-3457.
Penzes et al., "Characterization of a Replicating and Packaged Defective RNA of Avian Coronavirus Infectious Bronchitis Virus". vol. 203, No. 2, Sep. 1994, pp. 286-293.
Percy et al., "Expression of a Foreign Protein by Influenza A Virus". Journal of Virology, vol. 68, No. 7, Jul. 1994, pp. 4486-4492.
Pesch et al., "New insights into the genetic diversity of European porcine reproductive and respiratory syndrome virus (PRRSV)". Veterinary Microbiology, vol. 107, 2005, pp. 31-48.
Pirtle et al., "Morphologic Heterogeneity of a Strain of Swine Influenza Virus (A/Swine/Wisconsin/1/68, Hsw1N1) Propagated at Different Temperatures". American Journal of Veterinary Research, vol. 36, No. 1, 1975, pp. 1783-1787.
Plagemann et al., "Lactate Dehydrogenase-Elevating Virus, Equine Arteritis Virus, and Simina Hemorrhagic Fever Virus: A New Group of Positive-Strand RNA Viruses". Advances in Virus Research, vol. 41, 1991, pp. 99-192.
Pol et al., "Pathological, ultrastructural, immunohistochemical changes caused by Lelystad virus in experimentally induced infections of mystery swine disease (synonym: porcine epidemic abortion and respiratory syndrome (PEARS))". Veterinary Quarterly, vol. 13, No. 3, Jul. 1991, pp. 137-143.
Polson et al., "An evaluation of the financial impact of Porcine Reproductive and Respiratory Syndrome (PRRS) in nursery pigs". Proceedings of the 13th International Pig Veterinary Society Congress, Jun. 1994, p. 31.
Polson et al., "Financial Implications of Mystery Swine Disease (MSD)". 1993, pp. 8-28.
Polson, DD, "Answers to Your Questions on PRRS". NOBL Laboratories, 1993, 18 Pages.
Polson, DD, "RespPRRS a PRRS Vaccine Review", NOBL Laboratories, 1993, 22 pages.
Porcine Reproductive and Respiratory Syndrome: A Report on the Seminar Held in Brussels on Nov. 4-5, 1991 and Organized by the European Commission.
Poser, C.M., "Swine Influenza Vaccination: Truth and Consequences". Archives of Neurology, vol. 42, No. 11, 1985, pp. 1090-1092.
Potgieter et al., "Isolation of Swine Influenza Virus in Oklahoma". Journal of the American Veterinary Medical Association, vol. 171, No. 8, 1977, pp. 758-760.
Potts et al., "Peroxidase-labeled primary antibody method for detection of pestivirus contamination in cell cultures". Journal of Virological Methods, vol. 26, No. 1, Oct. 1989, pp. 119-124.
Quaife, T. "Mystery Agent Isolated! Isolation of the etiological agent behind mystery swine disease is a major breakthrough". Swine Practitioner, Mystery Disease: Part 8, Nov. 1991, pp. 4-7.
Reed et al., "A Simple Method of Estimating Fifty Per Cent Endpoints"., The American Journal of Hygiene, vol. 27, No. 3, May 1938, pp. 493-497.
Reed et al., "Persistent Respiratory Virus Infection in Tracheal Organ Cultures". British Journal of Experimental Pathology, vol. 50, 1969, pp. 378-388.
Rice et al., "Production of Infectious RNA Transcripts from Sindbis Virus cDNA Clones: Mapping of Lethal Mutations, Rescue of a Temperature-Sensitive Marker, and In Vitro Mutagenesis to Generate Defined Mutants". Journal of Virology, vol. 61, No. 12, Dec. 1987, pp. 3809-3819.
Roberts et al., "Abortion in Swine". Veterinary Ostetrics and Genital Diseases, Edwards Brothers, Inc., Ann Arbor, 1986, pp. 180-192.
Roof et al., "Efficacy of Modified Live Virus Porcine Reproductive and Respiratory Virus Vaccines Against Heterologous Respiratory Challenge". 4th International Symposium on Emerging and Re-emerging Pig Diseases, Rome, Jun. 28-Jul. 2, 2003, pp. 117-118.
Ropp et al., "Characterization of Emerging European-Like Porcine Reproductive and Respiratory Syndrome Virus Isolates in the United States"., Journal of Virology, vol. 78, No. 7, Apr. 2004, pp. 3684-3703.
Rossow et al., "Experimental porcine reproductive and respiratory syndrome virus infection in one-, four-, and 10-week-old pigs". Journal of Veterinary Diagnostic Investigation, vol. 6, 1993, pp. 3-12.
Rossow, K.D., "Porcine Reproductive and Respiratory Syndrome". Veterinary Pathology, vol. 35, 1998, pp. 1-20.
Roth et al., "Influenza virus hemagglutinin expression is polarized in cells infected with recombinant SV40 viruses carrying cloned hemagglutinin DNA". Cell, vol. 33, No. 2, Jun. 1983, pp. 435-443.

(56) References Cited

OTHER PUBLICATIONS

Roth et al., "The large external domain is sufficient for the correct sorting of secreted or chimeric influenza virus hemagglutinins in polarized monkey kidney cells". The Journal of Cell Biology, vol. 104, Mar. 1987, pp. 769-782.
Rottier et al., "Predicted Membrane Topology of the Coronavirus Protein E1". Biochemistry, vol. 25, 1986, pp. 1335-1339.
Rovira et al., "Experimental Inoculation of Conventional Pigs with Porcine Reproductive and Respiratory Syndrome virus and Porcine Circovirus 2", J. Virol, jApr. 2002, vol. 76, No. 7, pp. 3232-3239.
Sagripanti et al., "The Cap Structure of Simian Hemorrhagic Fever Virion RNA". Virology, vol. 151, 1986, pp. 143-150.
Saif et al., "Serial propagation of porcine group C rotavirus (pararotavirus) in a continuous cell line and characterization of the passaged virus". Journal of Clinical Microbiology, vol. 26, No. 7, Jul. 1988, pp. 1277-1282.
Saif, L.J., "Coronavirus Immunogens". Veterinary Microbiology, vol. 37, No. 3-4, Nov. 1993, pp. 285-297.
Sarnow, P. "Role of 3'-End Sequences in Infectivity of Poliovirus Transcripts Made In Vitro". Journal of Virology, vol. 63, No. 1, Jan. 1989, pp. 467-470.
Sawicki et al., "Coronavirus Transcription: Subgenomic Mouse Hepatitis Virus Replicative Intermediates Function in RNA Synthesis". Journal of Virology, vol. 64, No. 3, Mar. 1990, pp. 1050-1056.
Schmidt et al., "Infection of Influenza A Viruses of Tracheal Organ Cultures Derived from Homologous and Heterologous Hosts". The Journal of Infectious Diseases, vol. 129, No. 1, 1974, pp. 28-36.
Scott, F.W., "Immunization against feline coronaviruses". Advances in Experimental Medicine and Biology, vol. 218, 1987, pp. 569-576.
Seal et al., "Analysis of the Serologic Relationship among San Miguel Sea Lion Virus and Vesicular Exanthema of Swine Virus Isolates. Application of the Western Blot Assay for Detection of Antibodies in Swine Sera to these Virus Types". Journal of Veterinary Diagnostic Investigation, vol. 7, No. 2, Apr. 1995, pp. 190-195.
Seal et al., "Isolation of caliciviruses from skunks that are antigenically and genotypically related to San Miguel sea lion virus Original Research". Virus Research, vol. 37, No. 1, Jun. 1995, pp. 1-12.
Seneca, H., "Influenza: epidemiology, etiology, immunization and management". Journal of American Geriatrics Society, vol. 28, No. 6, Jun. 1980, pp. 241-250.
Sethna et al., "Coronavirus subgenomic minus-strand RNAs and the potential for mRNA replicons". Proceedings of the National Academy of Sciences, vol. 86, Jul. 1989, pp. 5626-5630.
Setzer et al., "Size Heterogeneity in the 3' End of Dihydrofolate Reductase Messenger RNAs in Mouse Cells". Cell, vol. 22, Nov. 1980, pp. 361-370.
Shaw et al., "Experimental rotavirus infection in three-week-old pigs". American Journal of Veterinary Research, vol. 50, No. 11, Nov. 1989, pp. 1961-1965.
Shen et al., "Determination of the complete nucleotide sequence of a vaccine strain of porcine reproductive and respiratory syndrome virus and identification of the Nsp2 gene with a unique insertion". Archives of Virology, vol. 145, No. 5, May 2000, pp. 871-883.
Shi et al., "Endoribonuclease activities of porcine reproductive and respiratory syndrome virus nsp11 was essential for nsp11 to inhibit IFN-β induction". Molecular Immunology, vol. 48, 2011, pp. 1568-1572.
Shi et al., "Porcine reproductive and respiratory syndrome virus (PRRSV) could be sensed by professional beta interferon-producing system and had mechanisms to inhibit this action in MARC-145 cells". Virus Research, vol. 153, 2010, pp. 151-156.
Shi et al., "The Nonstructural Protein 1 Papain-Like Cysteine Protease Was Necessary for Porcine Reproductive and Respiratory Syndrome Virus Nonstructural Protein 1 to Inhibit Interferon-β Induction". DNA and Cell Biology, vol. 30, No. 6, 2011, pp. 355-362.
Shibata et al., "Detection of Human Papilloma Virus in Paraffin-Embedded Tissue Using the Polymerase Chain Reaction". The Journal of Experimental Medicine, vol. 167, No. 1, Jan. 1988, pp. 225-230.
Shieh et al., "The 5'-End Sequence of the Murine Coronavirus Genome: Implications of Multiple Fusion Sites in Leader-Primed Transcription". Virology, vol. 156, 1987, pp. 321-330.
Shin et al., "Assessment of Porcine Reproductive and Respiratory Syndrome Virus RNA Load in Sera and Tissues during Acute Infection". Journal of Veterinary Science, vol. 3, No. 2, 2002, pp. 75-85.
Shope et al., "The Susceptibility of Swine to the Virus of Human Influenza". Annual Meeting of the Society of American Bacteriologists in New York, 1936, pp. 791-801.
Shortridge et al., "Geographical Distribution of Swine (HSw1N1) and Hong Kong (H3N2) Influenza Virus Variants in Pigs in Southeast Asia". Intervirology, vol. 11, No. 1, 1979, pp. 9-15.
Murakami, et al., "Difference in growth behavior of human, swine, equine, and avian influenza viruses at a high temperature". Archives of Virology, vol. 100, Nos. 3-4, 1988, pp. 231-244.
Murphy et al., "Immunization Against Virus" in Virology, 2nd Edition, vol. 1, Fields, et al., eds. Raven Press, NY, 1990, pp. 469-502.
Murphy et al., "Virus Taxonomy". Chapter 2 in Fields Virology, 2nd. Edition, Fields, et al., eds, Raven Press, New York, 1990, pp. 9-35.
Murtaugh et al., "Comparison of the structural protein coding sequences of the VR-2332 and Lelystad virus strains of the PRRS virus". Archives of Virology, vol. 140, No. 8, 1995, pp. 1451-1460.
Murtaugh et al., "Genetic Variation in the PRRS Virus". Coronaviruses and Arteriviruses, Plenum Press, New York, 1998, pp. 787-794.
Murtaugh et al., "Immunological Responses of Swine to Porcine Reproductive and Respiratory Syndrome Virus Infection". Viral Immunology, vol. 15, No. 4, 2002, pp. 533-547.
Murtaugh et al., "Role of Viral Proteases in PRRS Immunity, Project Period Sep. 1, 1997-Dec. 31, 2001, no cost extension Jan. 1, 2003-Jun. 30, 2003". Final Report: Aug. 30, 2003, Department of Veterinary Pathology, University of Minnesota, St. Paul, MN and Boehringer Ingelheim Vetmedica, Inc., Ames, IA, 2003, pp. 1-38.
Murtaugh, "Allen D Lehman Swine Conference: the Evolution of the Swine veterinary profession: The PRRS Virus". University of Minnesota, Veterinary Continuing Education and Extension, vol. 20, 1993, pp. 43-47.
Myers et al., "Propagation of avian rotavirus in primary chick kidney cell and MA104 cell cultures". Avian Diseases, vol. 33, No. 3, Jul.-Sep. 1989, pp. 578-581.
Nakamura et al., "Studies on Swine Influenza III. Propagation of Swine Influenza Virus in Explants of Respiratory Tract Tissues from Fetal Pigs". The Cornell Veterinarian, vol. LX, No. 1, Jan. 1970, pp. 27-35.
Narayanan et al., "Characterization of the Coronavirus M Protein and Nucleocapsid Interaction in Infected Cells". Journal of Virology, vol. 74, No. 17, Sep. 2000, pp. 8127-8134.
NCBI: Accession No. AE005172. "Arabidopsis thaliana chromosome 1, top arm complete sequence." Dec. 14, 2000.
NCBI: Accession No. AF046869. "Porcine reproductive and respiratory syndrome virus isolate 16244B, Feb. 18, 1997 (Nebraska) pass.3, complete genome." Mar. 17, 1999.
NCBI: Accession No. AF066183. "Porcine reproductive and respiratory syndrome virus RespPRRS MLV, complete genome." Feb. 22, 2001.
NCBI: Accession No. AF159149. "Porcine reproductive and respiratory syndrome virus isolate MLV RespPRRS/Repro, complete genome." Aug. 28, 2000.
NCBI: Accession No. AF176348. "Porcine reproductive and respiratory syndrome virus isolate PA8 complete genome." Sep. 3, 2002.
NCBI: Accession No. AF184212. "Porcine reproductive and respiratory syndrome virus strain SP, complete genome." Sep. 28, 2000.
NCBI: Accession No. AF325691. "Porcine reproductive and respiratory syndrome virus isolate NVSL 977985 IA 1-4-2, complete genome." Feb. 11, 2001.
NCBI: Accession No. AF331831. "Porcine reproductive and respiratory syndrome virus BJ-4, complete genome." Jan. 15, 2001.
NCBI: Accession No. M96262. "Lelystad virus, complete genome." Nov. 8, 2000.
NCBI: Accession No. M96262.2. "Lelystad virus, complete genome." Nov. 8, 2000.
NCBI: Accession No. NC_001639. Lactate dehydrogenase-elevating virus, complete genome. Dec. 8, 2008.

(56) References Cited

OTHER PUBLICATIONS

NCBI: Accession No. NC_001961. "Porcine reproductive and respiratory syndrome virus, complete genome." Jan. 12, 2004.
NCBI: Accession No. NC_002533. "Lelystad virus, complete genome." Nov. 11, 2000.
NCBI: Accession No. NC_002534. "Lactate dehydrogenase-elevating virus, complete genome." Dec. 29, 2003.
NCBI: Accession No. U15146. "Lactate dehydrogenase-elevating virus Plagemann strain, complete genome." Jan. 26, 1996.
NCBI: Accession No. U87392 AF030244 000153. "Porcine reproductive and respiratory syndrome virus strain VR-2332, complete genome." Nov. 17, 2000.
Nelsen et al., "Porcine Reproductive and Respiratory Syndrome Virus Comparison: Divergent Evolution on Two Continents". Journal of Virology, vol. 73, No. 1, Jan. 1999, pp. 270-280.
Nelson et al., "Differentiation of U.S. and European Isolates of Porcine Reproductive and Respiratory Syndrome Virus by Monoclonal Antibodies". Journal of Clinical Microbiology, vol. 31, No. 12, Dec. 1993, pp. 3184-3189.
Nelson et al., "High affinity interaction between nucleocapsid protein and leader/intergenic sequence of mouse hepatitis virus RNA". Journal of General Virology, vol. 81, 2000, pp. 181-188.
Nielsen et al., "Generation of an Infectious Clone of VR-2332, a Highly Virulent North American-Type Isolate of Porcine Reproductive and Respiratory Syndrome Virus". Journal of Virology, vol. 77, No. 6, Mar. 2003, pp. 3702-3711.
Nishimura et al., "Replication and Synthesis of Japanese Encephalitis Virus Ribonucleic Acids in Vero Cells". Japanese Journal of Microbiology, vol. 15, No. 4, 1971, pp. 309-316.
Nodelijk et al., "A quantitative assessment of the effectiveness of PRRSV vaccination in pigs under experimental conditions". Vaccine, vol. 19, 2000, pp. 3636-3644.
Nuttall, P.A., "Growth Characteristics of Two Strains of Bovine Virus Diarrhoea Virus". Archives of Virology, vol. 66, 1980, pp. 365-369.
Oirschot et al., "Development of an ELISA for detection of antibodies to glycoprotein I of Aujeszky's disease virus: a method for the serological differentiation between infected and vaccinated pigs". Journal of Virological Methods, vol. 22, 1988, pp. 191-206.
Ojeh et al., "Isolation, characterisation and serial propagation of a Nigerian strain of porcine group A rotavirus in a monkey kidney cell line (MA104)". Discovery and Innovation, vol. 8, No. 2, Jun. 1996, pp. 159-164.
Oleksiewicz et al., "Epitope Mapping Porcine Reproductive and Respiratory Syndrome Virus by Phage Display: the nsp2 Fragment of the Replicase Polyprotein Contains a Cluster of B-Cell Epitopes". Journal of Virology, vol. 75, No. 7, Apr. 2001, pp. 3277-3290.
Oleksiewicz et al., "Semen from Boars Infected with Porcine Reproductive and Respiratory Syndrome Virus (PRRSV) Contains Antibodies Against Structural as Well as Nonstructural Viral Proteins". Veterinary Microbiology, vol. 81, 2001, pp. 109-125.
Olsthoorn et al., "A conformational switch at the 3' end of a plant virus RNA regulates viral replication". The EMBO Journal, vol. 18, No. 17, 1999, pp. 4856-4864.
Opriessnig et al., "Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and Two Recent Field Isolates of PRRSV". Journal of Virology, vol. 76, No. 23, Dec. 2002, pp. 11837-11844.
Opriessnig et al., "Use of an Experimental Model to Test the Efficacy of Planned Exposure to Live Porcine Reproductive and Respiratory Syndrome Virus". Clinical and Vaccine Immunology, vol. 14, No. 12, Dec. 2007, pp. 1572-1577.
Ostrowski et al., "Identification of Neutralizing and Nonneutralizing Epitopes in the Porcine Reproductive and Respiratory Syndrome Virus GP5 Ectodomain". Journal of Virology, vol. 76, No. 9, May 2002, pp. 4241-4250.
Pan et al., "Replication of African swine fever virus in cell cultures". American Journal of Veterinary Research, vol. 41, No. 9, Sep. 1980, pp. 1357-1367.
Parratt et al., "Radioimmunoassay of Antibody and its Clinical Applications". John Wiley & Sons, Chichester, 1982, p. 43.
Parsley et al., "Poly (rC) binding protein 2 forms a ternary complex with the 5'-terminal sequences of poliovirus RNA and the viral 3CD proteinase". RNA, vol. 3, 1997, pp. 1124-1134.
Patriarca, et al., "Lack of Significant Person-to-Person Spread of Swine Influenza-Like Virus Following Fatal Infection in an Immunocomprised Child". American Journal of Epidemiology, vol. 119, No. 2, 1984, pp. 152-158.
Paul et al., "Porcine Reproductive and Respiratory Syndrome: An Overview". Journal of Clinical Veterinary Medicine, vol. 11, No. 12, Nov. 1993, pp. 1-16.
Pearson et al., "Improved tools for biological sequence comparison". Proceedings of the National Academy of Sciences, vol. 85, Apr. 1988, pp. 2444-2448.
Pedersen et al., "Open Reading Frame 1a-Encoded Subunits of the Arterivirus Replicase Induce Endoplasmic Reticulum-Derived Double-Membrane Vesicles Which Carry the Viral Replication Complex". Journal of Virology, vol. 73, No. 3, Mar. 1999, pp. 2016-2026.
Pejsak et al., "Clinical signs and economic losses caused by porcine reproductive and respiratory syndrome virus in a large breeding farm". Veterinary Microbiology, vol. 44, 1997, pp. 317-322.
Van Marle et al., "Arterivirus discontinuous mRNA transcription is guided by base pairing between sense and antisense transcription-regulating sequences". Proceedings of the National Academy of Sciences, vol. 96, 1999, pp. 12056-12061.
Van Marle et al., "Characterization of an Equine Arteritis Virus Replicase Mutant Defective in Subgenomic mRNA Synthesis". Journal of Virology, vol. 73, No. 7, Jul. 1999, pp. 5274-5281.
Van Marle et al., "Regulation of Coronavirus mRNA Transcription". Journal of Virology, vol. 69, No. 12, Dec. 1995, pp. 7851-7856.
Van Nieuwstadt et al., "Infection with porcine respiratory coronavirus does not fully protect pigs against intestinal transmissable gastroenteritis virus". The Veterinary Record, vol. 125, No. 3, 1989, pp. 58-60.
Van Nieuwstadt et al., "Proteins Encoded by Open Reading Frames 3 and 4 of the Genome of Lelystad Virus (Arteriviridae) Are Structural Proteins of the Virion". Journal of Virology, vol. 70, No. 7, Jul. 1996, pp. 4767-4772.
Van Nieuwstadt et al., "Use of two enzyme-linked immunosorbent assays to monitor antibody responses in swine with experimentally induced infection with porcine epidemic diarrhea virus". American Journal of Veterinary Research, vol. 42, Jul. 1991, pp. 1044-1050.
Van Zijl et al., "Live Attenuated Pseudorabies Virus Expressing Envelope Glycoprotein E1 of Hog Cholera Virus Protects Swine Against Both Pseudorabies and Hog Cholera". Journal of Virology, vol. 65, No. 5, May 1991, pp. 2761-2765.
Vennema et al., "Nucleocapsid-independent assembly of coronavirus-like particles by co-expression of viral envelope protein genes". The EMBO Journal, vol. 15, No. 8, 1996, pp. 2020-2028.
Verheije et al., "Kissing Interaction between 3' Noncoding and Coding Sequences is Essential for Porcine Arterivirus RNA Replication". Journal of Virology, vol. 76, No. 3, Feb. 2002, pp. 1521-1526.
Verheije et al., "Safety and protective efficacy of porcine reproductive and respiratory syndrome recombinant virus vaccines in young pigs". Vaccine, vol. 21, 2003, pp. 2556-2563.
Veterinary Bulletin, vol. 58, No. 11, 1988, Nos. 6903-6909, p. 932.
Veterinary Bulletin, vol. 60, No. 3, 1990, Nos. 1536-1551, pp. 255-256.
Vieira et al., "New pUC-derived cloning vectors with different selectable markers and DNA replication origins". Gene, vol. 100, 1991, pp. 189-194.
VIIIth International Symposium on Nidoviruses (Corona and Arteriviruses), May 20-25, 2000, 32 pages.
Visser, Nicolaas, "Declaration of Dr. N. Visser". Nov. 14, 1995, pp. 1-11.
Von Busse, F.W., Epidemiologic Studies on Porcine Reproductive and Respiratory Syndrome (PRRS). Tierarztliche Umschau, Dec. 1991, pp. 708-717 (Abstract in English p. 711).
Von Ohlinger et al., "Der Seuchenhafte Spatabort beim Schwein Ein Beitrag zur Atiologie des Porcine Reproductive and Respiratory Syndrome (PRRS)". Tierarztl, vol. 46, 1991, pp. 703-708.

(56) References Cited

OTHER PUBLICATIONS

Waltner-Toews et al., "A Field Trial to Evaluate the Efficacy of a Combined Rotavirus-Coronavirus/ *Escherichia coli* vaccine in Dairy Cattle"., Canadian Journal of Comparative Medicine, vol. 49, No. 1, 1985, pp. 1-9.
Wang et al., "Attenuation of porcine reproductive and respiratory syndrome virus strain MN184 using chimeric construction with vaccine sequence". Virology, vol. 371, 2008, pp. 418-429.
Ward et al., "Efficiency of human rotavirus propagation in cell culture". Journal of Clinical Microbiology, vol. 19, No. 6, Jun. 1984, pp. 748-753.
Wardley et al., "The Host Response to African Swine Fever Virus". Progress of Medical Virology, vol. 34, 1987, pp. 180-192.
Wassenaar et al., "Alternative Proteolytic Processing of the Arterivirus Replicase ORF1a Polyprotein: Evidence that NSP2 Acts as a Cofactor for the NSP4 Serine Protease". Journal of Virology, vol. 71, No. 12, Dec. 1997, pp. 9313-9322.
Webster et al., "Chemotherapy and Vaccination: a Possible Strategy for the Control of Highly Virulent Influenza Virus". Journal of Virology, vol. 55, No. 1, 1985, pp. 173-176.
Welch et al., "Construction and evaluation of genetically engineered replication-defective porcine reproductive and respiratory syndrome virus vaccine candidates". Veterinary Immunology and Immunopathology, vol. 102, 2004, pp. 277-290.
Wensvoort et al., "'Blue ear' disease in pigs". Veterinary Record, vol. 128, No. 24, Jun. 1991, p. 574.
Wensvoort et al., "'Lelystad agent'—the cause of abortus blauw (mystery swine disease)". Tijdschr Diergeneeskd, vol. 116, No. 13, Jul. 1991, pp. 675-676.
Wensvoort et al., "An Enzyme Immunoassay Employing Monoclonal Antibodies and Detecting Specifically Antibodies to Classical Swine Fever Virus". Veterinary Microbiology, vol. 17, 1988, pp. 129-140.
Wensvoort et al., "Antigenic Comparison of Lelystad Virus and Swine Infertility and Respiratory Syndrome (SIRS) Virus". Journal of Veterinary Diagnostic Investigation, vol. 4, 1992, pp. 134-138.
Wensvoort et al., "Bovine viral diarrhoea virus infections in piglets born to sows vaccinated against swine fever with contaminated vaccine". Research in Veterinary Science, vol. 45, 1988, pp. 143-148.
Wensvoort et al., "Characterization of Porcine and Some Ruminant Pestiviruses by Cross-neutralization" vol. 20, 1989, pp. 291-306.
Wensvoort et al., "Lelystad virus, the cause of porcine epidemic abortion and respiratory syndrome: a review of mystery swine disease research in Lelystad". Veterinary Microbiology, vol. 33, Nos. 1-4, Nov. 1992, pp. 185-193.
Wensvoort et al., "Mystery Swine Disease in the Netherlands the Isolation of Lelystad Virus". The Veterinary Quarterly, vol. 13, No. 3, 1991, pp. 121-130.
Wensvoort et al., "Production of Monoclonal Antibodies Against Swine Fever Virus and Their Use in Laboratory Diagnosis". Veterinary Microbiology, vol. 12, 1986, pp. 101-108.
Wensvoort et al., "The Porcine Reproductive and Respiratory Syndrome; Characteristics and diagnosis of the causative virus". Veterinary Biotechnology Newsletter, vol. 3, 1993, pp. 113-120.
Wesley et al., "Differentiation of a porcine reproductive and respiratory syndrome virus vaccine strain from North American field strains by restrction fragment length polymorphism analysis of ORF 5". Journal of Veterinary Diagnostic Investigation, vol. 10, 1998, pp. 140-144.
Wesley et al., "Differentiation of vaccine (strain RespPRRS) and field strains of porcine reproductive and respiratory syndrome virus by restriction enzyme analysis". Proceedings of the American Association on Swine Practitioners, Nashville, TN, USA, 1996, pp. 141-143.
Westenbrink et al., "An enzyme-linked immunosorbent assay for detection of antibodies to porcine parvovirus". Journal of Virological Methods, vol. 23, 1989, pp. 169-178.
Wieczorek-Krohmer et al., "Porcine reproductive and respiratory syndrome virus (PRRSV): Monoclonal antibodies detect common epitopes on two viral proteins of European and U.S. isolates". Veterinary Microbiology, vol. 51, Nos. 3-4, Aug. 1996, pp. 257-266.
Witte, K.H. "The Situation of 'Epidemic Late Abortion of Swine' in the State of Northrhine-Westphalia". Workshop Seminar, Apr. 1991.

Woode, et al., "Porcine Rotavirus Infection". Diseases of Swine, Fifth Edition, Chapter 26, The Iowa State University Press, Ames, Iowa, 1981, pp. 310-322.
Woods et al., "Antigenicity of Inactivated Swine Influenza Virus Concentrated by Centrifugation". Research Communications in Chemical Pathology and Pharmacology, vol. 13, No. 1, 1976, pp. 129-132.
Woods et al., "Experimental challenge of pregnant gilts with swine influenza virus after vaccination". Research Communications in Chemical Pathology and Pharmacology, vol. 15, No. 4, Dec. 1976, pp. 787-795.
Woods et al., "Investigation of Four Outbreaks of Acute Respiratory Disease in Swine and Isolation of Swine Influenza Virus". Health Laboratory Science, vol. 5, No. 4, Oct. 1968, pp. 218-224.
Wootton et al., "Structure-function of the ORF7 protein of porcine reproductive and respiratory syndrome virus in the viral capsid assembly". Proceedings of the International Symposium on PRRS and Aujeszky's Disease, Ploufragan, France, Jun. 21-24, 1999, pp. 37-38.
Xiao et al., "The Level of Virus-Specific T-Cell and Macrophage Recruitment in Porcine Reproductive and Respiratory Syndrome Virus Infection in Pigs Is Independent of Virus Load". Journal of Virology, vol. 78, No. 11, Jun. 2004, pp. 5923-5933.
Xue et al., "The Crystal Structure of Porcine Reproductive and Respiratory Syndrome Virus Nonstructural Protein Nsp1b Reveals a Novel Metal-Dependent NucleaseN". Journal of Virology, vol. 84, No. 13, Jul. 2010, pp. 6461-6471.
Yamane et al., "Annual Examination of Influenza Virus Infection Among Pigs in Miyagi Prefecture, Japan: the Appearance of Hsw1N1 Virus". Acta Virologica, vol. 23, 1979, pp. 240-248.
Yang et al., "Comparative sequence analysis of open reading frames 2 to 7 of the modified live vaccine virus and other North American isolates of the porcine reproductive and respiratory syndrome virus". Archives of Virology, vol. 143, 1998, pp. 601-612.
Yoon et al., "A modified serum neutralization test for the detection of antibody to porcine reproductive and respiratory syndrome virus in swine sera". Journal of Veterinary Diagnostic Investigation, vol. 6, No. 3, Jul. 1994, pp. 289-292.
Yoon et al., "Failure to Consider the Antigenic Diversity of Porcine Reproductive and Respiratory Syndrome (PRRS) Virus Isolates May Lead to Misdiagnosis". Journal of Veterinary Diagnostic Investigation, vol. 7, Jul. 1995, pp. 386-387.
Brockmeier et al., "Genomic sequence and virulence comparison of four Type 2 porcine reproductive and respiratory syndrome virus strains". Virus Research, vol. 169, No. 1, 2012, pp. 212-221.
Leng et al., "Evaluation of the Efficacy of an Attenuated Live Vaccine against Highly Pathogenic Porcine Reproductive and Respiratory Syndrome Virus in Young Pigs". Clinical and Vaccine Immunology, vol. 19, No. 8, Aug. 2012, pp. 1199-1206.
Charerntantanakul et al., "Porcine reproductive and respiratory syndrome virus vaccines: Immunogenicity, efficacy and safety aspects". World Journal of Virology, vol. 1, No. 1, Feb. 2012, pp. 23-30.
Collins et al., "Laboratory diagnosis of porcine reproductive and respiratory syndrome (PRRS) virus infection". Swine Health and Production, vol. 4, No. 1, Feb. 1996, pp. 33-35.
UniProt: Accession No. J9QII1. "SubName: Full=Unglycosylated membrane protein". Nov. 28, 2012, 1 page.
UniProt: Accession No. J9QIW4. "SubName: Full=Polyprotein Iab". Nov. 28, 2012, pp. 1-3.
UniProt: Accession No. J9QHK0. "SubName: Full=Nucleocapsid protein". Nov. 28, 2012, 1 page.
UniProt: Accession No. B4ZUF3. "SubName: Full=Envelope glycoprotein". Sep. 23, 2008, 1 page.
Database EMBL Accession No. EU759247, "Porcine respiratory and reproductive syndrome virus isolate PRRSV2000000079 envelope glycoprotein gene, complete cds". Aug. 10, 2008, 1 page.
Database EMBL Accession No. EF488739, "Porcine respiratory and reproductive syndrome virus isolate MN184C, complete genome". Apr. 19, 2007, pp. 1-4.
Beura et al., "Identification of amino acid residues important for anti-IFN activity of porcine reproductive and respiratory syndrome virus non-stuctural protein 1". Virology, vol. 433, 2012, pp. 431-439.

\* cited by examiner

Figure 1(I)

```
EU LoN94-13 nsp1Beta    SSVYRWKKFVV

Figure 1(II)

```
EU LoN94-13 nsp1Beta    YQTKWGVSGKYLQRRLQVNGIRAVIDPDGPIHVEALSCPQSWIRHLTLDDDVTPGFVRLT  180
delta nsp1 IX-10 nsp1Beta    ............................................................  178
delta nsp1 XVII-1 nsp1Beta   ............................................................  177
delta nsp1 XVIII-12 nsp1Beta ............................................................  176
delta nsp1 XIX-2 nsp1Beta    ............................................................  175
delta nsp1 XX-9 nsp1Beta     ............................................................  174

EU LoN94-13 nsp1Beta    SLRIVPNTEPTTLRIFRFGAHKWYG  205
delta nsp1 IX-10 nsp1Beta    ........................  203
delta nsp1 XVII-1 nsp1Beta   ........................  202
delta nsp1 XVIII-12 nsp1Beta ........................  201
delta nsp1 XIX-2 nsp1Beta    ........................  200
delta nsp1 XX-9 nsp1Beta     ........................  199
```

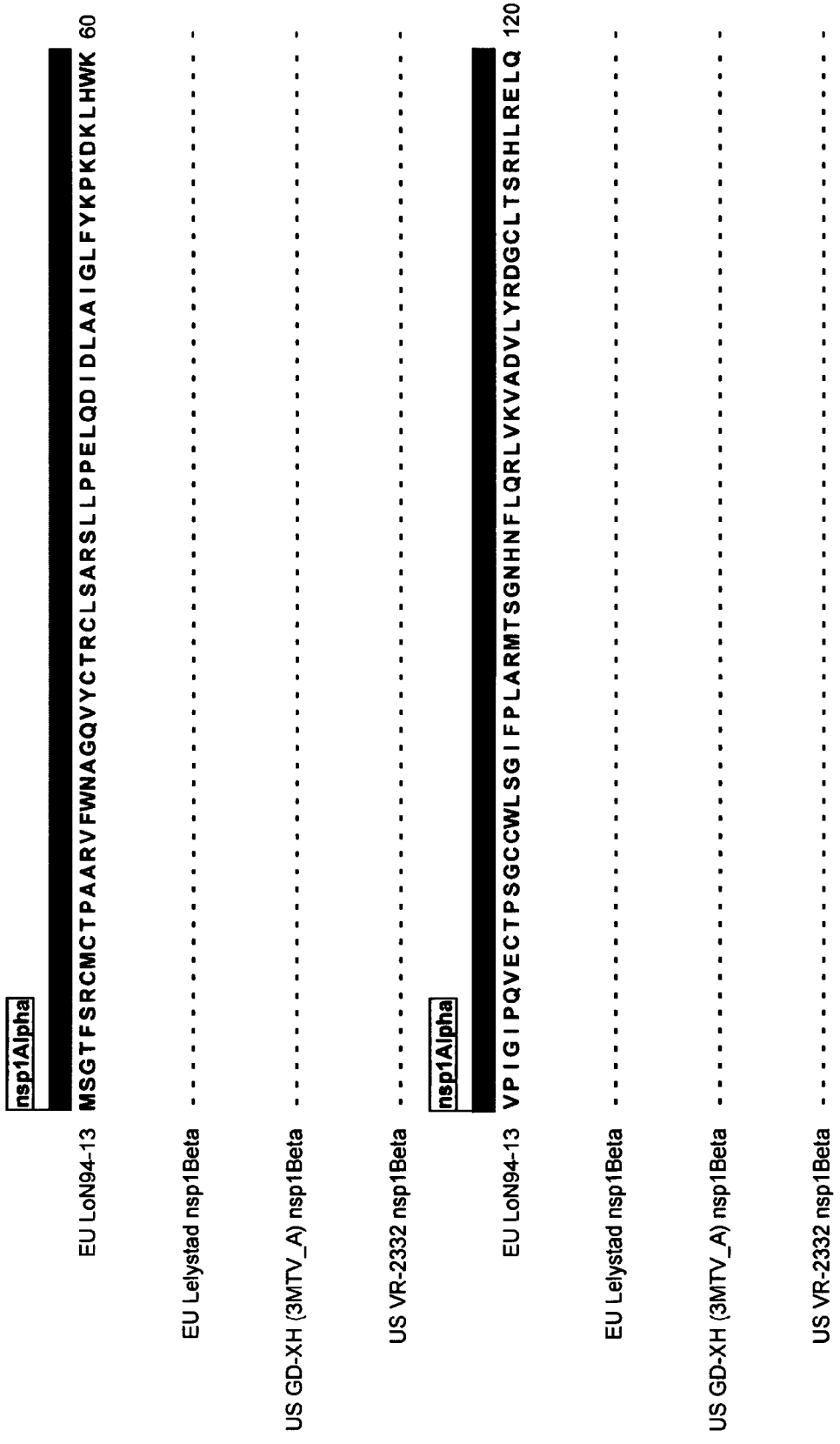

Figure 2(III)

| deletion site |

EU LoN94-13    SSVYRWKKFVVFTDSSPNGR--PRMMWTPESDDSADLEALPPELERQVEILIRSFPAHHP  238
                [nsp1Beta]

EU Lelystad    . . . . . . . . . . . . . . . . . . . . . . . . . . . . . . . . . . . . . . . . . . . . . . . . . . . . . . . . . . . . . . . 58
                                        [P23R24]

US GD-XH (3MTV_A) nsp1Beta    ad..

INFECTIOUS CDNA CLONE OF EUROPEAN PRRS VIRUS AND USES THEREOF

SEQUENCE LISTING

The instant application contains a Sequence Listing which has been submitted electronically in ASCII format and is hereby incorporated by reference in its entirety. Said ASCII copy, created on Aug. 3, 2015, is named 01-2740-US-1-2015-08-14-Updated-SEQ.txt and is 51,309 bytes in size. The full length version of SEQ ID NO: 19 is provided. The CM-EU-9100 as sequence on page 12 of the specification was inadvertently cut off in the table in the WO PDF document. The full length sequence is therefore provided.

BACKGROUND OF THE INVENTION

1. Technical Field

The present invention belongs to the field of animal health and relates to a nucleic acid sequence which comprises the genome of an infectious genotype I (EU) PRRS virus clone. The invention also relates to the use of the nucleic acid sequence of the infectious genotype I PRRS virus clone to study Porcine Reproductive and Respiratory Syndrome (PRRS), a viral disease affecting swine, and in the development of vaccines, therapeutics and diagnostics for the prophylaxis, treatment and diagnosis of PRRS.

2. Background Information

Porcine reproductive and respiratory syndrome virus (PRRSV) is a member of the virus family Arteriviridae and belongs, together with the Coronaviridae, to the virus order Nidovirales. PRRSV is an enveloped virus with a single-stranded, positive-sense RNA genome of about 15 kilobases comprising nine open reading frames (ORFs), namely ORF1a, ORF1ab, ORF2a, ORF 2ab, and ORFs 3 through ORF7. ORFs 1a and 1ab encode large polyproteins that are processed into the viral nonstructural proteins (nsp) by auto- and transcleavages of viral proteases nsp1, nsp2, and nsp4 (Snijder and Meulenberg, 1998).

PRRSV is considered one of the economically most important infectious agents in pigs causing late-term reproductive failure in sows and respiratory disease in growing pigs. Often, PRRSV infection is complicated by secondary bacterial infections being attributed to the immunosuppressive nature of the virus. Also, PRRSV viremia lasts for weeks, and virus then still can be detected in lymphoid organs for several months, demonstrating difficulties or failure of the host's immune response to clear the virus (Allende et al., 2000).

There are two distinct viral PRRSV genotypes causing similar clinical symptoms that diverge by about 40% on nucleotide sequence level, genotype I (EU) and genotype II (US). The North American (US) prototype strain is VR-2332, while the European (EU) prototype strain is Lelystad virus.

A growing number of infectious cDNA clones of the PRRS virus are becoming available to the scientific community, most of which are based on the US type of the virus. For the EU type, however, only one clone is published and has been used for basic research studies whose sequence is derived from Lelystad virus isolated in 1991.

Thus, there is a strong need for new infectious cDNA clones of European (genotype I) PRRS virus, for a better understanding of PRRS, for reproducing said disease in its different forms, for comparative tests, and as platform for the development of new vaccines, medications and diagnostics for the prophylaxis, treatment and diagnosis of PRRS.

DESCRIPTION OF THE INVENTION

The solution to the above technical problem is achieved by the description and the embodiments characterized in the claims.

Thus, the invention in its different aspects and embodiments is implemented according to the claims.

In one aspect, the invention provides a nucleic acid molecule which encodes a genotype I PRRS virus and which is capable of producing infectious virus when transfected into cells, wherein said molecule comprises a nucleic acid sequence having at least 94% sequence identity with the nucleic acid sequence of SEQ ID NO:1, or wherein said nucleic acid molecule comprises or consists of a RNA copy of a nucleic acid sequence having at least 94% sequence identity with the nucleic acid sequence of SEQ ID NO:1. The nucleic acid molecule of the present invention is preferably a DNA molecule. Preferably, said nucleic acid molecule is an isolated nucleic acid molecule.

The term "cells" or "cell", as mentioned herein, is preferably directed to mammalian cells, in particular porcine or simian cells, such as MA-104 cells or MARC-145 cells or Vero cells, more preferably it is understood that the term "cells" or "cell" is directed to the host cells of PRRS virus, namely to porcine macrophages. Hence, a cell, as mentioned herein, is preferably selected from the group consisting of porcine cell, simian cell, MA-104 cell, MARC-145 cell, Vero cell and porcine macrophage.

The term "infectious virus" according to the invention is particularly understood as a PRRS virus which infects swine, causing the associated disease, Porcine reproductive and respiratory syndrome (PRRS).

Said infection of swine by the PRRS virus produced by the nucleic acid molecule of the present invention in particular includes attachment of the virus to a host cell, entry of the virus into the cell, disassembly of the virion, replication and transcription of the viral genome, expression of viral proteins and assembly and release of new infectious viral particles. Said infection of swine by the PRRS virus produced by the nucleic acid molecule of the present invention further preferably includes the transcription of the cDNA sequence to yield a functional RNA molecule, transfection of cultured cells, preferably porcine cell, simian cell, MA-104 cell, MARC-145 cell, Vero cell and porcine macrophage, with said RNA molecule, generation of infectious virions by viral replication in said cultured cells, isolation of such virions and infection of swine.

In particular, the nucleic acid molecule of the present invention encodes a pathogenic genotype I PRRS virus or, respectively, the nucleic acid molecule of the present invention is capable of producing infectious pathogenic virus when transfected into cells.

More particular the nucleic acid molecule of the present invention encodes a genotype 1 PRRS virus which is able to induce Porcine Reproductive and Respiratory Syndrome (PRRS) in swine or, respectively, the nucleic acid molecule of the present invention is capable of producing infectious virus when transfected into cells, wherein said infectious virus is able to induce Porcine Reproductive and Respiratory Syndrome (PRRS) in swine.

In one particular embodiment, the nucleic acid molecule of the present invention encodes a genotype I PRRS virus which is able to induce reproductive symptoms in pregnant sows or, respectively, the nucleic acid molecule of the present invention is capable of producing infectious virus when transfected into cells, wherein said infectious virus is able to induce reproductive symptoms in pregnant sows.

Particularly, the nucleic acid molecule of the present invention encodes a genotype I PRRS virus which is able to induce respiratory symptoms in piglets or, respectively, the nucleic acid molecule of the present invention is capable of producing infectious virus when transfected into cells, wherein said infectous virus is able to induce respiratory symptoms in piglets.

In the context of the PRRS virus as described herein, it is understood that the term "genotype I" is equivalent to the terms "genotype 1" or "type 1" or "European (EU)" as frequently used in the literature in the context of PRRSV.

In another preferred embodiment, the nucleic acid molecule of the present invention comprises a nucleic acid sequence having at least 95%, preferably at least 96%, more preferably at least 97%, still more preferably at least 98%, and in particular preferably at least 99% sequence identity with the nucleic acid sequence set forth in SEQ ID NO:1.

Sequence identity in the context of the invention is understood as being based on pairwise determined similarity between nucleotide sequences. The determination of percent identity between two sequences is preferably accomplished using a mathematical algorithm, in particular the well-known Smith-Waterman algorithm (Smith and Waterman, M. S. (1981) J Mol Biol, 147(1):195-197). For purposes of the present invention, percent sequence identity of a nucleotide sequence is determined using the Smith-Waterman homology search algorithm using a gap open penalty of 25 and a gap extension penalty of 5. The Smith-Waterman homology search algorithm is taught in Smith and Waterman (1981) Adv. Appl. Math 2:482-489, herein incorporated by reference. Such a determination of sequence identity can be performed using, for example, the DeCypher Hardware Accelerator from TimeLogic Version G, or the sequence identity is determined with the software CLC MAIN WORKBENCH 4.1.1 (CLC BIO).

In a further exemplary embodiment, the nucleic acid molecule of the present invention comprises a nucleic acid sequence as set forth in SEQ ID NO:1 with the 14 nucleotide exchanges depicted in the following Table A, namely nucleotide 181 is T instead of C, nucleotide 623 is C instead of A, nucleotide 1561 is C instead of T, and so forth.

TABLE A

Nucleotide exchanges in SEQ ID NO 1 resulting in one preferred embodiment (Sequence "EUX") of the nucleic acid molecule of the present invention.

| region | nt position | SEQ ID NO: 1 | Sequence "EUX" |
|---|---|---|---|
| 5'-UTR | 181 | C | T |
| ORF1a | 623 | A | C |
|  | 1561 | T | C |
|  | 2254 | C | T |
|  | 2549 | T | C |
| ORF1b | 7810 | G | A |
|  | 7822 | G | A |
|  | 10810 | T | C |
|  | 10954 | T | C |
|  | 12892 | A | C |
| ORF6 | 14209 | A | G |
| ORF7 | 14638 | C | T |
|  | 14804 | G | A |
|  | 14909 |  | G |

Thus, compared to the original viral sequence from the field isolate ("EUX"), SEQ ID NO:1 contains the 14 nucleotide exchanges depicted in the above Table A, namely nucleotide 181 is C instead of T, nucleotide 623 is A instead of C, nucleotide 1561 is T instead of C, and so forth.

In a further exemplary embodiment, the nucleic acid molecule of the present invention comprises a nucleic acid sequence as set forth in SEQ ID NO:1, wherein the nucleotide 1561 is C instead of T, nucleotide 2699 is T instead of G, nucleotide 4989 is A instead of T, nucleotide 10817 is T instead of G and nucleotide 14909 is C instead of G (c.f. LoN96 in the Examples).

In a particular preferred embodiment, the nucleic acid molecule of the present invention comprises the nucleic acid sequence of SEQ ID NO:1.

In another preferred embodiment, the nucleic acid molecule of the present invention encodes a genotype I PRRS virus which is not able to induce Porcine Reproductive and Respiratory Syndrome (PRRS) in swine or, respectively, the nucleic acid molecule of the present invention is capable of producing infectious virus when transfected into cells, wherein said infectious virus is not able to induce Porcine Reproductive and Respiratory Syndrome (PRRS) in swine.

As used herein, the term "is not able to induce Porcine Reproductive and Respiratory Syndrome (PRRS)" in particular refers to a reduction of the clinical signs of PRRS or of signs associated with PRRSV infection, respectively, such as elevated body temperature and/or PRRSV viremia, in comparison with a wild type PRRS virus. In one aspect, the genotype I PRRS virus which is not able to induce PRRS induce in swine is thus a virus showing one or more reduced clinical signs, such as a reduced elevation of body temperature, when administered to swine, in comparison with a wild type PRRS virus administered to swine. The term "wild type PRRS virus", as mentioned herein, in particular relates to a wild type genotype I PRRS virus.

The present invention further provides a DNA construct comprising the nucleic acid molecule according to the invention, wherein said DNA construct is in particular a DNA vector such as a plasmid. DNA vectors or plasmids into which the nucleotide molecule of the present invention can be inserted will be recognized by those of ordinary skill in the art. The DNA construct, as described herein, is preferably an isolated DNA construct. As used herein, the term "comprising the nucleic acid molecule" or "comprising a DNA molecule", respectively, is in particular understood to be equivalent to the term "comprising the sequence of the nucleic acid molecule" or "comprising the sequence of a DNA molecule", respectively.

Further, the present invention provides a RNA transcript of the DNA construct described herein, wherein said RNA transcript is preferably an isolated RNA transcript.

The present invention also provides a cell transfected with the DNA construct described herein, wherein said cell is preferably an isolated cell.

Thus, the present invention also provides genotype I PRRS virus produced by the aforementioned cell, wherein said genotype I PRRS virus is preferably an isolated genotype I PRRS virus.

Further, the present invention provides a cell transfected with the RNA transcript mentioned herein, wherein said cell is preferably an isolated cell.

Hence, the present invention also provides genotype I PRRS virus produced by the aforementioned cell, wherein said genotype I PRRS virus is preferably an isolated genotype I PRRS virus.

The present invention further provides a genotype I PRRS virus whose genome comprises the nucleic acid molecule of the present invention or whose genome comprises an RNA molecule encoded by a nucleic acid molecule of the present invention, wherein said genotype I PRRS virus is preferably an isolated genotype I PRRS virus.

In another aspect, the present invention provides a method for producing a genotype I PRRS virus, said method comprising transfecting a cell with the DNA construct described herein.

Moreover, the present invention provides a method for producing a genotype I PRRS virus, said method comprising transfecting a cell with the RNA transcript mentioned herein.

In yet another aspect, the present invention provides a composition, said composition comprising the nucleic acid molecule according to the invention suspended in a suitable amount of a pharmaceutically acceptable diluent or excipient.

Production of the nucleic acid molecules described herein is within the skill in the art and can be carried out according to recombinant techniques described, among other places, in Sambrook et al., 2001, Molecular Cloning, A Laboratory Manual, Cold Spring Harbor Laboratory Press, Cold Spring Harbor, N.Y.; Ausubel, et al., 2003, Current Protocols In Molecular Biology, Greene Publishing Associates & Wiley Interscience, NY; Innis et al. (eds), 1995, PCR Strategies, Academic Press, Inc., San Diego; and Erlich (ed), 1994, PCR Technology, Oxford University Press, New York, all of which are incorporated herein by reference.

In still another aspect, the invention further relates to the use of the nucleic acid molecule according to the invention or of the DNA construct described herein for producing an attenuated genotype I PRRS virus, wherein one or more mutations are introduced into the nucleic acid molecule or into the DNA construct.

The invention also provides a method of producing an attenuated genotype I PRRS virus comprising the step of introducing one or more mutations into the nucleic acid molecule according to the invention or into the DNA construct described herein.

Preferably, the one or more mutations described herein are introduced into the nucleic acid sequence having at least 94% sequence identity with the nucleic acid sequence of SEQ ID NO:1.

The term "attenuated PRRS virus", as described herein, is in particular directed to a PRRS virus which is attenuated in vitro and/or in vivo, more particular in susceptible cell lines and/or the host.

The term "host", as used herein, is in particular directed to animals infectable with PRRS virus, in particular swine, more particular pigs, such as domestic pigs.

As mentioned herein, "attenuated" particularly relates to a reduced virulence of a pathogen, in particular of a wild type PRRS virus, wherein "virulence" is understood to be the degree of pathogenicity, and wherein "pathogenicity" is directed to the ability of the pathogen to produce clinical signs in the host or the offspring of the host, such as elevated body temperature or reproductive failure.

The term "wild type PRRS virus" or "wild type PRRSV", respectively, as used herein, is in particular directed to an infectious pathogenic PRRS virus, which is particularly capable of causing PRRS in swine. In one particular preferred embodiment, the term "wild type PRRS virus" is directed to a PRRS virus whose genome comprises a RNA sequence or consists of a RNA polynucleotide, wherein said RNA sequence or RNA polynucleotide is a RNA copy of SEQ ID NO:1.

The term "body temperature", as used herein, in particular refers to the approximate average normal, internal temperature of an animal, for example about 38.5-39° C. in pigs, whereas the body temperature associated with a PRRSV infection may be elevated up to 41° C. in pigs.

Preferably, the one or more mutations, as described herein, comprise or consist of one or more point mutations and/or one or more genomic deletions and/or one or more insertions.

Also, the invention provides an attenuated genotype I PRRS virus whose genome comprises an RNA molecule encoded by a nucleic acid molecule according to the invention but wherein said nucleic acid sequence having at least 94% sequence identity with the nucleic acid sequence of SEQ ID NO:1 contains one or more mutations that attenuate the encoded PRRS virus, and wherein said attenuated genotype 1 PRRS virus is preferably an isolated attenuated genotype I PRRS virus.

The invention further provides the use of the attenuated genotype I PRRS virus described herein for the preparation of a medicament, in particular of a vaccine or vaccine composition, for preventing an animal from clinical signs of a PRRSV infection, such as by reducing the clinical signs of a PRRSV infection, e.g. reducing the elevated body temperature and/or PRRSV viremia.

The term "preventing" or "reducing", respectively, as used herein, means, but is not limited to, a process which includes the administration of a PRRSV antigen, namely of the attenuated genotype I PRRS virus described herein, to an animal, wherein said PRRSV antigen, when administered to said animal elicits or is able to elicit an immune response in said animal against PRRSV. Altogether, such treatment results in reduction of the clinical signs of PRRS or of signs associated with PRRSV infection, respectively. More specifically, the term "preventing, as used herein, means generally a process of prophylaxis in which an animal is exposed to the immunogenic composition of the present invention prior to the induction or onset of the disease process (PRRS).

Herein, "reducing the clinical signs of a PRRSV infection" means, but is not limited to, reducing the number of infected subjects in a group, reducing or eliminating the number of subjects exhibiting clinical signs of infection, or reducing the severity of any clinical signs that are present in the subjects, in comparison to wild-type infection. For example, it should refer to any reduction of pathogen load, pathogen shedding, reduction in pathogen transmission, or reduction of any clinical sign typical of PRRSV infection, in particular of elevated body temperature or reproductive failure. Preferably these clinical signs are reduced in subjects receiving the attenuated genotype I PRRS virus of the present invention by at least 10% in comparison to subjects not receiving the composition and may become infected. More preferably, clinical signs are reduced in subjects receiving the composition of the present invention by at least 20%, preferably by at least 30%, more preferably by at least 40%, and even more preferably by at least 50%.

Also, the elevated body temperature usually associated with the administration of an attenuated PRRSV vaccine to an animal is reduced in subjects receiving the composition of the present invention by at least 10% in comparison to subjects receiving a conventional attenuated PRRSV vaccine. More preferably, the elevated body temperature usually associated with the administration of an attenuated PRRSV vaccine is reduced in subjects receiving the composition of the present invention by at least 20%, preferably by at least 30%, more preferably by at least 40%, and even more preferably by at least 50%.

The term "subject", as mentioned herein, in particular relates to an animal.

The term "animal", as mentioned herein, is in particular directed to swine, more particular to a pig, preferably a domestic pig.

The term "reducing of PRRSV viremia" means, but is not limited to, the reduction of PRRS virus entering the bloodstream of an animal, wherein the viremia level, i.e. the number of PRRSV RNA copies per mL of blood serum or the number of plaque forming colonies per deciliter of blood serum, is reduced in the blood serum of subjects receiving the composition of the present invention by at least 50% in comparison to subjects not receiving the composition and may become infected. More preferably the viremia level is reduced in subjects receiving the composition of the present invention by at least 90%, preferably by at least 99.9%, more preferably by at least 99.99%, and even more preferably by at least 99.999%.

Also, the invention relates to a vaccine composition comprising the attenuated genotype I PRRS virus described herein suspended in a suitable amount of a pharmaceutically acceptable diluent or excipient.

The one or more pharmaceutically acceptable carriers or excipients, as mentioned herein, are preferably selected from the group consisting of solvents, dispersion media, adjuvants, stabilizing agents, diluents, preservatives, antibacterial and antifungal agents, isotonic agents, and adsorption delaying agents.

In a preferred aspect, the immunogenic composition of the invention comprises an amount of $10^1$ to $10^7$ viral particles of the attenuated genotype I PRRS virus described herein per dose, preferably $10^3$ to $10^6$ particles per dose, more preferably $10^4$ to $10^6$ particles per dose.

In another preferred aspect, the immunogenic composition of the invention comprises an amount of the PRRS virus according to the invention which is equivalent to a virus titre of at least about $10^3$ TCID$_{50}$/mL per dose, preferably between $10^3$ to $10^6$ TCID$_{50}$/mL per dose As used herein, the term "vaccine composition" in particular refers to a composition that will elicit an protective immune response in an animal that has been exposed to the composition. An immune response may include induction of antibodies and/or induction of a T-cell response.

Usually, an "immune response" includes but is not limited to one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number or severity of, or lack of one or more of the clinical signs associated with the infection of the pathogen, in the delay of onset of viremia, in a reduced viral persistence, in a reduction of the overall viral load and/or in a reduction of viral excretion.

Thus, an "immune response" in particular means but is not limited to the development in a subset of a cellular and/or antibody-mediated immune response to the composition or vaccine of interest.

Further, the invention relates to the vaccine composition of the invention for use in a method for preventing an animal from clinical signs of a PRRSV infection, such as by reducing the clinical signs of a PRRSV infection, e.g. reducing the elevated body temperature and/or PRRSV viremia.

Moreover, the invention provides a method for preventing an animal from clinical signs of a PRRSV infection, such as by reducing the clinical signs of a PRRSV infection, e.g. reducing the elevated body temperature and/or PRRSV viremia, wherein said method comprises the step of administering the vaccine of the invention to an animal in need thereof.

EXAMPLES a) Generation of cDNA from a PRRS Virus from a Piglet's Lung

In the work leading to the invention, the generation of the infectious clones was started from a virus strain (EUX) recovered from the lungs of a piglet. Total RNA was extracted from a piglet's lung sample containing a PRRSV virus from a natural field infection, using a standard commercial RNA extraction kit. The viral RNA was reverse transcribed using AMV reverse transcriptase and virus-specific primers. The resulting cDNA was amplified by PCR with a proof-reading DNA polymerase using virus-specific primers and PCR conditions adapted to the expected amplificate length and primers. The primers used for reverse transcription and PCR are depicted in table 1. The resulting PCR products were each about 2 kB in length and contained overlaps with internal restriction sites that could be used for cloning, and additional restriction sites designed into the amplification primers that also formed part of the cloning strategy.

TABLE 1

Primers, RT-PCR product sizes and restriction sites used during the construction of the full-length clone.

|  | primer name | primer sequence | PCR product | cloned fragment |
|---|---|---|---|---|
| RT | EU-1a-4943-as | ACCAGGAGCTCATGGGCCAGGC | 231-2162 | Mun1-EcoRI |
| PCR | EU-1a-221-s | ACGTTCTCCCGGTGCATGTGC | | |
|  | CM-EU-2150as | GCACTCGTCCAGAGACACAGAC | | |
| RT | EU-1a-4943-as | ACCAGGAGCTCATGGGCCAGGC | 1572-3939 | EcoR1-Ssp1 |
| PCR | EU-1a-1562-s | ACTCAGTACAACAGACCAGAGG | | |
|  | CM-EU-3940as | TGCCAAGAATGACACATAAGAGGC | | |
| RT | panPRRSV-1b-as6 | GTRCAAGGKGTSACAGTTTGCC | 3527-5465 | Ssp1-Sph1 |
| PCR | EU-1a-3526-s | GTCCATCAGTCATCGCCTCATGAC | | |
|  | EU-1a-5443-as | AGTGTGCATGCGGTTGTAGGAG | | |
| RT | CM-EU-7805as | CATGACACTATAGGGCACAGTAG | 5323-6712 | Sph1-Apa1 |

TABLE 1-continued

Primers, RT-PCR product sizes and restriction sites used during the construction of the full-length clone.

| primer name | primer sequence | PCR product | cloned fragment |
|---|---|---|---|
| PCR EU-1a-5322-s | ACACCGTGAATGTTGTAGGCTC | | |
| EU-1a-6689-as | ACGTCACCTATGTCAAGGGACGG | | |
| RT CM-EU-7805as | CATGACACTATAGGGCACAGTAG | 6148-7679 | ApaI-SalI |
| PCR EU-1a-6137-s | TCTCTGGCGTTCTACGCACTCGG | | |
| EU-1a-7658-as | CATGCCCTGGTTGAATGCCGG | | |
| RT EU-2-12233-as | GCAAGAATCCGCYTCCACTGC | 7559-9160 | SalI-NruI |
| PCR CM-EU-7560s | CACGCTGTTGTGGCAAACTTAT | | |
| CM-EU-9100as | GGAATTCTGTACAGGCAGCAGACGCAT | | |
| RT EU-2-12233-as | GCAAGAATCCGCYTCCACTGC | 9055-11060 | NruI-MluI |
| PCR CM-EU-9040s | ATCGAAGCAGGGCGACAGCTAGTC | | |
| CM-EU-11025as | TGGTGCCTTTGACATCGCCAATGA | | |
| RT EU-6-14426-as | ACTTCWACGTGRTGGGCAGG | 10777-12990 | MluI-NdeI |
| PCR EU-1b-10777-s | GCGTGGCCTGATCGACTTGTCG | | |
| EU-4-12969-as | AGAAACCAYGATATGTTGAGC | | |
| RT PLR | TCGCCCTAATTGAATAGGTG | 11787-15089 | NdeI-HpaI |
| PCR EU-2-11786-s | ATGCAATGGGGTCACTGTGG | | |
| CM-EU-15150as | TAATTTCGGTCACATGGTTCTCGC | | | b) Cloning of Initial DNA Fragments, Assembly of the Full-Length Clone

Initial PCR products were cloned into the commercial plasmid pBluescript II SK+. The cloned fragments were then assembled into larger fragments by transferring insert sequences from one plasmid to another, using natural internal restriction sites of the cDNA sequence and also the external restriction sites introduced by the PCR amplification primers. No mutations were introduced into the genome for cloning, instead the natural sequence was maintained over the full length of the cDNA clone.

b) Completion of the 5' and 3' Ends and Introduction of Regulatory Sequences

The 3' end of the cDNA was amplified by use of 3'-RACE (Rapid Amplification of cDNA Ends) technology. A commercial RACE kit was used for this purpose. To this end, the antisense primer used for reverse transcription-PCR introduced a restriction site to the very 3' end of the amplified virus-derived sequence, followed by a poly-T-stretch of 60 nucleotides length (SEQ ID NO: 39) that was intended to bind to the poly-A-tail of the viral RNA. The resulting RT-PCR product was re-amplified by a nested PCR and cloned directly into the plasmid that contained the adjacent virus-derived cDNA sequence, yielding a full-length 3' end with a poly-A-tail of 60 residues and a unique restriction site behind this poly-A-tail that could later be utilized for plasmid linearization (for optimized in vitro transcription).

The 5' end of the viral RNA was reverse-transcribed and amplified for sequencing using the RACE technology. Knowing the viral nucleotide sequence, a 5' sense primer was designed that contained a unique restriction site (for cloning) followed by an SP6 promoter sequence, before the first nucleotide of the viral genomic sequence. The RT-PCR product obtained using this primer was then cloned into a plasmid that already contained a subfragment of the adjacent 5' sequence of the virus-derived cDNA, yielding a full-length authentic 5' end preceded by the SPG promoter, the technical prerequisite for in vitro transcription.

d) In Vitro Testing of the First Full-Length Clone LoN82'

The first full-length clone, named LoN82, was tested in cell culture (description of the technique: see below paragraph (f)). The plasmid was linearized and in vitro transcribed using SP6 polymerase. The resulting RNA was transfected into BHK-21 cells using a commercial RNA transfection kit. The supernatant of the transfected cells was transferred to Ma104 cells 24 hours after transfection, and Ma104 were checked daily for the onset of a cytopathic effect (CPE). BHK-21 cells showed a weak staining signal with a PRRSV specific monoclonal antibody 24 hours after transfection, but no CPE was detected on Ma104 cells even after one week of incubation under optimal conditions. Consequently, the full-length clone was non-infectious and analyses were undertaken to determine the reason for this failure.

e) Repair of Mutations in Clone LoN82

In the work leading to the invention, starting from a virus strain (EUX) recovered from the lungs of a piglet, the majority of mutations that had been present in the original full-length clone had been successfully repaired and thereby obtaining a clone named LoN82 which contained only 4 amino acid exchanges in the coding region (and two mutations in the 5'-UTR. However, this clone was found to be non-viable upon transfection in cell culture.

The decision for repairing a selected subset of these mutations was based on the following assumptions:

1. the Two Mutations in the 5'-UTR (Positions 13 and 181 of the Genome):

The 5'-UTR plays a crucial role for the viral replication complex since it contains vital signals for the RNA-dependent RNA polymerase both for full-length and subgenomic RNA synthesis, and possibly other essential signals. The secondary structure of this region is thought to be important for signal recognition. A mutation that influences the structure of the 5'-UTR is likely to impair the functioning of the viral replication machinery. RNA structure predictions performed with the program mfold (Mathews et al., J. Mol. Biol. 288 (911-940, 1999) showed that the C transversion at position 13 may result in such a structural switch, whereas the U→C transition at position 181 does not.

2. the Two Mutations in the Nsp2 Protein (Positions 1561 and 2254 of the Genome):

The non-structural nsp2 protein is the largest protein of PRRSV with 1078 amino acid residues in the EU type, and shares only 32% homology with PRRSV-US. It induces antibodies during natural infection, seems to play a crucial role for viral replication and is thought to have species-specific functions. In the related Equine Arteritis Virus, the C-Terminus was shown to induce architectural changes to membrane compartments of infected cells. Although details remain obscure, it seems clear that the correct functioning of this protein is vital for viral replication.

LoN82 contains two mutations that result in nsp2 amino acid exchanges. Amino acid position 447 lies within the cysteine protease region, which is essential for the processing of the viral polyprotein. The residue itself is conserved in 10 known isolates. It was therefore decided to repair it. On the other hand, the mutation at amino acid position 678 is present in many isolates and lies within a highly variable region that may even be deleted from the genome (e.g. in subclones of the Porcilis PRRS vaccine). This mutation was considered harmless.

3. the Mutation in the RNA-Dependent RNA Polymerase (Position 7797 of the Genome):

The amino acid exchange in ORF1b affects a conserved residue in 5 known isolates. The function of this region is unknown, however, it is far upstream of the essential SDD polymerase motif. Notably, a valine residue is replaced by an alanine, which is a conservative exchange since these two amino acids are often interchangeable. This mutation was therefore considered harmless.

4. the Mutation in the ORF5 (Position 13575 of the Genome):

The mutation in this open reading frame results in an amino acid exchange at position −2 of the signal peptidase cleavage site. Theoretically, the exchange (F for L) should not impair the cleavage of the signal sequence by cellular signalases. However, the phenylalanine residue is conserved in 137 out of 142 known PRRSV-EU sequences, and there is some debate about the biological function of the GP5 signal sequence. It was therefore considered necessary to repair the mutation.

To repair these mutations, the following steps were performed:
a) sub-clone: exchange of the SP6 RNA polymerase promoter for the T7 RNA polymerase promoter and exchange of nucleotide C at position 13 to G by PCR-directed mutagenesis (in one step), resulting in LoN88
b) sub-clone: repair of position 7797 (exchange of T for C) by site-directed mutagenesis resulting in LoN89
c) sub-clone: exchange of nucleotide C at position 13575 for T by site-directed mutagenesis, resulting in LoN86

From these plasmids, a new full-length clone was generated with standard cloning procedures (LoN82+86=LoN90, LoN90+88=LoN93, LoN93+89=LoN94) which was named LoN94. In this clone, position 1561 was repaired from T to C using site-directed mutagenesis, resulting in LoN96.

The clones LoN94 and LoN96 were sequenced, and the result is shown in table 2.

TABLE 2 nucleotide and deduced amino acid exchanges in LoN94 and LoN96

| region | nt position | nucleotides EUX | nucleotides LoN94 | nucleotides LoN96 | amino acids EUX | amino acids LoN94 | amino acids LoN96 |
|---|---|---|---|---|---|---|---|
| 5'-UTR | 181 | T | C | C | | | |
| | 623 | C | A | A | | | |
| ORF1a | 1561 | C | T | | T | M | |
| | 2254 | T | C | C | V | A | A |
| | 2549 | C | T | T | A | | |
| | 2699 | G | | T | S | | |
| | 4989 | T | | A | L | | M |
| ORF1b | 7810 | A | G | G | Q | | |
| | 7822 | A | G | G | K | | |
| | 10810 | C | T | T | R | | |
| | 10817 | G | | T | D | | Y |
| | 10954 | C | T | T | L | | |
| | 12892 | C | A | A | A | | |
| ORF6 | 14209 | G | A | A | L | | |
| ORF7 | 14638 | T | C | | M | T | |
| | 14804 | A | G | G | E | | |
| | 14909 | G | | C | L | | |

In both clones, the mutation at position 13 of the 5' UTR, the A→V mutation in ORF1b and the F→L mutation in ORF5 were repaired. In LoN96, the T→M mutation in ORF1a was also repaired. Unfortunately, both clones had acquired second-site mutations: LoN94 an M→T exchange in ORF7, and LoN96 an L→M exchange in ORF1a and a exchange in ORF1b.

LoN94 M→T [ORF7]: the methionine residue is conserved in 79 out of 82 strains published in Genbank. The other three strains contain valine (2 strains) or leucine. The residue lies at position 17 of the protein, a stretch which may be involved in RNA interaction.

Said mutation was repaired (also named as clone LoN94-13).

LoN96 L→M [ORF1a]: the leucine residue is conserved in the 7 known strain sequences. It lies at amino acid position 131 of the nsp3 coding region, its function is unknown.

LoN96 D→Y [ORF1b]: the asparagic acid residue is conserved in the 8 known strain sequences. It lies at position 58 of the CP3 protein, a protein of unknown function. This residue is outside of the "CVL domain", a stretch which is highly conserved between the arteriviruses.

Since it was impossible to predict the effect of either mutation on a clone's viability, virulence and immunogenicity, therefore both clones were tested in cell culture in order to get a first hint on viral fitness by assessing the growth characteristics.

f) Transfection of BHK-21 and Infection of Ma104 Cells

After in vitro transcription, the in vitro transcribed RNA was purified using sephadex G50 columns, followed by phenol-chloroform extraction. Transfection of BHK-21 cells was carried out according to standard protocols. A plasmid encoding the Green Fluorescent Protein (GFP) served as a positive control since it allowed easy assessment of the transfection efficiency in BHK-21 by determination of the percentage of green cells after 24 hours.

24 hours after transfection, the complete BHK-21 supernatant was transferred to Ma104 cells in 2 aliquots of 500 µl. Cells were incubated at 37° C. and 5% $CO_2$ for 6 days. The cells were checked microscopically (assessment of cytopathic effect) and by immunofluorescence.

Transfection efficiency for the GFP encoding plasmid, as measured by the percentage of green cells, was 40 to 70% in all experiments.

BHK-21 cells transfected with the in vitro transcribed RNA from clone LoN94 showed a strong green staining signal in ~1% of the cells after 24 hours and resulted in a CPE of >50% on Ma104 cells after 6 days. The resulting virus was named BIC97200/94 (EUX/94).

BHK-21 cells transfected with the in vitro transcribed RNA from clone LoN96 showed a strong green staining signal in ~3% of the cells after 24 hours and resulted in a CPE of >50% on Ma104 cells after 4 days. The resulting virus was named BIC97200/96 (EUX/96).

g) Growth Curves of BIC97200/94 (EUX94) and BIC97200/96 (EUX/96) on Ma104 Cells Virus material from different transfections was tested for its growth behaviour on Ma104 cells. The following materials were used
- first passage of three different transfections of LoN96)
- first passage of two different transfections of LoN94
- second passage of one transfection of LoN94
- second passage of the original isolate EUX Ma104 cells were infected with these viruses at an m.o.i. of 0.1. Samples were taken at 0, 24, 48, 72 and 96 hours post infection (except 2. passage of LoN94: 0-72 h). All samples were titrated on Ma104 cells at the same time and were incubated for 6 days. An immunofluorescence assay was carried out.

The growth curves for all transfections with the infectious clones LoN94 (EUX/94) and LoN96 (EUX/96) were highly similar to the growth curve of the wild type virus EUX. There was no indication of growth retardation for either clone-derived virus.

For this reason virus from both clones was amplified in cell culture for a feasibility study in sows. The samples were grown in 75 corn flasks (first passage after transfection).

| EUX/94 | K1A1 | flask 1: | $10^{5.75}$ |
| | | flask 2: | $10^{5.75}$ |
| EUX/96 | K3A | flask 1: | $10^{5.36}$ |
| | | flask 2: | $10^{5.25}$ |
| | K5A | flask 1: | $10^{5.25}$ |
| | K5G | flask 1: | $10^{4.98}$ |
| | | flask 2: | $10^{5.25}$ |

The virus EUX/94 was chosen for an animal study due to its higher and more consistent titres.

h) Animal Studies

Two groups of six (6) PRRSV-negative pregnant gilts were included in the study. Pregnant gilts were at their 90th (±3) day of gestation at the time of inoculation. Animals were treated intramuscularly with $1 \times 10^5$ TCID50/2 ml of the infectious clone (positive control) or with physiological saline (negative control), respectively. Clinical observation, rectal temperature, reproductive performances, and viremia were investigated in the gilts. Transplacental infection rate, weight gain, and survival rate up to weaning at 21 days of age were investigated in piglets. All dead animals were necropsied and tissue samples were collected After inoculation, no increase in rectal temperature above one degree Celsius was observed in any of the groups during the two weeks following the inoculation.

At farrowing, the percentage of live born piglets was 88.75% in the positive control group. Dead piglets at birth in the positive control group reached 11.25% when compared to 3.75% in the negative control group. At weaning, the survival rate was higher in the negative control group (88.31%) than in the positive control group (69,01%).

Four sows from the positive control group were still viraemic at the time of farrowing. By weaning, all gilts turned negative. In all litters from the positive control group at least one piglet was tested viraemic at birth. The mean transplacental infection rate was comprised 64.94% in the positive control group. All litters had viraemic piglets at the time of weaning.

The weight gain over the suckling period in the negative control group and the positive control group were 4.14 kg and 3.51 kg, respectively.

Gilts from the negative control group remained PRRSV negative throughout the study confirming that no break of biosecurity occurred during the study.

Following inoculation with the parental infectious clone, gilts from the positive control group did not show any increase in rectal body temperature. Reproductive performances (88.75% of born alive piglets) were not as severely impaired as usual after challenge of pregnant gilts with virulent EU PRRSV strains (1—Spanish isolate: 43%, 2—Lelystad virus: 76% and 3—Italian-like cluster: 56.6%). Over the suckling period, the survival rate in the positive control group (69.01%) was lower than in the negative control group (88.31%). However, the survival rate at weaning was higher than in other clinical studies (1—Spanish isolate: 20%, 2—Lelystad virus: 36% and 3—Italian-like cluster: 23.3%). In this study in contrast to what was observed in the past, virus derived from the full-length infectious clone demonstrated a low to mild virulence.

It was further shown that the infectious clone may also induce mild respiratory symptoms in piglets.

In the following, the use of the infectious clone (LoN94-13, the resulting virus (EUX/94) is also named virus/strain LoN94-13, hereinafter) for producing an attenuated PRRS virus cantering significant protection from signs of PRRS disease by the introduction of mutations is examplarily described.

In these examples five viable, genetically designed PRRSV mutant strains are described which are based on the infectious EU PRRSV cDNA clone LoN94-13. These strains, delta nsp1 IX-10, delta nsp1 XVII-1, delta nsp1 XVIII-12, delta nsp1 XIX-2 and delta nsp1 XX-9 (henceforth referred to as vaccine candidates), harbor genomic deletions of two, three, four, five, or six codons in their predicted nsp1 genes, respectively, resulting in deletions of two (motif P21R22), three (motif R20P21R22), four (motif G19R20P21R22 (SEQ ID NO: 40)), five (motif N18G19R20P21R22 (SEQ ID NO: 41)), or six (motif (P17N18G19R20P21R22 (SEQ ID NO: 42)) amino acids in their predicted nsp1β proteins, respectively (FIG. 1).

Based on sequence alignments of parental strain LoN94-13 with PRRSV US and EU reference strains VR-2332 and Lelystad virus as well as with strain GD-XH, the deletions are located in the predicted nsp1β portion of nsp1 (FIG. 2). In more detail, the deletion site for all vaccine candidates is located in the N-terminal domain (NTD) of nsp1β and overlaps with aminoacids P23R24 of GD-XH nsp1β; (FIG. 2).

After transfection of synthetic transcripts of the vaccine candidates into BHK21 cells and transfer of cell culture supernatant from transfected BHK21 cells onto PRRSV-susceptible MA104 cells, plaque formation typical for PRRSV infection occurred (data not shown). PRRSV-specificity and viability for each of the vaccine strains then was demonstrated by subsequent cell culture passages on MA104 cells and PRRSV-specific immunofluorescence using monoclonal antibody SDOW17 (Rural Technologies); data not shown.

Figure 3:
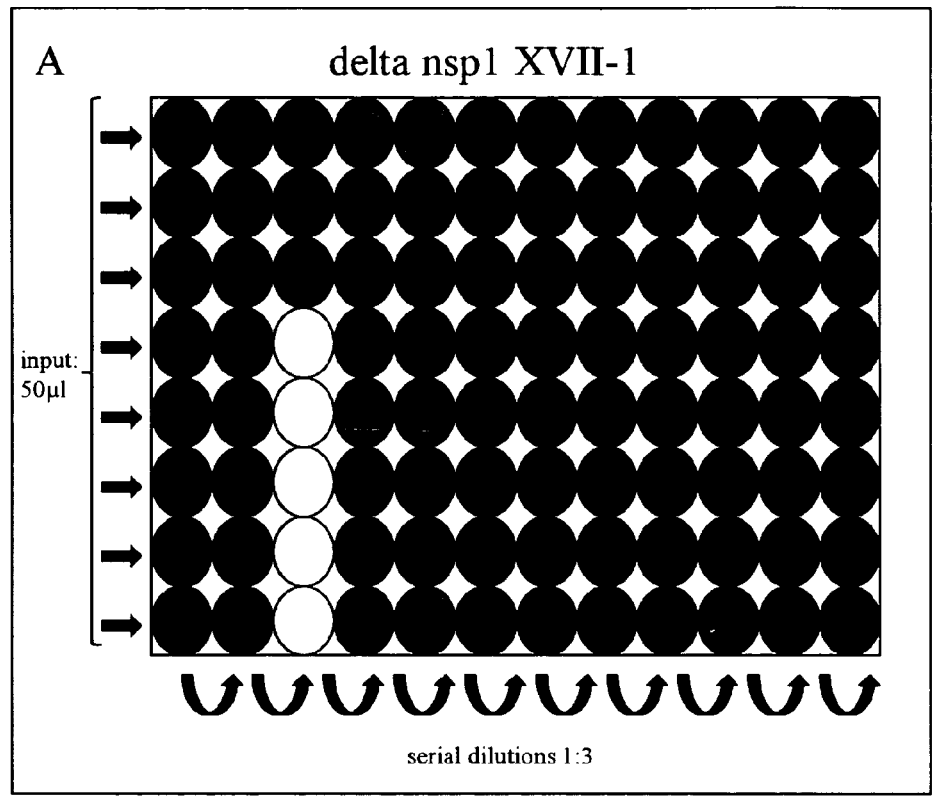
Figure 3:
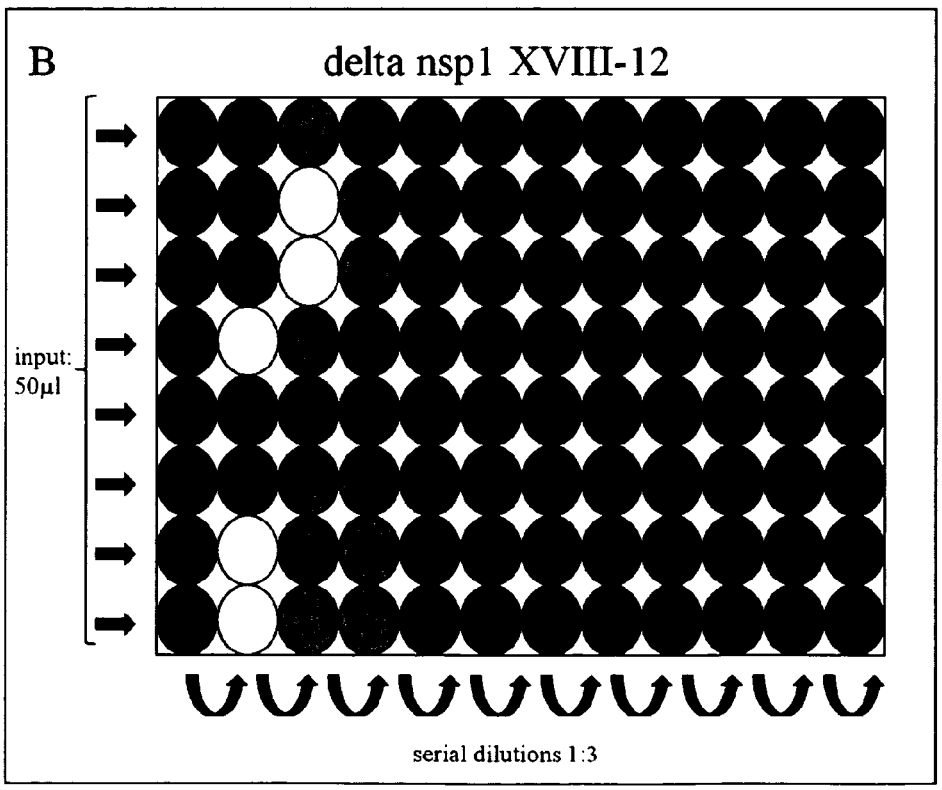

After endpoint dilution and generation of virus stocks each derived from material of a single virus plaque, virus titers of the obtained virus stocks were determined for each vaccine candidate by serial virus titrations on 96-well plates containing MA104 cells followed by PRRSV-specific immunofluorescence analyses six to seven days post infection. Unlike experience with titrations of virus stocks from parental PRRSV LoN94-13 (data not shown), the first serial dilutions of vaccine candidates delta nsp1 XVII-1 and delta nsp1 XVIII-12 did not demonstrate a cytopathic effect and virus plaque formation, while at higher dilutions of the virus stocks a cytopathic effect was detectable. Moreover, when respective titrations were investigated by immunofluorescence, cell culture wells of the first serial dilutions were negative for PRRSV infection for both vaccine candidates, while wells infected with higher dilutions of the virus stocks showed PRRSV-specific immunofluorescence, respectively (FIG. 3).

Figure 4:
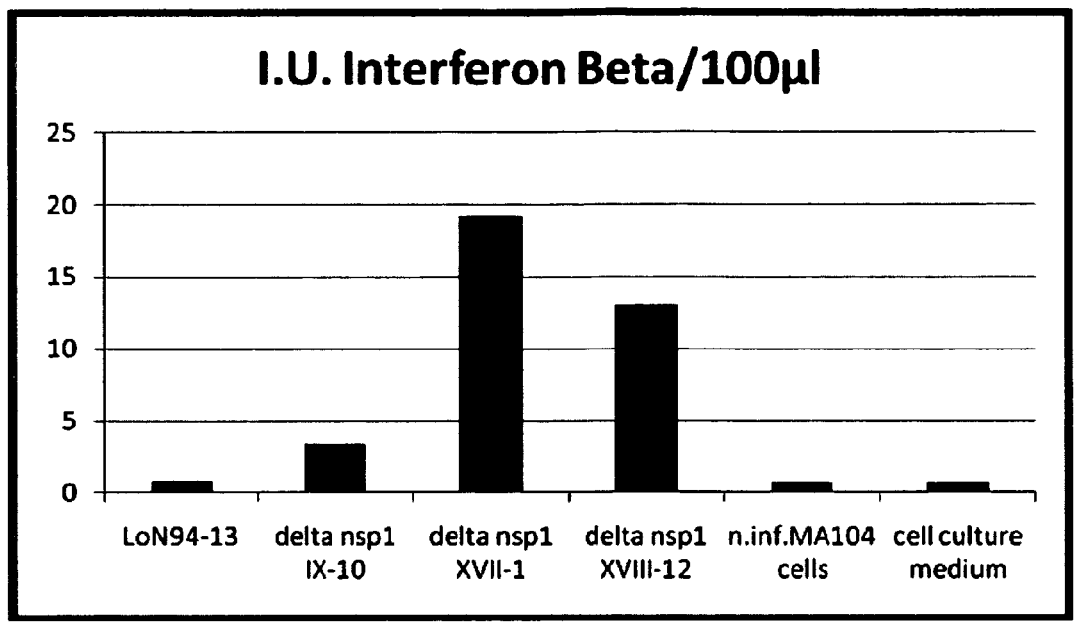

To determine whether the prepared vaccine candidate virus stocks contained type I IFN, a commercial ELISA specific for human IFNβ (Invitrogen) was used. MA104 cells are epithelial Green Monkey kidney cells. According to the ELISA manufacturer, this Invitrogen ELISA is also suited for the detection of primate IFNβ other than human. For each vaccine candidate's virus stock, 100 μl served as assay input, while a virus stock from parental strain LoN94-13, cell culture medium, and medium from noninfected cells served as controls. For quantification of the obtained results, a calibration curve was included using a positive control of the ELISA manufacturer. All samples were measured in duplicates. Unlike the negative controls, virus stocks of the vaccine candidates contained considerable levels of type I IFN, while the virus stock of the parental virus showed IFN levels as low as the negative controls (FIG. 4).

Figure 5:
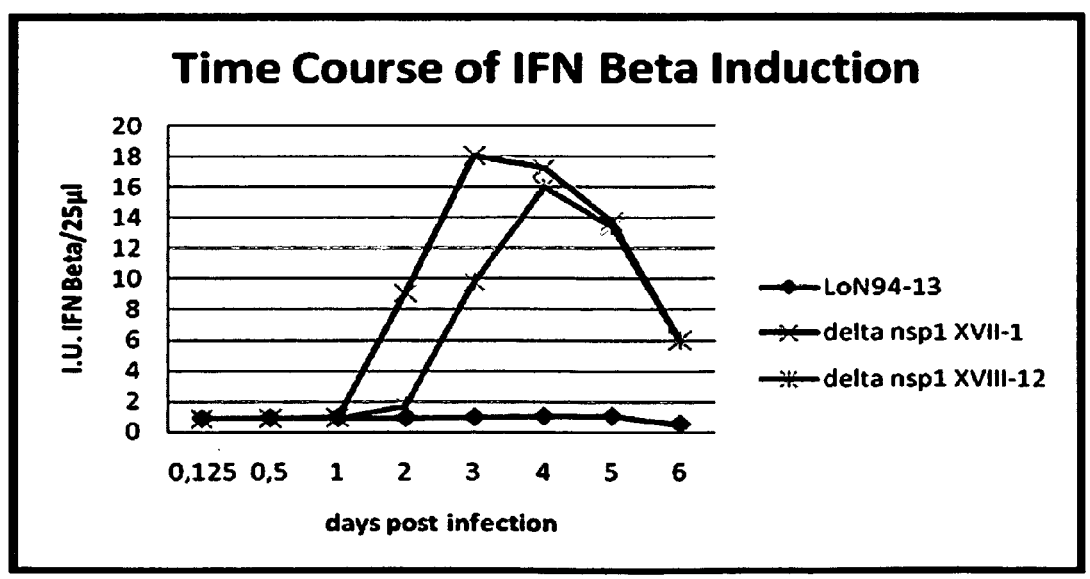

To confirm the results obtained and to assess kinetics of type I IFN production in cells infected with the vaccine candidates, a time course experiment was performed using MA104 cells infected at a multiplicity of infection (MOI) of 0.001, respectively. Parental strain LoN94-13 served as negative control. While there were only very little and unaltered levels of type I IFN near background detectable for infection with parental strain LoN94-13, vaccine candidates delta nsp1 XVII-1 and delta nsp1 XVIII-12 induced considerable and increasing amounts of up to about 18 I.U. IFN 13 per 25 μl sample volume from two days post infection on (FIG. 5).

Figure 6:
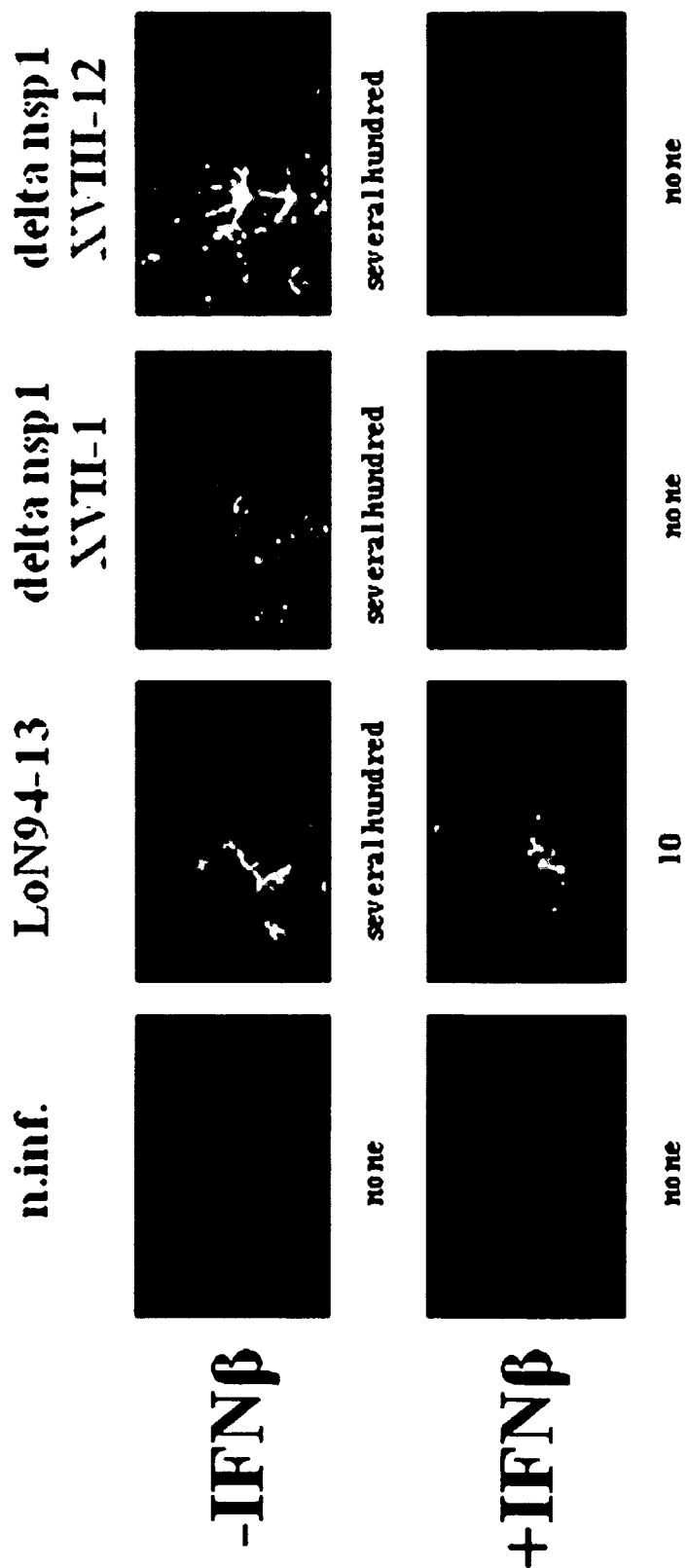

It was experimentally assessed whether vaccine candidates containing genomic deletions in nsp1 demonstrate an increased sensitivity to type I IFN (FIG. 6). $5 \times 10^5$ MA104 cells were seeded into a well of a six-well plate and were either not infected (n.inf.) or infected with 800 infectious virus particles of one of the virus strains given on top, repectively. Cells then were either inoculated with 120 I.U. human IFNβ (+IFNβ, bottom row), respectively, or not (−IFNβ, top row). Three days post infection, immunofluorescence analysis specific for the PRRSV capsid protein was performed using monoclonal antibody SDOW17 (Rural Technologies). The total numbers of foci of PRRSV-infected cells per well are given below, respectively.

This experiment demonstrated that inoculation with type I IFN reduced the number of PRRSV infection events in cells after inoculation with a defined number of infectious virus particles, reflecting reduced viral infectivity of PRRSV when IFN was added. This reduction was 80-fold for wild type virus LoN94-13 (FIG. 6). In addition, for infection with wild type virus, foci of infected cells were smaller than in the well not inoculated with IFN (FIG. 6). However, for vaccine strains delta nsp1 XVII-1 and delta nsp1 XVIII-12, viral infectivity was reduced to zero when INF was added (FIG. 6).

Thus, these vaccine candidates not only induce production of type I IFN in infected cells (FIGS. 4 and 5), but also demonstrate increased sensitivity to type I INF when compared to wild type PRRSV (FIG. 6). This is reflected by their dramatically reduced viral infectivity when IFNβ is present.

Interestingly, the cells infected for the time course experiment summarized in FIG. 5 not only produced considerable amounts of IFNβ, but at the end of the experiment at six days post infection, cells infected with vaccine candidates delta nsp1 XVII-1 and delta nsp1 XVIII-12 showed signs of recovery from usually lytical PRRSV infection. While cells infected with parental strain LoN94-13 were fully lysed, cells infected with the vaccine candidates grew in a partially (delta nsp1 XVII-12) or completely intact monolayer (delta nsp1 XVII-1). For the latter, only weak signs of a PRRSV-induced cytopathic effect were still detectable. Thus, the interferon production of infected cells together with the observed sensitivity of vaccine candidates to type I IFN correlated with partial or almost complete recovery of infected cells over time. It is reasonable to expect that type I IFN induction by the vaccine candidates together with their increased sensitivity to type I IFN will contribute to a significantly attenuated viral phenotype in the natural host. In particular, expected features of the vaccine candidates' attenuation in pigs include stimulation of the innate and specific immunity, both humoral and cellular, and less shedding and/or shortened viremia of the vaccine viruses.

To assess whether the PRRSV vaccine candidates are attenuated in the host, an animal experiment in piglets was performed as described in the following.

Three groups, each of ten animals, were infected at study day 0 either with wild-type parental EU PRRSV strain Lon94-13 (WT group), or with delta nsp1 XVIII-12 (nsp1 group), or were not infected (Ch control group). Infection was applied by intramuscular injection to the neck at dosages of $10^{6,56}$ TCID$_{50}$ for LoN94-13 or $10^{6,6}$ TCID$_{50}$ for delta nsp1 XVIII-12, respectively. 21 days post vaccination, all animals were challenged with a virulent EU PRRSV strain being heterologous to LoN94-13 by intramuscular injection and intranasel inoculation at a total dosage of $3 \times 10^{6,52}$ TCID$_{50}$. Animals were kept until the end of the experiment at day 31, ten days after challenge, and body temperatures were measured for all animals at days 0 (1 and 4 hours post vacciantion), 1, 3, 5, 8, 10, 12, 14, 18, 20, 22, 24, 26, 28, and 31.

Mean body temperatures were determined for each animal for the time after vaccination but before challenge using measured body temperature data from all timepoints from day 0 through day 20. Subsequently, mean body temperatures were determined for each group (FIG. 7, blue (left-hand) columns). Error bars indicate standard deviations, respectively.

Figure 7:
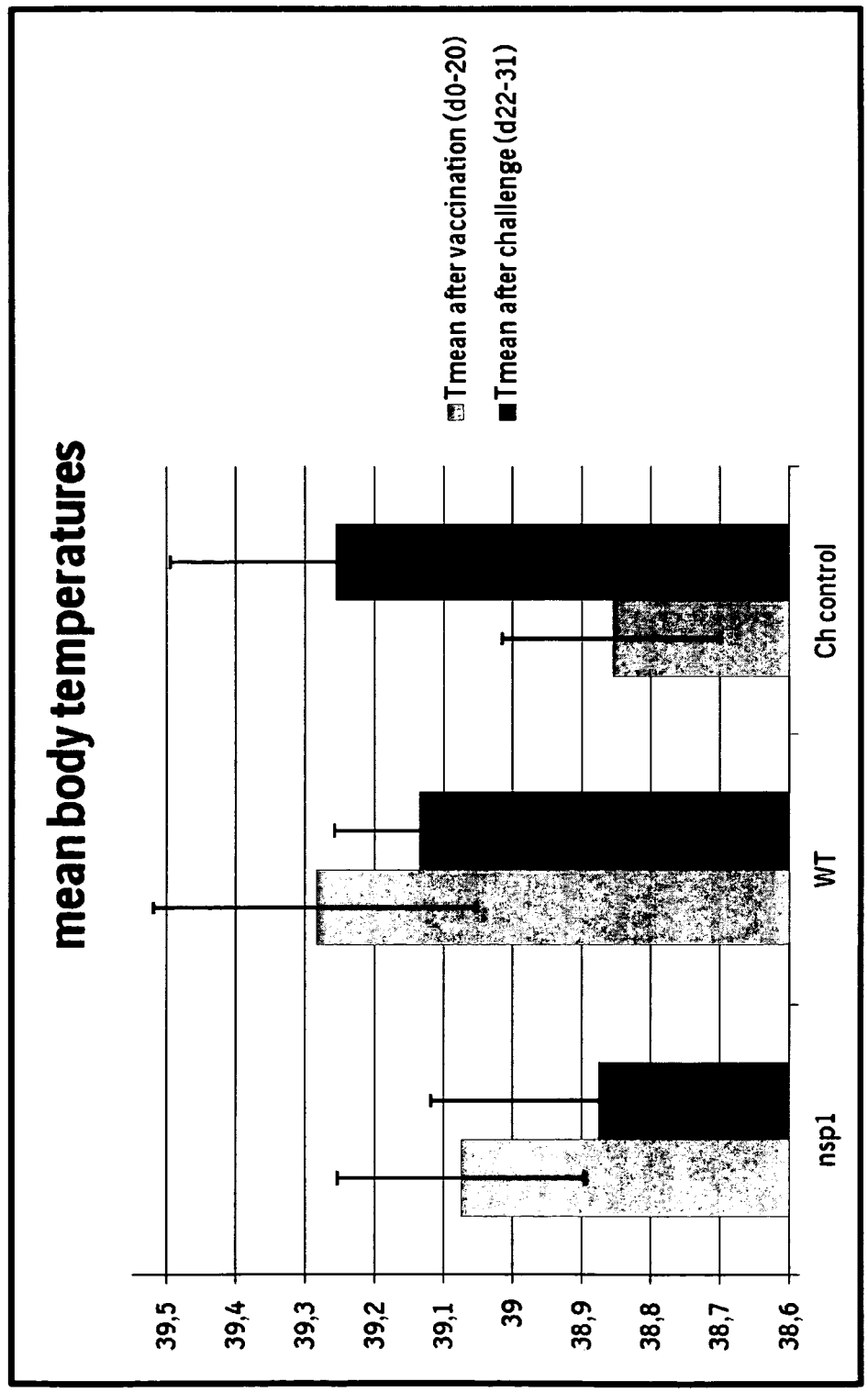

Following the same procedure, mean body temperatures and standard deviations were determined for all groups for the time after challenge using measured body temperature data from all timepoints from day 22 through 31 (FIG. 7, brown (right-hand) columns).

Significant(ly) in the context of the following means either (i) p-values of 0.05 or lower as determined by the Dunnett test and obtained from comparing the nsp1 group with either the WT or the Ch control group for either of the two time periods investigated (before and after challenge) or (ii) p-values of 0.05 or lower when comparing the mean temperature change within a group and between the two time periods investigated (before and after challenge).

When comparing the determined mean body temperatures for the time after vaccination but before challenge (blue columns) in between the three groups, animals from the WT group demonstrated a rise in body temperature of more than 0.4° C. when compared to animals from the noninfected Ch control group, thus demonstrating virulence of LoN94-13 in the infected host.

In contrast, the nsp1 group showed a significant reduction in mean body temperature of more than 0.2° C. when compared to the WT group. Thus, since vaccination dosages were the same for the WT and the nsp1 group, the considerable reduction in increase of body temperature compared to WT demonstrates that the described mutation in the genome of delta nsp1 XVIII-12 has significantly reduced virulence of the WT parental strain LoN94-13 in the infected animal.

The significant rise in the mean body temperature of the Ch control group from before challenge to after challenge of 0.4° C. demonstrates virulence of the heterologous EU PRRSV challenge strain. The mean temperature of the WT group after challenge was slightly lower than before challenge, but not significantly reduced (FIG. 7). In contrast, the mean body temperature of the nsp1 group after challenge was significantly reduced by almost 0.2° C. when compared to that before challenge. Moreover, the body temperature of the nsp1 group after challenge was significantly reduced by almost 0.4° C. when compared to the Ch control group after challenge. Also, mean body temperature of the nsp1 group after challenge was significantly lower that that of the WT group after challenge by more than 0.2° C. Taken together, this demonstrates that a measurable and significant degree of protection from signs of disease induced by the applied challenge virus was conferred to pigs by vaccination with delta nsp1 XVIII-12. Since parental PRRSV strain LoN94-13 did not confer significant protection, it is evident that the described mutation in the genome of delta nsp1 XVIII-12 is causative for the observed significant protective technical effect.

Analogous experiments, wherein the vaccination was performed with lower amounts ($10^5$ $TCID_{50}$) of delta nsp1 XVIII-12 showed results similar to the above described results (data not shown). Thus, in practice, a preferred amount of $10^3$ to $10^5$ $TCID_{50}$ is sufficient for vaccination.

Taken together, the invention described also represents the first known viable PRRSV (EU) strains that contain mutations (deletions) in the nsp1 gene (nsp1β) that induce type I IFN (IFNβ) production in susceptible cells (MA104) and that show increased sensitivity to type I IFN (IFNβ). Moreover, the animal data demonstrates that (i) vaccine candidate delta nsp1 XVIII-12 is significantly attenuated in the host when compared to its parental PRRSV strain LoN94-13 and that (ii) vaccine candidate delta nsp1 XVIII-12 confers significant protection from signs of disease induced by challenge with a heterologous PRRSV strain while parental strain LoN94-13 does not. Thus, the described vaccine candidates or the described mutations therein, either alone or combined with other attenuating mutations, may serve as promising life attenuated PRRSV vaccines.

LIST OF FIGURES

FIG. 1: Sequence alignment of nsp1β protein sequences from parental EU PRRSV strain LoN94-13 (SEQ ID NO: 29) and from vaccine candidates (SEQ ID NOS 30-34, respectively, in order of appearance).

FIG. 2: Sequence alignment of nsp1β proteins from PRRSV strains (SEQ ID NOS 35-38, respectively, in order of appearance).

FIG. 3: PRRSV-specific immunofluorescence of virus stock titrations.

(A) delta nsp1 XVII-1; (B) delta nsp1 XVIII-12.

Black, negative fluorescence; grey, few positive cells; light green, foci of positive cells; dark green, complete cell monolayer positive.

FIG. 4: Virus stocks of vaccine candidates contain IFNβ.

FIG. 5: Time course of IFNβ induction after infection of MA104 cells.

FIG. 6: delta nsp1 mutants show increased sensitivity to type I IFN.

FIG. 7: Mean body temperatures of vaccinated groups before and after challenge.

---

SEQUENCE LISTING

<160> NUMBER OF SEQ ID NOS: 42

<210> SEQ ID NO 1
<211> LENGTH: 15116
<212> TYPE: DNA
<213> ORGANISM: Sus scrofa

<400> SEQUENCE: 1

```
atgatgtgta gggtattccc cctacataca cgacactact agtgtttgtg taccttggag      60
gcgtgggtac agccccgccc caccccttgg cccctgttct agcccaacag gtatccttct     120
ctctcggggc gagtgtgccg cctgctgctc ccttgcagcg ggaaggacct cccgagtatt     180
cccggagagc acctgcttta cgggatcctcc acccttaac catgtctggg acgttctccc     240
ggtgcatgtg cacccggct gctcgggtat tttggaacgc cggccaagtc tattgcacac     300
ggtgtctcag tgcgcggtct cttctccctc cggaacttca ggacattgac ctcgccgcaa     360
ttggcttgtt ttacaagcct aaagacaagc ttcactggaa agtccctatc ggcatccctc     420
aggtggagtg tactccatcc gggtgttgtt ggctctcagg catttttcccc ttagcgcgca     480 tgacctccgg caatcacaac ttcctacaac gacttgtgaa agttgccgat gtgttgtacc     540
```

```
gtgatggttg cttaacttct cgacaccttc gtgaactcca agtttacgag cgtggctgca    600
gctggtaccc aatcacgggg ccagtgcccg ggatgggttt gtacgcaaat tccatgcacg    660
tatctgacca gccgttccct ggtgccaccc atgtgttgac gaactcgcct ttgcctcaac    720
aagcttgtcg gcagccgttc tgcccatttg aggaggctca ttctagcgtg tacaggtgga    780
aaaaatttgt ggtcttcacg gactcctccc ccaacggtcg gcctcgcatg atgtggacgc    840
cggaatccga tgattcagcc gacctagagg cgctaccgcc tgagctagaa cgtcaggtcg    900
aaatcctcat tcggagtttt cctgcccatc accctgtcag cctggccgac tgggagctcg    960
ctgagtcccc tgagaacggt ttttccttca gcacgtacca ttctggtggt tatcttgtcc    1020
aaaaccccga cgtgtttgac agcaagtgct ggctctcctg tttcttggat cagccgatcg    1080
aagtgcgcct ctatgaggat tatctggcta acgctttcgg ttaccaaacc aagtggggcg    1140
tgtctggtaa gtacctccag cgcaggcttc aagtcaacgg tattcgtgct gtaatcgatc    1200
ctgatggccc cattcacgtt gaagcgctgt cttgccccca atcttggatc aggcacctga    1260
ctctggacga tgacgtcacc ccaggattcg ttcgcctaac atccctccgc attgtgccga    1320
acacagagcc cactactctc cgaatctttc ggtttggagc gcataagtgg tatggcgctg    1380
ccggcaaacg ggctcgtgcc aagcgtgccg ctaaaagtga aagggtccg gctcccactc     1440 ccaaggttgc cccgccagcc ccacctgcg gaattgttac ctactctcca ccaacagacg     1500
ggtcttgcgg ttggcacgtc cttgccgcca taatgaaccg aatgatgaac ggtgacttca    1560
tgtcccctct ggcccagtac aacagaccag aggatgattg gcttctgat tacgatcttg     1620 cccaggcgat tcaatgtctg cggttgcctg ctaccatagt tcggaatcgt gcctgtccca    1680
acgccaagta cctcataaaa ctcaacggag tccactggga ggtagaggtg aggtcaggga    1740
tggcccctcg ctcccttccc cgcgagtgcg tagtcggcgt ttgttccgaa ggctgtgccg    1800
catcgcctta cccagaaaac gggctaccta acgagcgtt tgaggccttg cgtctgctt     1860 acagactacc ttccgattgt gtcagttctg gtattgctga cttcttgct aaccccctc     1920 aggaattctg gactcttgac aaaatgttga cctccccgtc accggagcgg tctggttttt    1980
ccagtctgta caaattgcta ttagaggttg tcccgcagaa atgcggagcc acggaagggg    2040
cttttaccta tgctgttgag agaatgctga aggattgccc gagctccgaa caggccatgg    2100
cccttctggc aaaaattaaa gttccatcct caaaggcccc gtctgtgtcc ctggacgagt    2160
gtttccctac ggatgtttca gccgatttcg aaccagcatc tcaggagagg tcccaaaatt    2220
ccagcgctgc tgttgtcctg cattcaccga atgcaaaaga gttcgaggaa gcagctccag    2280
gggaagttca ggagggtggc cacaaggccg tccactctgc actccctgcc ggggtccta    2340 acaataagca ggcacagctg gttgccggtg agcaactgaa gctcggcggt tgtggttcgg    2400
tagttgggaa tgcacatgaa ggtgttctgg tcccacctgg tccaattaat ttgacaagcg    2460
gggatttacc ctcctcaggc tccatgaaag aagatatgct caatagccgg gaggacgaac    2520
cactggattt gtcccaacca gcaacagctg tcacaacgac tcttatggga gagctaacac    2580
ccgactacct aggttctgat actggtgccc tccccgtcac cgtccgaaaa tttgtcccga    2640
cggggcctat actccgtcat gttgagcact gcagcacggg gtcgggcgat agcagttcgc    2700 cttttggatct gtctggtgcg caaaccccgg accagccttt aaatctgtcc ctggcggctt    2760
ggccagtgag gaccaccgcg tctgatcctg ctgggtcca cggtagacgc gagcctgtct     2820
ttgtaaagcc tcgagatgtt ttctctgatg gcgattcagc ccttcagttc ggggagcttt    2880
ctgaatccag ctctgtcatc gagtttgatc gggcaaaaga tgctcaggtg gctgacgccc    2940
```

-continued

```
ctgtcggtct gacgacttcg gacgaggccc tctccgcagt cgatcctttc gagttttccg    3000
aactcaagcg cccacgtttc tccgcacaag ccttaattga ccgaggcggc ccacttgccg    3060
atgtccatgc aaaaataaag aaccgggtat atgaacagtg cctccaagct tgtgagcccg    3120
gtagtcgcgc aaccccagct accagggagt ggctcgacaa aatgtgggag agagtggaca    3180
tgaaaacctg gcgctgcacc tcacagttcc aagctggtca cattcttgcg tccctcaaat    3240
tcctccctga catgattcaa gacacaccgc tcctgttcc caggaagaac cgagccagtg     3300
ataaagctgg cctgaaacaa ctagtggcac agtgggatag agattgagt tcaaccccccc    3360
ccccaaaacc ggttgggccg gtacttgacc gggtcgatcc tccgcctacg ggtacccggc    3420
aagaagacgt cacccctcc gatgggccac ccatgcgcc ggatggtcga gtgagtacgg      3480
gtgggagttg gaaaggcctt atgctttccg gcacccgtct cacggggtcc atcagtcatc    3540
gcctcatgac atgggttttt gaagttgtct cccatctccc agcttttatg ctcacacttt    3600
tctcgccgcg gggctctatg gctccaggcg attgggtttt gcaggtgtt gttttacttg     3660
ctctcctgct ctgtcgttct tacccaatat tcgggtgcct tcccttattg ggtgtctttt    3720
ctggtactgt gcgcgtgtt cgtctgggtg ttttttggctc ttggatggct tttgctgtat    3780
ttttattctc gactccatcc aacccagtcg gttcttcttg taaccacgat tcgccggagt    3840
gtcatgctga gcttctggct cttgagcagc gccaactttg ggaacctgtg cgcggccttg    3900
tggtcggccc atcgggcctc ttatgtgtca ttcttggcaa gttactcggt gggtcacgtt    3960
atctctggca tgttctccta cgtctatgcc tgcttcaga tttggcccttt tctcttgttt    4020
atgtggtgtc ccagggcgt tgtcacaagt gttggggaaa gtgtataagg acagctcctg    4080
ctgaggtggc ttttaatgta tttccttct cgcgcgccac ccgtagttct cttgtatcct    4140
tatgtgatcg attccaaacg ccaaaaggag ttgatcccgt gcacttggcg acaggttggc    4200
gcgggtgctg gcgtggtgag agtcctatcc atcaaccaca ccaaaagccc atagcttacg    4260
ccaatttgga tgaaaagaag atatctgccc aaacggttgt tgctgtccca tacgatccca    4320
atcaggctat caaatgtctg aaagttctgc aggcgggagg ggctatcgtg gatcagccta    4380
cgcctgaggt cgttcgtgtg tccgagatcc ccttctcagc cccatttttc ccaaaagttc    4440
cagtcaaccc agattgtagg gtcgtggtgg attcggacac ttttgtggct gcggttcgtt    4500
gtggttattc gacatcacaa ctggtcctgg gccagggcaa ctttgccaag ttaaatcaaa    4560
ccccccccag gaactctatc tccaccaaag cgactggtgg ggcctcttat acttttgctg    4620
tggctcaagt gtctgtgtgg acccttgttc atttcgtcct cggtctttgg ctcacgtcac    4680
ctcaagtgtg tggtcgagga accgctgacc catggtgttc aagtccattt tcatatccta    4740
cctatggccc cggggttgtg tgctcctctc gactttgtgt gtctgctgac ggggtcaccc    4800
ttccattgtt ctcagccgtg gcacaactct ctggtaggga ggtgggatt tttatttag     4860
tgctcgtctc ctttattgcc ttggcccacc gcatggctct taaggcagac atgttagtag   4920
tcttttttggc tctttgtgct tatgcctggc ccatgagctc ctggttgatc tgcttcttc    4980
ctatactctt gaggtgggtt acccttcacc ctctcactat gctttgggtg cattcattct   5040
tgatgtttttg tctcccagca gccggcgtcc tctcactggg gataactggc ctcctctggg   5100
caatcggccg ctttactcag gttgccggaa tcattacacc ttatgatatc caccagtaca   5160
cctctgggcc acgtggtgca gccgctgtgg ccacagcccc agaaggcact tacatggccg   5220
ccgtccggag agctgcttta accgggcgga cttttaatct tcaccccgtcc gcagttggat  5280
```

```
cccttctcga aggtgctttc aggactcata accoctgcct taacaccgtg aatgtcgtag    5340
gctcctccct tggttccgga ggggttttca ccattgacgg aaaaaaaatt gtcgtcactg    5400
ctgcccatgt gctgaacggc gacacagcta gagtcaccgg tgattcctac aaccgcatgc    5460
acactttcaa gactaatggt gactatgcct ggtccatgc tgataactgg cagggcgctg    5520
cccctgtggt caaggttgcg aaagggtatc gcggtcgtgc ctactggcaa acatcaactg    5580
gtgtcgagcc tggtgttatt gggaatgggt tcgccttctg tttcaccaac tgcggcgatt    5640
cggggtcacc cgttatctca gaatctggtg atcttatcgg aatccacacc ggttcaaaca    5700
aacttggttc tggtcttgtg acaaccctg aaggggagac ctgtaccatc agagaaacca    5760
agctttctga cctttccaga catttcgcag gcccaagcgt tcctcttggg gacatcaaat    5820
tgagtccggc catcatccct gatgtgacat ccattccgag tgacttggca tcgctcctag    5880
cttccgtccc tgtaatggaa ggcggcctct cgaccgttca acttttgtgt gtcttttccc    5940
tcctctggcg catgatgggc catgcctgga cgcccattgt tgccgtgggc ttcttttgc    6000
tgaatgaaat tcttccagca gttttggttc gagccgtgtt ttcttttgca ctctttgtgc    6060
ttgcatgggc cacccctgg tctgcacaag tgttgatgat tagacttctc acggcatctc    6120
tcaaccgcaa caaactttct cttgcgttct acgcactcgg aggtgttgtt ggtttggctg    6180
ctgaaatcgg gacttttgct ggtaaattgt ctgaattgtc tcaagctctt tcgacatact    6240
gtttcttacc tagggtcctt gctatgacca gctgtgttcc catcatcatc attggtggac    6300
tccatgccct cggtgtgatt ctgtggttat tcaaataccg gtgcctccac aacatgctgg    6360
ttggtgatga aagcttttca agcgctttct tcctacggta ttttgcagag ggcaatctca    6420
ggagaggtgt ttcacagtcc tgtggcatga gtaacgagtc cctgacggct gctttggctt    6480
gcaagttgtc acaggctgac cttgattttt tgtccagctt aacgaacttc aagtgctttg    6540
tatctgcttc aaacatgaaa aatgctgccg ccagtacat tgaagcagct tatgccaggg    6600
ccctgcgtca agagttggcc tctttagtcc agattgacaa aatgaaagga gttttgtcca    6660
agctagaggc ctttgctgaa acggccactc cgtccctcga cgtaggtgac gtgattgttc    6720
tacttggaca acatcctcac ggatccgttc tcgatattaa tgtggggact gaaaggaaaa    6780
ctgtatccgt gcaagagacc cggagcctag gcggctccaa gttcagtgtt tgtactgttg    6840
tgtcaaacac acccgtggac gccttagccg gtattccact ccagacacca acccccttt    6900
tcgagaatgg cccgcgtcat cgcagcgagg aggacgatct taaagtcgag aggatgaaga    6960
aacactgcgt gtccctcggc ttccacaaca ttaacggtaa agtttactgc aagatttggg    7020
acaagtctac cggtgacgcc ttttacactg atgattcccg gtacacccaa gactatgctt    7080
ttcaggacag gtcagctgac tatagagaca gggactacga gggtgtgcaa accgcccccc    7140
aacagggatt tgatccaaag tctgaaaccc ctgttggtac cgttgtgatc ggcggtatta    7200
cgtacaacag gtatttggtc aaaggtaagg aggttctggt tcccaagcct gacaactgcc    7260
ttgaagctgc caagctgtcc cttgagcaag ctctcgctgg gatgggccaa acttgtgacc    7320
ttacagctgc cgaggtggaa aagctaaagc gcatcattgg tcaacttcaa ggattgacca    7380
ctgagcaggc tttaaactgt tagccgccag cggcttgacc cgctgtggcc gcggcggcct    7440
agttgtaact gaaacggcgg taaaaattgt caaataccac agcagaactt ttaccttagg    7500
ctctttagac ctaaaagtca cttccgaggt ggaggtgaag aagtcaaccg agcagggcca    7560
cgctgttgtg gcaaacttgt gttctggtgt cgtcttgatg agacctcacc caccgtccct    7620
tgtcgacgtt cttctgaaac ccggacttga cataacaccc ggcattcaac cagggcatgg    7680
```

```
ggccgggaat atgggcgtgg acggttccat ttgggatttt gaaaccgcac ccacaaaggc   7740
tgaactcgag ttatccaagc aaataattca agcatgtgaa gtcaggcgcg gggatgcccc   7800
gaacctccag ctcccttaca agctctatcc tgttagaggg gatcctgagc ggcataaagg   7860
ccacctcatc aataccaggt ttggagactt accttacaaa actcctcaag acaccaagtc   7920
cgcaatccac gcggcttgtt gcctgcaccc caacggggcc ccgtgtctg atggtaaatc    7980 cacactaggt accactcttc aacatggctt cgagctttat gtccctactg tgccctatag   8040
tgtcatggag taccttgatt cacgcccaga caccccttt atgtgcacta aacacggcac    8100
ttccaaggct gctgcagagg acctccaaaa atacgaccta tccacccaag gatttgtcct   8160
gcctggggtc ctacgcctag tgcgcaggtt catctttggc acattggca aggcaccgcc     8220 attgttcctc ccatcaactt atcccgccaa gaactccatg gcaggtatta atggtcagag   8280
gttcccaaca aaggatgttc aaagtatacc tgaaattgat gaaatgtgtg cccgcgccgt   8340
caaggagaat tggcaaactg tgacaccttg caccctcaag aaacagtatt gttctaggcc   8400
caaaaccagg accatcctgg gcactaacaa cttcatagcc ttggctcata gatcggcgct   8460
cagtggtgtt acccaggcat tcatgaagaa ggcttggaag tccccaatag ccttagggaa   8520
aaacaaattc aaggagctgc attgcactgt cgctggcagg tgcctcgagg ccgacttggc   8580
ttcctgtgac cgcagcaccc ctgccattgt gaggtggttc actacccacc tcctatatga   8640
acttgcagga tgtgaagaat atctacctag ctatgtgctt aactgttgcc atgaccttgt   8700
ggcgacgcag gatggtgctt tcacaaaacg cggtggcctg tcgtctggag acccagtcac   8760
cagtgtgtcc aacactgtgt actcactggt gatttatgcc cagcacatgg tactatctgc   8820
cctgaaaatg ggtcatgaaa ttggcctcaa gttcctcgaa gaacaactca atttgagga    8880 ccttcttgaa atccagccta tgttagtata ctctgatgat cttgtcttgt acgcagaaaa   8940
gcccaccttc cccaactatc attggtgggt cgagcatctt gacctgatgt tgggctttaa   9000
aacggaccca agaaaaccg tcataactga taaacccagt ttcctcgggt gcagaatcga    9060
agcagggcga cagctagtcc ccaatcgcga ccgcatcctg gctgctcttg catatcacat    9120
gaaggcgcag aacgcctcag agtattatgc gtctgctgcc gcaatcctga tggattcatg   9180
tgcttgcatt gaccacgatc ctgaatggta tgaggacctc atctgtggca ttgcccgatg   9240
cgctcgcctg gacggttata gctttccagg tccggcattt ttcatgtcca tgtgggagaa   9300
gctgaggagt cataatgaag ggaagaaatt ccgccactgc ggcatctgcg acgccaaagc   9360
cgactacgcg gctgcttgtg ggcttgattt gtgtttgttt cattcgcact ttcaccaaca   9420
ctgccctgtc actctgagct gcggtcacca tgccggttcg aaggaatgtt cgcagtgtca   9480
gtcacctgtt ggggccggca gatcccctct tgatgctgtg ctggaacaaa ttccatacaa   9540
acctcctcgc actgtcatca tgaaggtggg taataaaaca acggcccttg atccggggag   9600
gtaccagtcc cgtcgaggtc tcgttgcagt caagaggggt attgcgggta atgaagttga   9660
tcttgctgat ggagattacc aagtggtacc tcttctgccg acttgcaaag atataaacat   9720
ggtgaaggtg gcttgcaacg tactactcag caagttcata gtagggccac caggttccgg   9780
gaagaccacc tggctactaa gtcaagttca ggacgatgat gtcatttaca cacccactca   9840
tcagaccatg tttgacatag ttagtgctct caaagtttgc aggtattcca ttccaggagc   9900
ctcgggactc ccttttccac cgcctgccag gtccggccg tgggttaggc tcattgccag     9960
cgggcacgtc cctggccgag tatcatacct cgatgaggcc ggatattgca atcatctgga  10020
```

```
cattcttaga ctgctttcca aaacacccct tgtgtgtttg ggtgaccttc agcaacttca   10080
cccagtcggc tttgattcct attgttatgt gttcgatcag atgcctcaga agcagttgac   10140
caccatttac agatttggcc ccaacatctg cgcagccatc cagccttgtt acagggagaa   10200
acttgaatct aaggctagga acaccagggt ggttttacc acccggcctg tggcctttgg    10260
ccaggtgctg acaccatatc acaaagatcg cgtcggctcc gcgattacca tagactcatc   10320
ccagggggcc acctttgaca ttgtaacatt gcatctacca tcgccaaagt ccctaaataa   10380
gtcccgggca cttgtggcca tcacacgggc aagacacggg ttgttcattt atgaccctca   10440
caaccagctc cgggagtttt tcaacctaac ccctgagcgc actgattgta accttgtgtt   10500
cagccgtgga gatgagctgg tggtcctgaa tgcagataat gcagtcacaa ccgtggcgaa   10560
ggccttagag acaggtccaa ctcaatttcg agtgtcagac ccgaggtgca agtctctctt   10620
agccgcttgc tcggccagtc tggaagggag ctgcatgccg ctaccgcaag tggcgcataa   10680
cctggggttt tacttctccc cagacagtcc agtatttgca cctctgccaa aagagttggc   10740
gccacattgg ccagtggtta cccatcagaa taatcgggcg tggcctgatc gacttgtcgc   10800
tagtatgcgt ccaattgacg cccgctacag caagccgatg gtcggtgcag ggtatgtggt   10860
cggaccgtcc accttccttg gtactcctgg agtggtgtca tactatctca cactatacat   10920
caggggtgag ccccaggcct tgccagaaac acttgtttca acaggacgta tagccacaga   10980 ttgtcggag tatctcgacg cggctgagga agaggcagca aaagaacttc cccacgcgtt    11040
cattggcgat gtcaaaggca ccacagttgg ggggtgtcat cacattacat caaaataccct  11100 acctaggtcc ctgcctaaag actctgttgc cgtagttgga gtaagttcgc ctggcagggc   11160
tgctaaagcc gtatgcaccc tcaccgatgt gtacctccct gaactccggc catatctgca   11220
acctgagacg gcatcaaaat gctggaaact caaattagac ttcagggacg tccgactaat   11280
ggtctggaaa ggagccaccg cctactttca attggaaggg ctcacatggt cggcgctgcc   11340
tgactatgcc aggtttattc agctgcccaa aaacgctgtt gtatacatcg atccgtgcat   11400
aggaccggca acagccaatc gtaaagtcgt acgaaccaca gattggcggg ccgacctggc   11460
agtgacgccg tatgattacg gtgcccggaa cattttgaca acagcctggt tcgaggacct   11520
cgggccgcag tggaagattc tggggttgca gcccttagg cgggcgtttg gctttgaaaa    11580
cactgaggat tggcaatcc ttgcatgctg catgagtgac ggcaaggact acactgacta    11640
taactggaat tgcgttcgac aacgcccaca cgctatccat ggacgcgctc gtgaccatac   11700
gtaccacttt gcccctggca ctgaattgca agtggagctc ggtaaacccc ggctgccacc   11760
tgagcaagta ccgtgaattc ggagtgatgc aatgggtca ctgtggagta aaatcagcca    11820
gctgttcgtg gacgccttca ctgaattcct tgttagtgtg gttgatattg tcatcttcct   11880
tgccatattg tttgggttca ccgtcgcagg atggttactg gtctttcttc tcagagtggt   11940
ttgctccgcg cttctccgtt cgcgctctgc cattcactct tccgaactat cgaaggtcct   12000
atgagggctt actacctaat tgcagaccgg atgttccaca atttgcattt aagcacccct   12060
tgggtatgtt ttggcacatg cgggtttccc acctaattga tcagatggtc tctcgccgca   12120
tctaccagac catggaacat tcaggtcaag cggcctggaa gcacgtggtc agtgaggcta   12180
ctcttacaaa attgtcagaa ctcgacatag ttctccactt ccaacacctg gccgcagtgg   12240
aggcggactc ttgtcgcttc ctcagctcac gacttgtgat gctgaaaaat cttgccgttg   12300
gcaatgtgag cttgcagtac aacaccacgt tgaaccgcgt tgagctcatc ctccccacac   12360
caggtacgag gcccaaattg accgatttca gacaatggct catcagtgtg cacgcttcca   12420
```

```
tttttcctc tgtagcctca tcagttactt tgttcatagt gctttggctt cgaattccag    12480
ccgtacgcta tgttttggt ttccattggc ccatggcaac acgtcattcg agctgaccat    12540
taattacact atatgcatgc cctgtcttac cagccaagcg gctcaacaaa ggctcgaacc    12600
cggtcgtaac atgtggtgca aaataggaca caccacgtgc gaggagcgtg accatgatga    12660
gttgtcaatg tccatcccgt ccgggtacga caacctcaaa cttgaaggtt attacgcttg    12720
gctggctttt ttgtcctttt cctacgcggc ccaattccat ccggagttgt ttggaatagg    12780
gaatgtgtcg cgcgtctttg tggataaacg acaccagttc atttgtgccg agcatgacgg    12840
agataattca accgtatcta ccggacacaa catctccgca tcatatgcgg catattatca    12900
ccaccaaata gacgggggca attggttcca tttggaatgg ctgcggccgc tcttttcctc    12960
ttggctagtg ctcaacatat catggtttct gaggcgttcg cctgcaagcc ctgtttctcg    13020
acgcatctat cagatattaa gaccaatacg accgcggctg ccggtttcat ggtccttcaa    13080
gacatcagtt gcctccgacc tcacagggtc tcagcatcgc aagagaacat tcccttcgga    13140
aagtcgtcac aatgtcgtga agccgtcggt actccccagt acattacgat gactgctaat    13200
gtgaccgacg aatcatattt gtacaacgcg gacttgctaa tgcttccgc gtgccttttc    13260 cacgcctcag aaatgagcga gaaaggcttc aaagttatct ttggaaacgt ctccggcgtt    13320
gtttcagctt gtgtcaattt cacagattat gtggcccatg taaccaaca tacccaacag    13380 catcatctgg taattgatca cattcggtta ctgcatttcc tgacaccatc tgcaatgagg    13440
tgggctacaa ccattgcttg tttgttcgcc attctcttag cgatatgaga tgttctcaca    13500
aattggggcg tttcttgact ccgcactctt gcttctggtg gctttttttg ctgtgtaccg    13560
gcttgtcctg gtccttttgcc gatggcaacg gcaacagctc gacacgccaa tacatatata    13620
acttgacgat atgcgagctg aatgggaccg tctggttgtc cagtcatttt gattgggcag    13680
tcgagacctt tgtgctttac ccggtggcca ctcatatcct ctcactgggt tttctcacaa    13740
caagccattt ttttgatgcg ctcggtctcg gcgctgtgtc cactacggga tttcttggcg    13800
ggcggtatgt acttagcagc gtgtacggcg cctgcgcctt cgcagcgctt gtatgttttg    13860
tcatccgtgc tgctaaaaat tgcatggctt gccgttatgc ccgcacccgg ttcaccaact    13920
tcatcgtgga cgaccggggg aagatccatc gatggaagtc cccaatagtg gtagagaaat    13980
taggcaaagc tgacatcggc ggcgaccttg tcaccatcaa acatgttgtc ctcgaaggag    14040
tcaaagctca acctttgacg aggacatcgg cggagcaatg ggaagcctag atgattttg    14100 caatgatcct accgccgcac agaagcttgt gctggcattt agtatcacat acacacctat    14160
aatgatatac gccctcaagg tgtcacgcgg ccggctccta ggactgttac acatcctgat    14220
atttctgaac tgttctttca cgttcggata catgacatac gtgcactttc aatccactaa    14280
ccgtgtcgcg cttactatgg gggcggtcgt tgccctttg tggggcattt acagctttat    14340
agaatcatga agtttgtca cttccagatg caggttgtgt tgcctaggcc ggcgatacat    14400
tctggcccct gcccaccacg tagaaagtgc tgcaggcctc cattcaatcc cagcgtctgg    14460
taaccgagca tacgctgtga gaaagcccgg actaacatca gtgaacggca ctctagtacc    14520
aggacttcgg agcctcgtgt tgggcggcaa acgagctgtt aaacgaggag tggttaacct    14580
cgtcaagtat ggccggtaaa accagagcc agaagaaaaa gaaaaacaca gctcctatgg    14640
ggagtggcca gccagtcaat caactgtgcc aattgctggg cacaatgata aagtcccagc    14700
gccagcggcc tagggagga caggccaaaa tgaaaaagcc tgagaagcca catttcccc    14760
```

```
tagctgctga agatgacatc cggcaccatt tcacccagac cgagcgttcc ctttgcttgc    14820
aatcgatcca gacggccttc aatcaaggcg caggaactgc gtcgctttca tccagcggga    14880
aggtcagttt tcaggttgag ttcatgctgc cggtcgctca tacggtgcgc ctgattcgcg    14940
taacttccac atccgccagt cagggtgcaa gttaatttga tagttaggtg aatggccgcg    15000
attggcgtgt ggcctctgag tcacctattc aattagggcg atcacatggg ggttagactt    15060
aattggcgag aaccatgtga ccgaaattaa aaaaaaaaaa aaaaaaaaaa aaaaaa        15116

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
accaggagct catgggccag gc                                              22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acgttctccc ggtgcatgtg c                                               21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcactcgtcc agagacacag ac                                              22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
accaggagct catgggccag gc                                              22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
actcagtaca acagaccaga gg                                              22

<210> SEQ ID NO 7
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgccaagaat gacacataag aggc                                              24

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtrcaaggkg tsacagtttg cc                                                22

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtccatcagt catcgcctca tgac                                              24

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agtgtgcatg cggttgtagg ag                                                22

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
catgacacta tagggcacag tag                                               23

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acaccgtgaa tgttgtaggc tc                                                22

<210> SEQ ID NO 13
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acgtcaccta tgtcaaggga cgg                                            23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
catgacacta tagggcacag tag                                            23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tctctggcgt tctacgcact cgg                                            23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
catgccctgg ttgaatgccg g                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcaagaatcc gcytccactg c                                              21

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cacgctgttg tggcaaactt at                                             22

<210> SEQ ID NO 19
<211> LENGTH: 37
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 19
ggaattctgt acaggcagca gacgcataat actctga         37

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
gcaagaatcc gcytccactg c         21

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
atcgaagcag ggcgacagct agtc         24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
tggtgccttt gacatcgcca atga         24

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
actttcwacg tgrtgggcag g         21

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
gcgtggcctg atcgacttgt cg         22

<210> SEQ ID NO 25
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 25
agaaaccayg atatgttgag c                                              21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tcgccctaat tgaataggtg                                                20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atgcaatggg gtcactgtgg                                                20

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
taatttcggt cacatggttc tcgc                                           24

<210> SEQ ID NO 29
<211> LENGTH: 205
<212> TYPE: PRT
<213> ORGANISM: Porcine reproductive and respiratory syndrome virus

<400> SEQUENCE: 29

Ser Ser Val Tyr Arg Trp Lys Lys Phe Val Val Phe Thr Asp Ser Ser
1               5                   10                  15

Pro Asn Gly Arg Pro Arg Met Met Trp Thr Pro Glu Ser Asp Asp Ser
            20                  25                  30

Ala Asp Leu Glu Ala Leu Pro Pro Glu Leu Glu Arg Gln Val Glu Ile
        35                  40                  45

Leu Ile Arg Ser Phe Pro Ala His His Pro Val Ser Leu Ala Asp Trp
    50                  55                  60

Glu Leu Ala Glu Ser Pro Glu Asn Gly Phe Ser Phe Ser Thr Tyr His
65                  70                  75                  80

Ser Gly Gly Tyr Leu Val Gln Asn Pro Asp Val Phe Asp Ser Lys Cys
                85                  90                  95

Trp Leu Ser Cys Phe Leu Asp Gln Pro Ile Glu Val Arg Leu Tyr Glu
            100                 105                 110

Asp Tyr Leu Ala Asn Ala Phe Gly Tyr Gln Thr Lys Trp Gly Val Ser
        115                 120                 125
```

```
Gly Lys Tyr Leu Gln Arg Arg Leu Gln Val Asn Gly Ile Arg Ala Val
            130                 135                 140

Ile Asp Pro Asp Gly Pro Ile His Val Glu Ala Leu Ser Cys Pro Gln
145                 150                 155                 160

Ser Trp Ile Arg His Leu Thr Leu Asp Asp Val Thr Pro Gly Phe
                165                 170                 175

Val Arg Leu Thr Ser Leu Arg Ile Val Pro Asn Thr Glu Pro Thr Thr
                180                 185                 190

Leu Arg Ile Phe Arg Phe Gly Ala His Lys Trp Tyr Gly
            195                 200                 205
```

<210> SEQ ID NO 30
<211> LENGTH: 203
<212> TYPE: PRT
<213> ORGANISM: Porcine reproductive and respiratory syndrome virus

<400> SEQUENCE: 30

```
Ser Ser Val Tyr Arg Trp Lys Lys Phe Val Phe Thr Asp Ser Ser
1               5                   10                  15

Pro Asn Gly Arg Met Met Trp Thr Pro Glu Ser Asp Asp Ser Ala Asp
                20                  25                  30

Leu Glu Ala Leu Pro Pro Glu Leu Glu Arg Gln Val Glu Ile Leu Ile
            35                  40                  45

Arg Ser Phe Pro Ala His His Pro Val Ser Leu Ala Asp Trp Glu Leu
50                  55                  60

Ala Glu Ser Pro Glu Asn Gly Phe Ser Phe Ser Thr Tyr His Ser Gly
65                  70                  75                  80

Gly Tyr Leu Val Gln Asn Pro Asp Val Phe Asp Ser Lys Cys Trp Leu
                85                  90                  95

Ser Cys Phe Leu Asp Gln Pro Ile Glu Val Arg Leu Tyr Glu Asp Tyr
            100                 105                 110

Leu Ala Asn Ala Phe Gly Tyr Gln Thr Lys Trp Gly Val Ser Gly Lys
        115                 120                 125

Tyr Leu Gln Arg Arg Leu Gln Val Asn Gly Ile Arg Ala Val Ile Asp
    130                 135                 140

Pro Asp Gly Pro Ile His Val Glu Ala Leu Ser Cys Pro Gln Ser Trp
145                 150                 155                 160

Ile Arg His Leu Thr Leu Asp Asp Val Thr Pro Gly Phe Val Arg
                165                 170                 175

Leu Thr Ser Leu Arg Ile Val Pro Asn Thr Glu Pro Thr Thr Leu Arg
            180                 185                 190

Ile Phe Arg Phe Gly Ala His Lys Trp Tyr Gly
        195                 200
```

<210> SEQ ID NO 31
<211> LENGTH: 202
<212> TYPE: PRT
<213> ORGANISM: Porcine reproductive and respiratory syndrome virus

<400> SEQUENCE: 31

```
Ser Ser Val Tyr Arg Trp Lys Lys Phe Val Phe Thr Asp Ser Ser
1               5                   10                  15

Pro Asn Gly Met Met Trp Thr Pro Glu Ser Asp Asp Ser Ala Asp Leu
                20                  25                  30

Glu Ala Leu Pro Pro Glu Leu Glu Arg Gln Val Glu Ile Leu Ile Arg
            35                  40                  45
```

```
Ser Phe Pro Ala His His Pro Val Ser Leu Ala Asp Trp Glu Leu Ala
     50                  55                  60

Glu Ser Pro Glu Asn Gly Phe Ser Phe Ser Thr Tyr His Ser Gly Gly
 65                  70                  75                  80

Tyr Leu Val Gln Asn Pro Asp Val Phe Asp Ser Lys Cys Trp Leu Ser
                 85                  90                  95

Cys Phe Leu Asp Gln Pro Ile Glu Val Arg Leu Tyr Glu Asp Tyr Leu
             100                 105                 110

Ala Asn Ala Phe Gly Tyr Gln Thr Lys Trp Gly Val Ser Gly Lys Tyr
         115                 120                 125

Leu Gln Arg Arg Leu Gln Val Asn Gly Ile Arg Ala Val Ile Asp Pro
130                 135                 140

Asp Gly Pro Ile His Val Glu Ala Leu Ser Cys Pro Gln Ser Trp Ile
145                 150                 155                 160

Arg His Leu Thr Leu Asp Asp Val Thr Pro Gly Phe Val Arg Leu
                 165                 170                 175

Thr Ser Leu Arg Ile Val Pro Asn Thr Glu Pro Thr Thr Leu Arg Ile
                 180                 185                 190

Phe Arg Phe Gly Ala His Lys Trp Tyr Gly
             195                 200

<210> SEQ ID NO 32
<211> LENGTH: 201
<212> TYPE: PRT
<213> ORGANISM: Porcine reproductive and respiratory syndrome virus

<400> SEQUENCE: 32

Ser Ser Val Tyr Arg Trp Lys Lys Phe Val Val Phe Thr Asp Ser Ser
 1               5                  10                  15

Pro Asn Met Met Trp Thr Pro Glu Ser Asp Asp Ser Ala Asp Leu Glu
                 20                  25                  30

Ala Leu Pro Pro Glu Leu Glu Arg Gln Val Glu Ile Leu Ile Arg Ser
             35                  40                  45

Phe Pro Ala His His Pro Val Ser Leu Ala Asp Trp Glu Leu Ala Glu
         50                  55                  60

Ser Pro Glu Asn Gly Phe Ser Phe Ser Thr Tyr His Ser Gly Gly Tyr
 65                  70                  75                  80

Leu Val Gln Asn Pro Asp Val Phe Asp Ser Lys Cys Trp Leu Ser Cys
                 85                  90                  95

Phe Leu Asp Gln Pro Ile Glu Val Arg Leu Tyr Glu Asp Tyr Leu Ala
             100                 105                 110

Asn Ala Phe Gly Tyr Gln Thr Lys Trp Gly Val Ser Gly Lys Tyr Leu
         115                 120                 125

Gln Arg Arg Leu Gln Val Asn Gly Ile Arg Ala Val Ile Asp Pro Asp
130                 135                 140

Gly Pro Ile His Val Glu Ala Leu Ser Cys Pro Gln Ser Trp Ile Arg
145                 150                 155                 160

His Leu Thr Leu Asp Asp Val Thr Pro Gly Phe Val Arg Leu Thr
                 165                 170                 175

Ser Leu Arg Ile Val Pro Asn Thr Glu Pro Thr Thr Leu Arg Ile Phe
                 180                 185                 190

Arg Phe Gly Ala His Lys Trp Tyr Gly
         195                 200

<210> SEQ ID NO 33
```

```
<211> LENGTH: 200
<212> TYPE: PRT
<213> ORGANISM: Porcine reproductive and respiratory syndrome virus

<400> SEQUENCE: 33

Ser Ser Val Tyr Arg Trp Lys Lys Phe Val Val Phe Thr Asp Ser Ser
1               5                   10                  15

Pro Met Met Trp Thr Pro Glu Ser Asp Ser Ala Asp Leu Glu Ala
            20                  25                  30

Leu Pro Pro Glu Leu Glu Arg Gln Val Glu Ile Leu Ile Arg Ser Phe
        35                  40                  45

Pro Ala His His Pro Val Ser Leu Ala Asp Trp Glu Leu Ala Glu Ser
65      50                  55                  60

Pro Glu Asn Gly Phe Ser Phe Ser Thr Tyr His Ser Gly Gly Tyr Leu
65              70                  75                  80

Val Gln Asn Pro Asp Val Phe Asp Ser Lys Cys Trp Leu Ser Cys Phe
            85                  90                  95

Leu Asp Gln Pro Ile Glu Val Arg Leu Tyr Glu Asp Tyr Leu Ala Asn
            100                 105                 110

Ala Phe Gly Tyr Gln Thr Lys Trp Gly Val Ser Gly Lys Tyr Leu Gln
            115                 120                 125

Arg Arg Leu Gln Val Asn Gly Ile Arg Ala Val Ile Asp Pro Asp Gly
        130                 135                 140

Pro Ile His Val Glu Ala Leu Ser Cys Pro Gln Ser Trp Ile Arg His
145             150                 155                 160

Leu Thr Leu Asp Asp Val Thr Pro Gly Phe Val Arg Leu Thr Ser
            165                 170                 175

Leu Arg Ile Val Pro Asn Thr Glu Pro Thr Thr Leu Arg Ile Phe Arg
            180                 185                 190

Phe Gly Ala His Lys Trp Tyr Gly
            195                 200

<210> SEQ ID NO 34
<211> LENGTH: 199
<212> TYPE: PRT
<213> ORGANISM: Porcine reproductive and respiratory syndrome virus

<400> SEQUENCE: 34

Ser Ser Val Tyr Arg Trp Lys Lys Phe Val Val Phe Thr Asp Ser Ser
1               5                   10                  15

Met Met Trp Thr Pro Glu Ser Asp Ser Ala Asp Leu Glu Ala Leu
            20                  25                  30

Pro Pro Glu Leu Glu Arg Gln Val Glu Ile Leu Ile Arg Ser Phe Pro
        35                  40                  45

Ala His His Pro Val Ser Leu Ala Asp Trp Glu Leu Ala Glu Ser Pro
    50                  55                  60

Glu Asn Gly Phe Ser Phe Ser Thr Tyr His Ser Gly Gly Tyr Leu Val
65              70                  75                  80

Gln Asn Pro Asp Val Phe Asp Ser Lys Cys Trp Leu Ser Cys Phe Leu
            85                  90                  95

Asp Gln Pro Ile Glu Val Arg Leu Tyr Glu Asp Tyr Leu Ala Asn Ala
            100                 105                 110

Phe Gly Tyr Gln Thr Lys Trp Gly Val Ser Gly Lys Tyr Leu Gln Arg
        115                 120                 125

Arg Leu Gln Val Asn Gly Ile Arg Ala Val Ile Asp Pro Asp Gly Pro
    130                 135                 140
```

```
Ile His Val Glu Ala Leu Ser Cys Pro Gln Ser Trp Ile Arg His Leu
145                 150                 155                 160

Thr Leu Asp Asp Asp Val Thr Pro Gly Phe Val Arg Leu Thr Ser Leu
                165                 170                 175

Arg Ile Val Pro Asn Thr Glu Pro Thr Thr Leu Arg Ile Phe Arg Phe
            180                 185                 190

Gly Ala His Lys Trp Tyr Gly
            195
```

<210> SEQ ID NO 35
<211> LENGTH: 389
<212> TYPE: PRT
<213> ORGANISM: Porcine reproductive and respiratory syndrome virus

<400> SEQUENCE: 35

```
Met Ser Gly Thr Phe Ser Arg Cys Met Cys Thr Pro Ala Ala Arg Val
1               5                   10                  15

Phe Trp Asn Ala Gly Gln Val Tyr Cys Thr Arg Cys Leu Ser Ala Arg
            20                  25                  30

Ser Leu Leu Pro Pro Glu Leu Gln Asp Ile Asp Leu Ala Ala Ile Gly
        35                  40                  45

Leu Phe Tyr Lys Pro Lys Asp Lys Leu His Trp Lys Val Pro Ile Gly
50                  55                  60

Ile Pro Gln Val Glu Cys Thr Pro Ser Gly Cys Cys Trp Leu Ser Gly
65                  70                  75                  80

Ile Phe Pro Leu Ala Arg Met Thr Ser Gly Asn His Asn Phe Leu Gln
            85                  90                  95

Arg Leu Val Lys Val Ala Asp Val Leu Tyr Arg Asp Gly Cys Leu Thr
            100                 105                 110

Ser Arg His Leu Arg Glu Leu Gln Val Tyr Glu Arg Gly Cys Ser Trp
        115                 120                 125

Tyr Pro Ile Thr Gly Pro Val Pro Gly Met Gly Leu Tyr Ala Asn Ser
    130                 135                 140

Met His Val Ser Asp Gln Pro Phe Pro Gly Ala Thr His Val Leu Thr
145                 150                 155                 160

Asn Ser Pro Leu Pro Gln Gln Ala Cys Arg Gln Pro Phe Cys Pro Phe
            165                 170                 175

Glu Glu Ala His Ser Ser Val Tyr Arg Trp Lys Lys Phe Val Val Phe
            180                 185                 190

Thr Asp Ser Ser Pro Asn Gly Arg Pro Arg Met Met Trp Thr Pro Glu
        195                 200                 205

Ser Asp Asp Ser Ala Asp Leu Glu Ala Leu Pro Pro Glu Leu Glu Arg
    210                 215                 220

Gln Val Glu Ile Leu Ile Arg Ser Phe Pro Ala His His Pro Val Ser
225                 230                 235                 240

Leu Ala Asp Trp Glu Leu Ala Glu Ser Pro Glu Asn Gly Phe Ser Phe
            245                 250                 255

Ser Thr Tyr His Ser Gly Gly Tyr Leu Val Gln Asn Pro Asp Val Phe
            260                 265                 270

Asp Ser Lys Cys Trp Leu Ser Cys Phe Leu Asp Gln Pro Ile Glu Val
        275                 280                 285

Arg Leu Tyr Glu Asp Tyr Leu Ala Asn Ala Phe Gly Tyr Gln Thr Lys
    290                 295                 300

Trp Gly Val Ser Gly Lys Tyr Leu Gln Arg Arg Leu Gln Val Asn Gly
```

```
                305                 310                 315                 320
Ile Arg Ala Val Ile Asp Pro Asp Gly Pro Ile His Val Glu Ala Leu
                    325                 330                 335

Ser Cys Pro Gln Ser Trp Ile Arg His Leu Thr Leu Asp Asp Val
                340                 345                 350

Thr Pro Gly Phe Val Arg Leu Thr Ser Leu Arg Ile Val Pro Asn Thr
            355                 360                 365

Glu Pro Thr Thr Leu Arg Ile Phe Arg Phe Gly Ala His Lys Trp Tyr
370                 375                 380

Gly Ala Ala Gly Lys
385

<210> SEQ ID NO 36
<211> LENGTH: 384
<212> TYPE: PRT
<213> ORGANISM: Porcine reproductive and respiratory syndrome virus

<400> SEQUENCE: 36

Met Ser Gly Thr Phe Ser Arg Cys Met Cys Thr Pro Ala Ala Arg Val
1               5                   10                  15

Phe Trp Asn Ala Gly Gln Val Tyr Cys Thr Arg Cys Leu Ser Ala Arg
            20                  25                  30

Ser Leu Leu Pro Pro Glu Leu Gln Asp Ile Asp Leu Ala Ala Ile Gly
        35                  40                  45

Leu Phe Tyr Lys Pro Lys Asp Lys Leu His Trp Lys Val Pro Ile Gly
    50                  55                  60

Ile Pro Gln Val Glu Cys Thr Pro Ser Gly Cys Cys Trp Leu Ser Gly
65                  70                  75                  80

Ile Phe Pro Leu Ala Arg Met Thr Ser Gly Asn His Asn Phe Leu Gln
                85                  90                  95

Arg Leu Val Lys Val Ala Asp Val Leu Tyr Arg Asp Gly Cys Leu Thr
            100                 105                 110

Ser Arg His Leu Arg Glu Leu Gln Val Tyr Glu Arg Gly Cys Ser Trp
        115                 120                 125

Tyr Pro Ile Thr Gly Pro Val Pro Gly Met Gly Leu Tyr Ala Asn Ser
    130                 135                 140

Met His Val Ser Asp Gln Pro Phe Pro Gly Ala Thr His Val Leu Thr
145                 150                 155                 160

Asn Ser Pro Leu Pro Gln Gln Ala Cys Arg Gln Pro Phe Cys Pro Phe
                165                 170                 175

Glu Glu Ala His Ser Ser Val Tyr Arg Trp Lys Lys Phe Val Val Phe
            180                 185                 190

Thr Asp Ser Ser Leu Asn Gly Arg Ser Arg Met Met Trp Thr Pro Glu
        195                 200                 205

Ser Asp Asp Ser Ala Ala Leu Glu Val Leu Pro Pro Glu Leu Glu Arg
    210                 215                 220

Gln Val Glu Ile Leu Ile Arg Ser Phe Pro Ala His His Pro Val Asp
225                 230                 235                 240

Leu Ala Asp Trp Glu Leu Thr Glu Ser Pro Glu Asn Gly Phe Ser Phe
                245                 250                 255

Asn Thr Ser His Ser Cys Gly His Leu Val Gln Asn Pro Asp Val Phe
            260                 265                 270

Asp Gly Lys Cys Trp Leu Ser Cys Phe Leu Gly Gln Ser Val Glu Val
        275                 280                 285
```

```
Arg Cys His Glu Glu His Leu Ala Asp Ala Phe Gly Tyr Gln Thr Lys
    290                 295                 300

Gly Val His Gly Lys Tyr Leu Gln Arg Arg Leu Gln Val Arg Gly Ile
305                 310                 315                 320

Arg Ala Val Val Asp Pro Asp Gly Pro Ile His Val Glu Ala Leu Ser
                325                 330                 335

Cys Pro Gln Ser Trp Ile Arg His Leu Thr Leu Asp Asp Val Thr
                340                 345                 350

Pro Gly Phe Val Arg Leu Thr Ser Leu Arg Ile Val Pro Asn Thr Glu
            355                 360                 365

Pro Thr Thr Ser Arg Ile Phe Arg Phe Gly Ala His Lys Trp Tyr Gly
370                 375                 380

<210> SEQ ID NO 37
<211> LENGTH: 383
<212> TYPE: PRT
<213> ORGANISM: Porcine reproductive and respiratory syndrome virus

<400> SEQUENCE: 37

Met Ser Gly Thr Phe Ser Arg Cys Met Cys Thr Pro Ala Ala Arg Val
1               5                   10                  15

Phe Trp Asn Ala Gly Gln Val Tyr Cys Thr Arg Cys Leu Ser Ala Arg
                20                  25                  30

Ser Leu Leu Pro Pro Glu Leu Gln Asp Ile Asp Leu Ala Ala Ile Gly
            35                  40                  45

Leu Phe Tyr Lys Pro Lys Asp Lys Leu His Trp Lys Val Pro Ile Gly
    50                  55                  60

Ile Pro Gln Val Glu Cys Thr Pro Ser Gly Cys Cys Trp Leu Ser Gly
65                  70                  75                  80

Ile Phe Pro Leu Ala Arg Met Thr Ser Gly Asn His Asn Phe Leu Gln
                85                  90                  95

Arg Leu Val Lys Val Ala Asp Val Leu Tyr Arg Asp Gly Cys Leu Thr
            100                 105                 110

Ser Arg His Leu Arg Glu Leu Gln Val Tyr Glu Arg Gly Cys Ser Trp
        115                 120                 125

Tyr Pro Ile Thr Gly Pro Val Pro Gly Met Gly Leu Tyr Ala Asn Ser
    130                 135                 140

Met His Val Ser Asp Gln Pro Phe Pro Gly Ala Thr His Val Leu Thr
145                 150                 155                 160

Asn Ser Pro Leu Pro Gln Gln Ala Cys Arg Gln Pro Phe Cys Pro Phe
                165                 170                 175

Glu Glu Ala His Ala Asp Val Tyr Asp Ile Gly Arg Gly Ala Val Met
            180                 185                 190

Tyr Val Ala Gly Gly Lys Val Ser Trp Ala Pro Arg Gly Gly Asn Glu
        195                 200                 205

Val Lys Phe Glu Pro Val Pro Lys Glu Leu Lys Leu Val Ala Asn Arg
    210                 215                 220

Leu His Thr Ser Phe Pro Pro His His Val Val Asp Met Ser Lys Phe
225                 230                 235                 240

Thr Phe Ile Thr Pro Gly Ser Gly Val Ser Met Arg Val Glu Tyr Gln
                245                 250                 255

Tyr Gly Cys Leu Pro Ala Asp Thr Val Pro Glu Gly Asn Cys Trp Trp
            260                 265                 270

Arg Leu Leu Asp Ser Leu Pro Pro Glu Val Gln Tyr Lys Glu Ile Arg
        275                 280                 285
```

```
His Ala Asn Gln Phe Gly Tyr Gln Thr Lys His Gly Val Pro Gly Lys
    290                 295                 300

Tyr Leu Gln Arg Arg Leu Gln Val Asn Gly Leu Arg Ala Val Thr Asp
305                 310                 315                 320

Thr His Gly Pro Ile Val Leu Gln Tyr Phe Ser Val Lys Glu Ser Trp
                325                 330                 335

Ile Arg His Leu Lys Leu Val Glu Glu Pro Ser Leu Pro Gly Phe Glu
                340                 345                 350

Asp Leu Leu Arg Ile Arg Val Glu Pro Asn Thr Ser Pro Leu Ala Gly
            355                 360                 365

Lys Asp Glu Lys Ile Phe Arg Phe Gly Ser His Lys Trp Tyr Gly
370                 375                 380

<210> SEQ ID NO 38
<211> LENGTH: 383
<212> TYPE: PRT
<213> ORGANISM: Porcine reproductive and respiratory syndrome virus

<400> SEQUENCE: 38

Met Ser Gly Thr Phe Ser Arg Cys Met Cys Thr Pro Ala Ala Arg Val
1               5                   10                  15

Phe Trp Asn Ala Gly Gln Val Tyr Cys Thr Arg Cys Leu Ser Ala Arg
                20                  25                  30

Ser Leu Leu Pro Pro Glu Leu Gln Asp Ile Asp Leu Ala Ala Ile Gly
            35                  40                  45

Leu Phe Tyr Lys Pro Lys Asp Lys Leu His Trp Lys Val Pro Ile Gly
    50                  55                  60

Ile Pro Gln Val Glu Cys Thr Pro Ser Gly Cys Cys Trp Leu Ser Gly
65                  70                  75                  80

Ile Phe Pro Leu Ala Arg Met Thr Ser Gly Asn His Asn Phe Leu Gln
                85                  90                  95

Arg Leu Val Lys Val Ala Asp Val Leu Tyr Arg Asp Gly Cys Leu Thr
                100                 105                 110

Ser Arg His Leu Arg Glu Leu Gln Val Tyr Glu Arg Gly Cys Ser Trp
            115                 120                 125

Tyr Pro Ile Thr Gly Pro Val Pro Gly Met Gly Leu Tyr Ala Asn Ser
    130                 135                 140

Met His Val Ser Asp Gln Pro Phe Pro Gly Ala Thr His Val Leu Thr
145                 150                 155                 160

Asn Ser Pro Leu Pro Gln Gln Ala Cys Arg Gln Pro Phe Cys Pro Phe
                165                 170                 175

Glu Glu Ala His Ala Thr Val Tyr Asp Ile Gly His Asp Ala Val Met
                180                 185                 190

Tyr Val Ala Glu Arg Lys Val Ser Trp Ala Pro Arg Gly Gly Asp Glu
            195                 200                 205

Val Lys Phe Glu Ala Val Pro Gly Glu Leu Lys Leu Ile Ala Asn Arg
    210                 215                 220

Leu Arg Thr Ser Phe Pro Pro His His Thr Val Asp Met Ser Lys Phe
225                 230                 235                 240

Ala Phe Thr Ala Pro Gly Cys Gly Val Ser Met Arg Val Glu Arg Gln
                245                 250                 255

His Gly Cys Leu Pro Ala Asp Thr Val Pro Glu Gly Asn Cys Trp Trp
            260                 265                 270

Ser Leu Phe Asp Leu Leu Pro Leu Glu Val Gln Asn Lys Glu Ile Arg
```

```
                    275                 280                 285
His Ala Asn Gln Phe Gly Tyr Gln Thr Lys His Gly Val Ser Gly Lys
    290                 295                 300

Tyr Leu Gln Arg Arg Leu Gln Val Asn Gly Leu Arg Ala Val Thr Asp
305                 310                 315                 320

Leu Asn Gly Pro Ile Val Val Gln Tyr Phe Ser Val Lys Glu Ser Trp
                325                 330                 335

Ile Arg His Leu Lys Leu Ala Gly Glu Pro Ser Tyr Ser Gly Phe Glu
            340                 345                 350

Asp Leu Leu Arg Ile Arg Val Glu Pro Asn Thr Ser Pro Leu Ala Asp
        355                 360                 365

Lys Glu Glu Lys Ile Phe Arg Phe Gly Ser His Lys Trp Tyr Gly
    370                 375                 380

<210> SEQ ID NO 39
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tttttttttt tttttttttt tttttttttt tttttttttt tttttttttt tttttttttt    60

<210> SEQ ID NO 40
<211> LENGTH: 4
<212> TYPE: PRT
<213> ORGANISM: Porcine reproductive and respiratory syndrome virus

<400> SEQUENCE: 40

Gly Arg Pro Arg
1

<210> SEQ ID NO 41
<211> LENGTH: 5
<212> TYPE: PRT
<213> ORGANISM: Porcine reproductive and respiratory syndrome virus

<400> SEQUENCE: 41

Asn Gly Arg Pro Arg
1               5

<210> SEQ ID NO 42
<211> LENGTH: 6
<212> TYPE: PRT
<213> ORGANISM: Porcine reproductive and respiratory syndrome virus

<400> SEQUENCE: 42

Pro Asn Gly Arg Pro Arg
1               5
```

The invention claimed is:

1. A plasmid or cDNA construct which encodes a genotype I PRRS virus and which is capable of producing infectious virus when transfected into cells, and comprises a cDNA sequence having at least 94% sequence identity over the full length of the cDNA sequence of SEQ ID NO:1.

2. The plasmid or cDNA construct of claim 1, wherein said molecule comprises a cDNA sequence having at least 95% sequence identity with the cDNA sequence of SEQ ID NO:1.

3. A genotype I PRRS virus whose genome comprises a plasmid or cDNA construct according to claim 1 or whose genome comprises an RNA molecule encoded by cDNA sequence according to claim 1.

4. A method for producing a genotype I PRRS virus comprising transfecting a cell with the DNA construct of claim 3.

5. A composition comprising a plasmid or cDNA construct of claim 1 suspended in a suitable amount of a pharmaceutically acceptable diluent or excipient.

* * * * *